United States Patent
Menchen et al.

(12) 
(10) Patent No.: US 6,583,168 B1
(45) Date of Patent: Jun. 24, 2003

(54) SULFONATED DIARYLRHODAMINE DYES

(75) Inventors: Steven M. Menchen, Fremont; Scott C. Benson, Alameda; Joe Y. L. Lam, Castro Valley; Weiguo Zhen; Daqing Sun, both of Foster City; Barnett B. Rosenblum, San Jose; Shaheer H. Khan, Foster City; Meng Taing, San Mateo, all of CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/724,855

(22) Filed: Nov. 28, 2000

Related U.S. Application Data

(60) Continuation-in-part of application No. 09/556,040, filed on Apr. 20, 2000, now Pat. No. 6,221,606, which is a division of application No. 09/199,402, filed on Nov. 24, 1998, now Pat. No. 6,111,116, which is a division of application No. 08/978,775, filed on Nov. 25, 1997, now Pat. No. 5,936,087.

(51) Int. Cl.$^7$ .......................................... C07D 311/78
(52) U.S. Cl. ...................... 514/410; 514/453; 549/381; 549/382; 548/417
(58) Field of Search ................. 514/410, 453; 549/381, 382; 548/417

(56) References Cited

U.S. PATENT DOCUMENTS

| | | | |
|---|---|---|---|
| 5,750,409 | A | 5/1998 | Herman et al. .............. 549/382 |
| 6,051,719 | A | 4/2000 | Benson et al. |
| 6,111,116 | A | 8/2000 | Benson et al. |
| 6,130,101 | A | 10/2000 | Mao et al. |
| 6,221,606 | B1 | 4/2001 | Benson et al. |
| 6,326,153 | B2 | 12/2001 | Benson et al. |

FOREIGN PATENT DOCUMENTS

| | | |
|---|---|---|
| DE | 4137934 | 11/1991 |
| EP | 0 543 333 | 5/1993 |
| EP | 0 805 190 | 11/1997 |
| WO | WO 94/05688 | 3/1994 |

OTHER PUBLICATIONS

Arden et al., "Fluorescence and Lasing Properties of Rhodamine Dyes," Jnl. of Luminescence 48&49:352–358 (1991).

Arden–Jacob, Jutta; *Reihe Chemie*; Neue langwellige Xanthen–Farbstoffe fur Fluoreszenzsonden und Farbstofflaser; Verlag Shaker, pub.; Prof. Dr. K.H. Drexhage and Prof. Dr. G. von Bunau, eds.; pp. 1–169 (Dec. 12, 1992).

Gee et al., "Novel Derivatization of Protein Thiols with Fluorinated Fluoresceins," Tetrahedron Letters 3(44):7905–7908 (1996).

Haughland et al., "New Fluorescein, Rhodamine and Texa Red Analogs with Higher Fluorescence and Improved Photostability," Proceedings of the Xth International Congress, Histochemistry and Cytochemistry, pp. 273 (1996).

Lieberwirth et al., "Development of New Multiplex Dyes: Intramolecular Fluorescene Quenching of Rhodamine Dyes," Jnl. of Flurescence 7(1):59S–61S.

Onda et al., "Heterocycles. IV. Photoyses of the 4–Arylacetylated 1,2–Dihydroisoquinoline, Isocarbostyril and its Enol Acetates," *Chemical and Pharmaceutical Bulletin* 25(11):2935–2941 (Mar. 12, 1977).

Sauer et al., "New Fluorescent Dyes in the Red Region for Biodiagnostics," Jnl. of Fluorescence, 5(3):247–261 (1995).

Sauer et al., Physikalisch–Chemisches Institut, Heidelberg, Germany and Arden–Jacob et al., Institut for Physikalische Chemie, Siegen, Germany; "Design of Multiplex Dyes for the Detection of Different Biomolecules".

Sotomayor et al., "Bischler–Napieralski Cyclization–N/C–Alkylation Sequences for the Construction of Isoquinoline Alkaloids. Synthesis of Protoberberines and Benzo[c]phenanthridines via c–2'–Funtionalized 3–Arylisoquinolines[1], " *Journal of Organic Chemistry* 61(12):4062–4072 (1996).

Sun et al., "Synthesis of Fluorinated Fluoresceins," J. Org. Chem. 62(19):6469–6475 (1997).

Takai, Hideyuki, "Electrophotographic photoconductors," *Chemical Abstracts* 114(22):743 (Jun. 3, 1991).

Tsunoda et al., "Naphthazolylphenyl azides," *Chemical Abstracts* 83(14):75 (Oct. 6, 1975).

*Primary Examiner*—Zinna Northington Davis
(74) *Attorney, Agent, or Firm*—Alex Andrus

(57) ABSTRACT

Sulfonated diarylrhodamine compounds are useful as fluorescent labels of nucleosides, nucleotides, polynucleotides, and polypeptides. The compounds find particular application in the area of fluorescent nucleic acid analysis, e.g., automated DNA sequencing and fragment analysis, detection of probe hybridization in hybridization arrays, detection of nucleic acid amplification products, and the like.

23 Claims, 25 Drawing Sheets

10    11    12

13    14 R = Me            15 R = Me
      16 R = (CH$_2$)$_3$SO$_3$$^\ominus$    17 R = (CH$_2$)$_3$SO$_3$$^\ominus$

41

42

43

44

45

46

47

67 $R_1 = R_2 = $ -Ph-Ph-
72 $R_1 = R_2 = $ -Ph-
76 $R_1 = $ -(CH$_2$)$_5$ -
   $R_2 = $ -Ph-

82 $R_1 = R_2 = $ -Ph-Ph-
83 $R_1 = R_2 = $ -Ph-
84 $R_1 = $ -(CH$_2$)$_5$ -
   $R_2 = $ -Ph-

94

95

96

97

98

99

106
 107
 108
 109

| $R^{12}-L^{12}-$ | $-L^2-R^2$ | |
|---|---|---|
|  | $-CH_2CH_2CH_2SO_3^-$ | 110 |
| $HO_2CCH_2CH_2CH_2CH_2CH_2-$ | $-CH_2CH_2CH_2SO_3^-$ | 111 |
|  |  | 112 |
|  | $-CH_2CH_2CH_2SO_3^-$ | 113 |

| $R^{12}-L^{12}-$ | $-L^2-R^2$ | |
|---|---|---|
|  |  | 114 |
|  |  | 115 |
| | | 116 |

SULFONATED DIARYLRHODAMINE DYES

This is a continuation-in-part of application Ser. No. 09/556,040, filed Apr. 20, 2000, now U.S. Pat. No. 6,221,606 which is a divisional application of Ser. No. 09/199,402, filed Nov. 24, 1998, now U.S. Pat. No. 6,111,116, which is a divisional of Ser. No. 08/978,775, filed Nov. 25, 1997, now U.S. Pat. No. 5,936,087, all of which are incorporated herein by reference.

I. FIELD OF THE INVENTION

This invention relates generally to fluorescent rhodamine dye compounds. More specifically, this invention relates to sulfonated diarylrhodamine dyes useful as fluorescent labeling reagents.

II. BACKGROUND

The non-radioactive detection of biological analytes utilizing fluorescent labels is an important technology in modern molecular biology. By eliminating the need for radioactive labels, safety is enhanced and the environmental impact and costs associated with reagent disposal is greatly reduced. Examples of methods utilizing such non-radioactive fluorescent detection include 4-color automated DNA sequencing, oligonucleotide hybridization methods, detection of polymerase-chain-reaction products, immunoassays, and the like.

In many applications it is advantageous to employ multiple spectrally distinguishable fluorescent labels in order to achieve independent detection of a plurality of spatially overlapping analytes, e.g., single-tube multiplex DNA probe assays and 4-color automated DNA sequencing methods. In the case of multiplex DNA probe assays, by employing spectrally distinguishable fluorescent labels, the number of reaction tubes may be reduced thereby simplifying experimental protocols and facilitating the production of application-specific reagent kits. In the case of 4-color automated DNA sequencing, multicolor fluorescent labeling allows for the analysis of multiple bases in a single lane thereby increasing throughput over single-color methods and reducing uncertainties associated with inter-lane electrophoretic mobility variations.

Assembling a set of multiple spectrally distinguishable fluorescent labels is problematic. Multi-color fluorescent detection imposes at least six severe constraints on the selection of dye labels, particularly for applications requiring a single excitation light source, an electrophoretic separation, and/or treatment with enzymes, e.g., automated DNA sequencing. First, it is difficult to find a set of structurally similar dyes whose emission spectra are spectrally resolved, since the typical emission band half-width for organic fluorescent dyes is about 40–80 nanometers (nm). Second, even if dyes with non-overlapping emission spectra are identified, the set may still not be suitable if the respective fluorescent quantum efficiencies are too low. Third, when several fluorescent dyes are used concurrently, simultaneous excitation becomes difficult because the absorption bands of the dyes are usually widely separated. Fourth, the charge, molecular size, and conformation of the dyes must not adversely affect the electrophoretic mobilities of the analyte. Fifth, the fluorescent dyes must be compatible with the chemistry used to create or manipulate the analyte, e.g., DNA synthesis solvents and reagents, buffers, polymerase enzymes, ligase enzymes, and the like. Sixth, the dye must have sufficient photostability to withstand laser excitation.

Currently available multiplex dye sets suitable in 4-color automated DNA sequencing applications require blue or blue-green laser light to adequately excite fluorescence emissions from all of the dyes making up the set, e.g., argon-ion lasers. Use of blue or blue-green lasers in commercial automated DNA sequencing systems is disadvantageous because of the high cost and limited lifetime of such lasers.

III. SUMMARY

In a first aspect, the invention comprises sulfonated diarylrhodamine dye compounds having the structures:

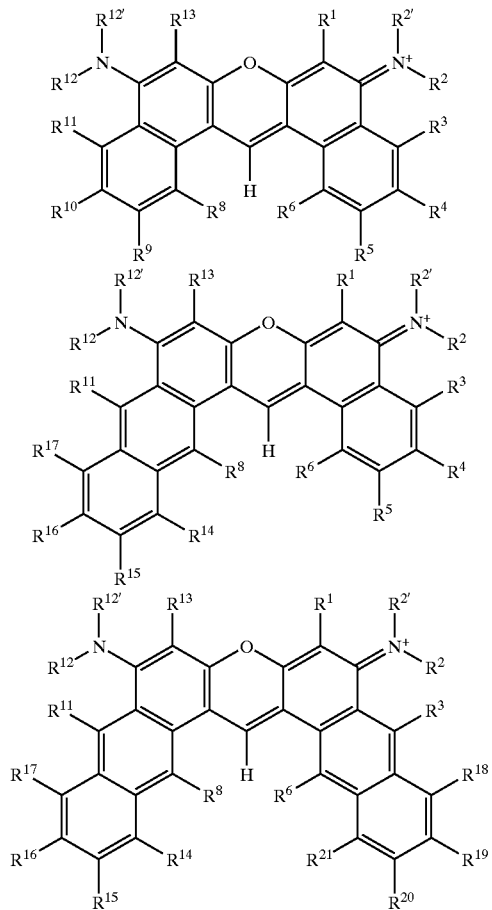

including nitrogen- and aryl-substituted forms thereof. At least one of $R^1$, $R^3$, $R^4$, $R^5$, $R^6$, $R^8$, $R^9$, $R^{10}$, $R^{11}$, $R^{13}$, $R^{14}$, $R^{15}$, $R^{16}$, $R^{17}$, $R^{18}$, $R^{19}$, $R^{20}$, and $R^{21}$ is sulfonate.

Nitrogen substituents, $R^2$, $R^{2'}$, $R^{12}$ and $R^{12'}$, may be $C_1$–$C_6$ alkylsulfonate or $C_4$–$C_{10}$ arylsulfonate. In certain embodiments, alkylsulfonate is —$(CH_2)_n$—$SO_3H$, and n is an integer from 1 to 6, and arylsulfonate is:

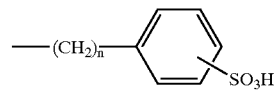

wherein n is 0 or 1.

In other embodiments, nitrogen substituents, $R^2$, $R^{2'}$, $R^{12}$ and $R^{12'}$, may be $C_1$–$C_6$ alkylcarboxylate or $C_4$–$C_{10}$ arylcarboxylate:

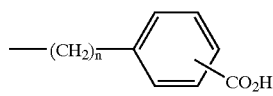

wherein n is 0 or 1.

Another aspect of the invention includes energy-transfer dye compounds comprising a donor dye capable of absorbing light at a first wavelength and emitting excitation energy in response thereto; an acceptor dye capable of absorbing the excitation energy emitted by the donor dye and fluorescing at a second wavelength in response; and a linker for linking the donor dye and the acceptor dye; wherein at least one of the donor dye and acceptor dye is a sulfonated diarylrhodamine compound.

Another aspect of the invention is a labelled nucleoside, nucleotide, polynucleotide or polypeptide wherein the label is a sulfonated diarylrhodamine compound or an energy-transfer dye comprising a sulfonated diarylrhodamine compound.

Another aspect of the invention is a labelling reagent, including phosphoramidite or active ester linking moieties of a sulfonated diarylrhodamine compound, which form covalent attachments with substrates and methods of labelling substrates with the reagents.

Another aspect of the invention is methods for forming a labelled substrate comprising the step of reacting a substrate with the linking moiety of a sulfonated diarylrhodamine compound or an energy-transfer dye comprising a sulfonated diarylrhodamine compound.

Another aspect of the invention is methods of generating a labelled primer extension product by extending a primer-target hybrid with an enzymatically-incorporatable nucleotide. The primer or the nucleotide may be labelled with a sulfonated diarylrhodamine compound or an energy-transfer dye comprising a sulfonated diarylrhodamine compound.

Another aspect of the invention is methods of polynucleotide sequencing by forming a mixture of four classes of polynucleotides where each class is labelled at the 3' terminal nucleotide with a sulfonated diarylrhodamine compound or an energy-transfer dye comprising a sulfonated diarylrhodamine compound, and the labels are spectrally resolvable.

Another aspect of the invention is methods of oligonucleotide ligation by annealing two probes to a target sequence and forming a phosphodiester bond between the 5' terminus of one probe and the 3' terminus of the other probe wherein one or both probes are labelled with a sulfonated diarylrhodamine compound or an energy-transfer dye comprising a sulfonated diarylrhodamine compound.

Another aspect of the invention is methods of amplification by annealing two or more primers to a target polynucleotide and extending the primers by a polymerase and a mixture of enzymatically-extendable nucleotides wherein at least one of the primers or one of the nucleotides is labelled with a sulfonated diarylrhodamine compound or an energy-transfer dye comprising a sulfonated diarylrhodamine compound.

Another aspect of the invention is kits of reagents including a sulfonated diarylrhodamine compound or an energy-transfer dye comprising a sulfonated diarylrhodamine compound.

These and other features and advantages of the present invention will become better understood with reference to the following description, figures, and appended claims.

IV. BRIEF DESCRIPTION OF THE FIGURES

V. DETAILED DESCRIPTION OF EXEMPLARY EMBODIMENTS

Figure 1:
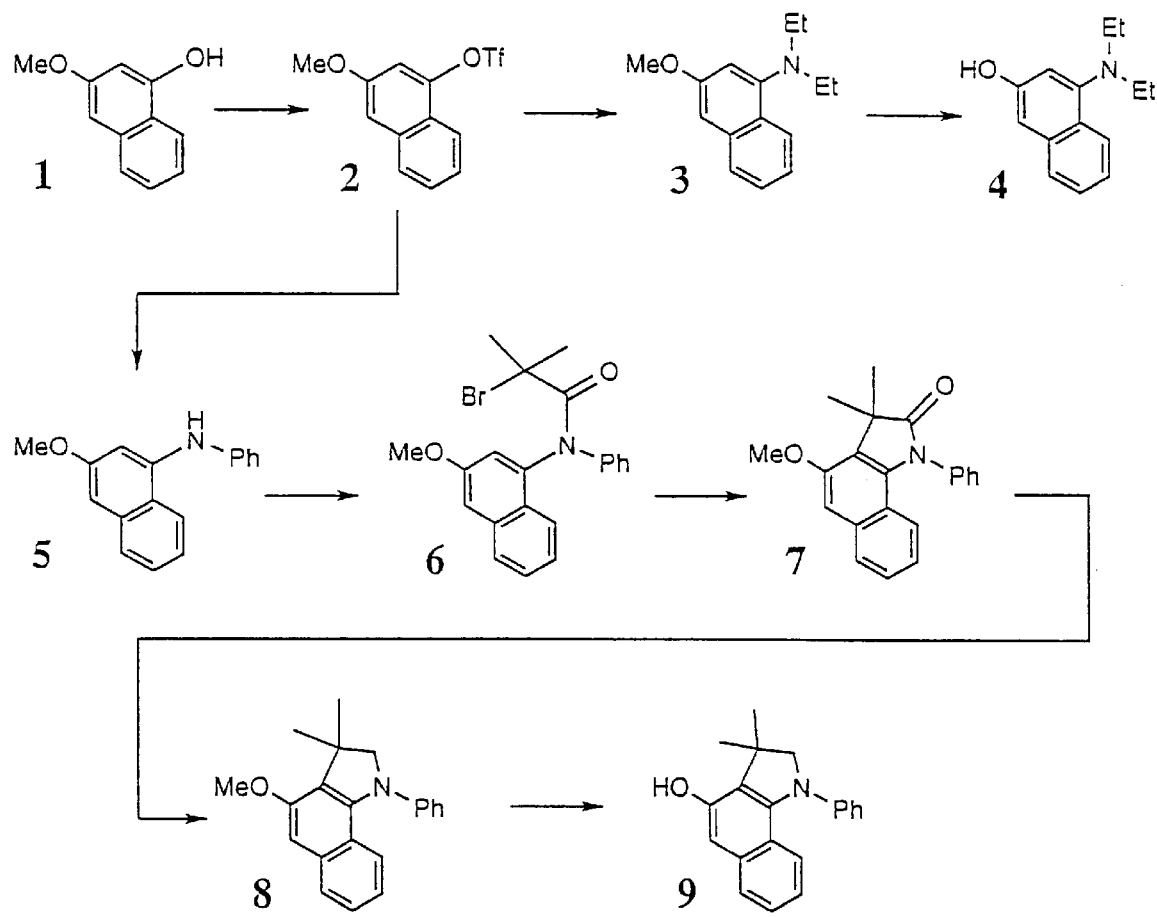
FIGS. 1–3 show exemplary synthetic pathways for the synthesis of the 1-amino-3-hydroxynaphthalene intermediates of the invention.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

V.1 Definitions

Unless stated otherwise, the following terms and phrases as used herein are intended to have the following meanings:

"Spectral resolution" in reference to a set of dyes means that the fluorescent emission bands of the dyes are sufficiently distinct, i.e., sufficiently non-overlapping, that reagents to which the respective dyes are attached, e.g. polynucleotides, can be distinguished on the basis of a fluorescent signal generated by the respective dyes using standard photodetection systems, e.g. employing a system of band pass filters and photomultiplier tubes, charged-coupled devices and spectrographs, or the like, as exemplified by the systems described in U.S. Pat. Nos. 4,230,558, 4,811,218, or in Wheeless et al, pgs. 21–76, in *Flow Cytometry: Instrumentation and Data Analysis* (Academic Press, New York, 1985).

"Heterocycle" means cyclic compounds in which one or more ring atoms are not carbon, i.e., are heteroatoms. Exemplary heterocycles include but are not limited to pyrrole, indole, furan, benzofuran, thiophene, benzothiophene, 2-pyridyl, 3-pyridyl, 4-pyridyl, 2-quinolyl, 3-quinolyl, 4-quinolyl, 2-imidazole, 4-imidazole, 3-pyrazole, 4-pyrazole, pyridazine, pyrimidine, pyrazine, cinnoline, pthalazine, quinazoline, quinoxaline, 3-(1,2,4-N)-triazolyl, 5-(1,2,4-N)-triazolyl, 5-tetrazolyl, 4-(1-O, 3-N)-oxazole, 5-(1-O, 3-N)-oxazole, 4-(1-S, 3-N)-thiazole, 5-(1-S, 3-N)-thiazole, 2-benzoxazole, 2-benzothiazole, 4-(1,2,3-N)-benzotriazole, and benzimidazole.

"Linker" means a chemical moiety comprising a covalent bond or a chain of atoms that covalently attaches a label to a polynucleotide, or one label to another.

"Linking moiety" means a chemically reactive group, substituent or moiety, e.g. a nucleophile or electrophile, capable of reacting with another molecule to form a covalent bond, or linkage.

The term "label", as used herein, means any moiety which can be attached to a substrate, e.g., an oligonucleotide, nucleotide or nucleotide 5'-triphosphate, and that functions to: (i) provide a detectable signal; (ii) interact with a second label to modify the detectable signal provided by the first or second label, e.g. FRET; (iii) stabilize hybridization, i.e. duplex formation; (iv) affect mobility, e.g. electrophoretic mobility or cell-permeability, by charge, hydrophobicity, shape, or other physical parameters, or (v) provide a capture moiety, e.g., affinity, antibody/antigen, or ionic complexation.

"Substrate" is an entity to which dye compounds of the present invention are attached. Substrates include, but are not limited to a (i) polynucleotide, (ii) nucleoside and nucleotide, (iii) polypeptide, (iv) carbohydrate, (v) ligand, and (vi) any analog of the preceding (i) to (v).

"Substituted" as used herein refers to a molecule wherein one or more hydrogen atoms are replaced with one or more non-hydrogen atoms, functional groups or moieties. For example, an unsubstituted nitrogen is —NH$_2$, while a substituted nitrogen is —NHCH$_3$. Exemplary substituents include but are not limited to halo, e.g., fluorine and chlorine, (C$_1$–C$_8$)alkyl, sulfate, sulfonate, sulfone, amino, ammonium, amido, nitrile, lower alkoxy, phenoxy, aromatic, phenyl, polycyclic aromatic, heterocycle, water-solubilizing group, and linking moiety.

"Polycyclic aromatic" means aromatic hydrocarbons having multiple ring structures including biaryls and condensed benzenoid hydrocarbons. The biaryls are benzenoid compounds where two or more rings are linked together by a single bond. The parent system of this class is biphenyl. The condensed benzenoid compounds are characterized by two or more benzene rings fused together at ortho positions in such a way that each pair of rings shares two carbons. The simplest members of this group are naphthalene, with two rings, and anthracene and phenanthrene, each with three rings.

"Alkyl" means a saturated or unsaturated, branched, straight-chain, branched, or cyclic hydrocarbon radical derived by the removal of one hydrogen atom from a single carbon atom of a parent alkane, alkene, or alkyne. Typical alkyl groups consist of 1–12 saturated and/or unsaturated carbons, including, but not limited to, methyl, ethyl, propyl, butyl, and the like.

"Alkoxy" means —OR where R is (C$_1$–C$_6$) alkyl.

"Alkyldiyl" means a saturated or unsaturated, branched, straight chain or cyclic hydrocarbon radical of 1–20 carbon atoms, and having two monovalent radical centers derived by the removal of two hydrogen atoms from the same or two different carbon atoms of a parent alkane, alkene or alkyne. Typical alkyldiyl radicals include, but are not limited to, 1,2-ethyldiyl, 1,3-propyldiyl, 1,4-butyldiyl, and the like.

"Aryl" means a monovalent aromatic hydrocarbon radical of 6–20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Aryldiyl" means an unsaturated cyclic or polycyclic hydrocarbon radical of 6–20 carbon atoms having a conjugated resonance electron system and at least two monovalent radical centers derived by the removal of two hydrogen atoms from two different carbon atoms of a parent aryl compound.

"Substituted alkyl", "substituted alkyldiyl", "substituted aryl" and "substituted aryldiyl" mean alkyl, alkyldiyl, aryl and aryldiyl respectively, in which one or more hydrogen atoms are each independently replaced with another substituent. Typical substituents include, but are not limited to, —X, —R, —O$^-$, —OR, —SR, —S$^-$, —NR$_2$, —NR$_3$, =NR, —CX$_3$, —CN, —OCN, —SCN, —NCO, —NCS, —NO, —NO$_2$, =N$_2$, —N$_3$, NC(O)R, —C(O)R, —C(O)NRR—S(O)$_2$O$^-$, —S(O)$_2$OH, —S(O)$_2$R, —OS(O)$_2$OR, —S(O)$_2$NR, —S(O)R, —OP(O)O$_2$RR—P(O)O$_2$RR—P(O)(O)$_2$—P(O)(OH)$_2$, —C(O)R, —C(O)X, —C(S)R, —C(O)OR, —C(O)O$^-$, —C(S)OR, —C(O)SR, —C(S)SR, —C(O)NRR, —C(S)NRR, —C(NR)NRR, where each X is independently a halogen and each R is independently —H, alkyl, aryl, heterocycle, or linking group.

"Internucleotide analog" means a phosphate ester analog of an oligonucleotide such as: (i) alkylphosphonate, e.g. C$_1$–C$_4$ alkylphosphonate, especially methylphosphonate; (ii) phosphoramidate; (iii) alkylphosphotriester, e.g. C$_1$–C$_4$ alkylphosphotriester; (iv) phosphorothioate; and (v) phosphorodithioate. Internucleotide analogs also include non-phosphate analogs wherein the sugar/phosphate subunit is replaced by an a non-phosphate containing backbone structure. One type of non-phosphate oligonucleotide analogs has an amide linkage, such as a 2-aminoethylglycine unit, commonly referred to as PNA (Nielsen (1991) "Sequence-selective recognition of DNA by strand displacement with a thymidine-substituted polyamide", Science 254:1497–1500).

"Nucleobase" means a nitrogen-containing heterocyclic moiety capable of forming Watson-Crick hydrogen bonds in pairing with a complementary nucleobase or nucleobase analog, e.g. a purine, a 7-deazapurine, or a pyrimidine. Typical nucleobases are the naturally occurring nucleobases adenine, guanine, cytosine, uracil, thymine, and analogs of the naturally occurring nucleobases, e.g. 7-deazaadenine, 7-deazaguanine, 7-deaza-8-azaguanine, 7-deaza-8-azaadenine (Kutyavin, U.S. Pat. No. 5,912,340), inosine, nebularine, nitropyrrole, nitroindole, 2-aminopurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, O$^6$-methylguanine, N$^6$-methyladenine, O$^4$-methylthymine, 5,6-dihydrothymine, 5,6-dihydrouracil, 4-methyl-indole, and ethenoadenine (Fasman (1989) *Practical Handbook of Biochemistry and Molecular Biology*, pp. 385–394, CRC Press, Boca Raton, Fla.).

"Nucleoside" means a compound consisting of a nucleobase linked to the C-1' carbon of a ribose sugar. The ribose may be substituted or unsubstituted. Substituted nibose sugars include, but are not limited to, those riboses in which one or more of the carbon atoms, e.g., the 3'-carbon atom, is substituted with one or more of the same or different —R, —OR, —NRR or halogen groups, where each R is independently hydrogen, $C_1$–$C_6$ alkyl or $C_5$–$C_{14}$ aryl. Riboses include ribose, 2'-deoxyribose, 2',3'-dideoxyribose, 3'-haloribose, 3'-fluororibose, 3'-chlororibose, 3'-alkylribose, e.g. 2'-O-methyl, 4'-α-anomeric nucleotides, 1-α-anomeric nucleotides, and 2'-4'-linked and other "locked", bicyclic sugar modifications (Imanishi WO 98/22489; Imanishi WO 98/39352; Wengel WO 99/14226). When the nucleobase is purine, e.g. A or G, the ribose sugar is attached to the $N^9$-position of the nucleobase. When the nucleobase is pyrimidine, e.g. C, T or U, the pentose sugar is attached to the $N^1$-position of the nucleobase (Kornberg and Baker, (1992) *DNA Replication, $2^{nd}$* Ed., Freeman, San Francisco, Calif.).

"Nucleotide" means a phosphate ester of a nucleoside, as a monomer unit or within a nucleic acid. Nucleotides are sometimes denoted as "NTP", or "dNTP" and "ddNTP" to particularly point out the structural features of the ribose sugar. "Nucleotide 5'-triphosphate" refers to a nucleotide with a triphosphate ester group at the 5' position. The triphosphate ester group may include sulfur substitutions for the various oxygens, e.g. α-thio-nucleotide 5'-triphosphates.

"Enzymatically incorporatable" is a property of a nucleotide in which it is capable of being enzymatically incorporated onto the terminus, e.g. 3', of a nascent polynucleotide chain through the action of a polymerase enzyme.

"Terminator" means an enzymatically incorporatable nucleotide which prevents subsequent incorporations of nucleotides to the resulting polynucleotide chain and thereby halt polymerase extension. Typical terminators lack a 3'-hydroxyl substituent and include 2', 3'-dideoxyribose, 2', 3'-didehydroribose, and 2', 3'-dideoxy, 3'-haloribose, e.g. 3'-fluoro. Alternatively, a ribofuranose analog could be used, such as arabinose. Exemplary nucleotide terminators include 2',3'-dideoxy-β-D-ribofuranosyl, β-D-arabinofuranosyl, 3'-deoxy-β-D-arabinofuranosyl, 3'-amino-2',3'-dideoxy-β-D-ribofuranosyl, and 2',3'-dideoxy-3'-fluoro-β-D-ribofuranosyl (Chidgeavadze (1984) Nucleic Acids Res., 12: 1671–1686; and Chidgeavadze (1985) FEB. Lett., 183: 275–278). Nucleotide terminators also include reversible nucleotide terminators (Metzker (1994) Nucleic Acids Res., 22(20): 4259).

"Enzymatically extendable" is a property of a nucleotide in which it is enzymatically incorporatable at the terminus of a polynucleotide and the resulting extended polynucleotide can undergo subsequent incorporations of nucleotides or nucleotide analogs.

The terms "target sequence" and "target polynucleotide" mean a polynucleotide sequence that is the subject of hybridization with a complementary polynucleotide, e.g., a primer or probe. The sequence can be composed of DNA, RNA, an analog thereof, including combinations thereof.

"Water solubilizing group" means a substituent which increases the solubility of the compounds of the invention in aqueous solution. Exemplary water-solubilizing groups include but are not limited to quaternary amine, sulfate, sulfonate, carboxylate, phosphonate, phosphate, polyether, polyhydroxyl, and boronate.

As used herein, the terms "oligonucleotide" and "polynucleotide" are used interchangeably and mean single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+)NH_4^+$, trialkylammonium, $Mg^{2+}$, $Na^+$ and the like. A polynucleotide may be composed entirely of deoxyribonucleotides, entirely of ribonucleotides, or chimeric mixtures thereof. Polynucleotides may be comprised of internucleotide, nucleobase and sugar analogs. Polynucleotides typically range in size from a few monomeric units, e.g. 5–40, when they are frequently referred to as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted.

"Rhodamine dye" refers to dyes including the general polycyclic structure

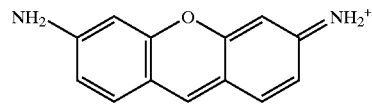

including any and all substituted versions thereof.

V.2 1-Amino-3-Methoxynaphthalene and Anthracene Intermediates

A class of 1-amino-3-methoxynaphthalene (FORMULA I) and 1-amino-3-methoxyanthracene (FORMULA II) compounds are useful as intermediates in the synthesis of sulfonated diarylrhodamine dyes. The compounds of Formulas I and II further include aryl- and nitrogen-substituted forms thereof. (Note that all molecular structures provided herein are intended to encompass not only the exact electronic structures presented, but also include all resonant structures, protonation states and associated counterions thereof.)

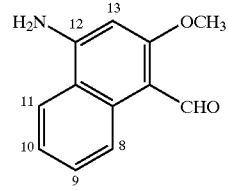

FORMULA I

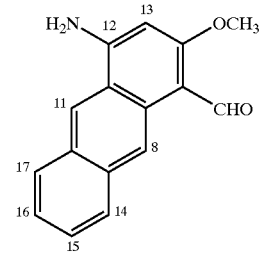

FORMULA II

In one embodiment of the compounds of Formulas I and II, the C-12-bonded nitrogen and the C-12 and C-13 carbons may form a first ring structure having from 4 to 7 members, and/or the C-12-bonded nitrogen and the C-11 and C-12 carbons form a second ring structure having from 5 to 7 members. The first and/or second ring structure may have five members, where the five membered ring structure may include one gem disubstituted carbon. The gem substituents may be alkyl, e.g., methyl. In another embodiment, the five membered ring is substituted with a linking moiety. In this embodiment wherein the C-12-bonded nitrogen and the C-12 and C-13 carbons form a first ring structure having from 4 to 7 members, and/or the C-12-bonded nitrogen and the C-11 and C-12 carbons form a second ring structure having from 5 to 7 members.

Nitrogen substituents may include alkyl, phenyl, aromatic, heterocycle, polycyclic aromatic, water-solubilizing group, linking moiety, and substituted forms thereof. The nitrogen substituents may be alkyl, phenyl, or substituted forms thereof, wherein substituents may be linking moiety, sulfonate or water-solubilizing group. Exemplary water-solubilizing groups are carboxylate, sulfonate, phosphonate, phosphate, quaternary amine, sulfate, polyhydroxyl, and water-soluble polymer. In one embodiment, the nitrogen substituent is —L—R, wherein L may be any linker and R is linking moiety or water-solubilizing group. In certain embodiments, L is,

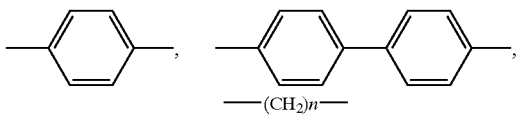

where n ranges from 1 to 8.

The compounds of Formulas I and II may include one or more substituents at one or more aryl positions, e.g. C-8 to C-11, and C-13. Substituents may include formyl, hydroxyl, fluorine, chlorine, alkyl, sulfate, sulfonate, sulfone, sulfonamide, sulfoxide, amino, ammonium, amido, nitrile, lower alkoxy, phenoxy, aromatic, phenyl, polycyclic aromatic, water-solubilizing group, heterocycle, and linking moiety, including substituted forms thereof. In one embodiment, the compound includes a fused aromatic ring bonded across the C-9 and C-10 carbons, or across the C-10 and C-11 carbons, including substituted forms thereof, where a substituent may be sulfonate.

Non-formylated versions of FORMULAS I and II are intermediates in the cyclization reactions to form the sulfonated diarylrhodamine dyes, detailed below.

Figure 2:
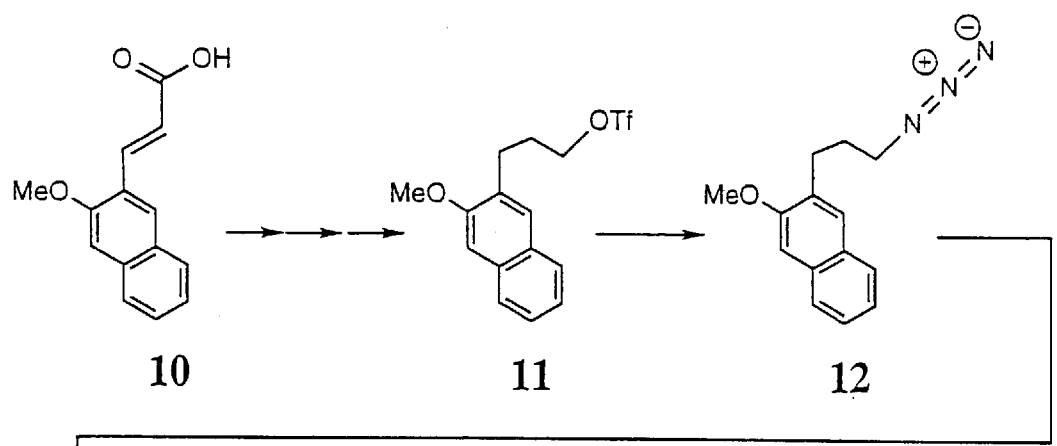
Figure 2:
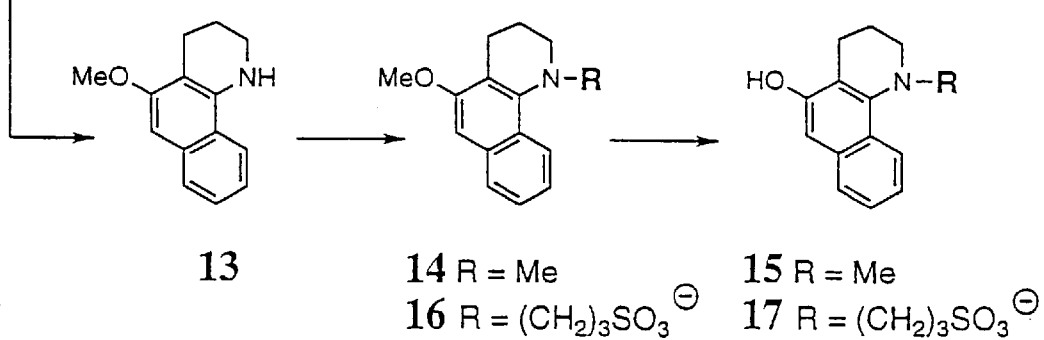
Figure 3:
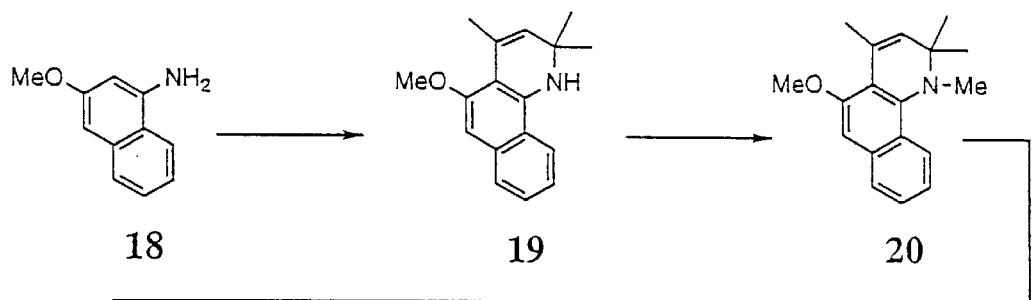
Figure 3:
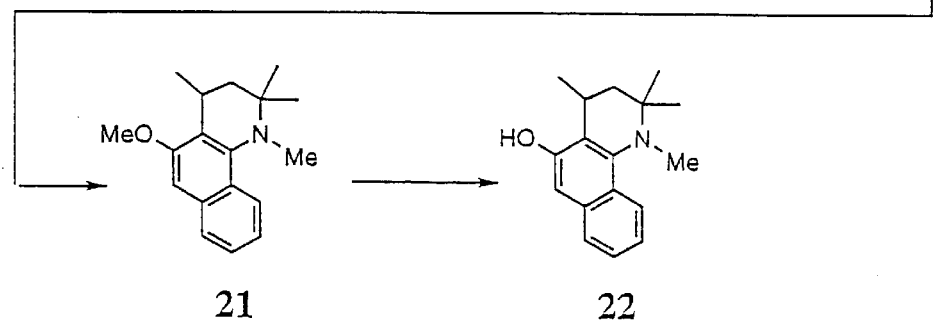
Figure 3:
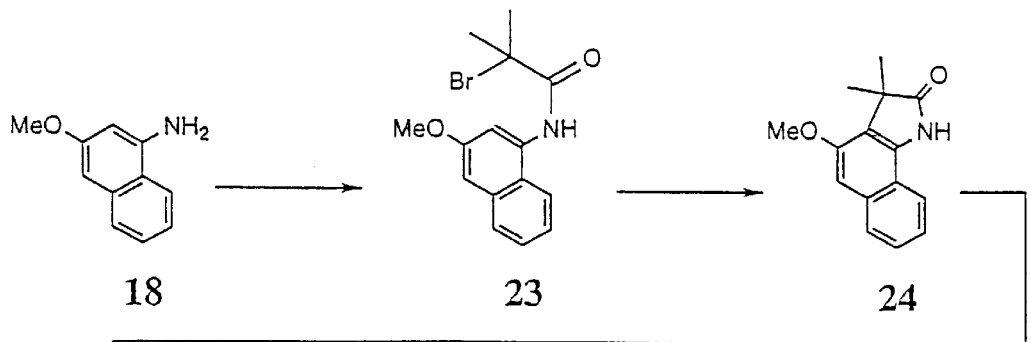
Figure 3:
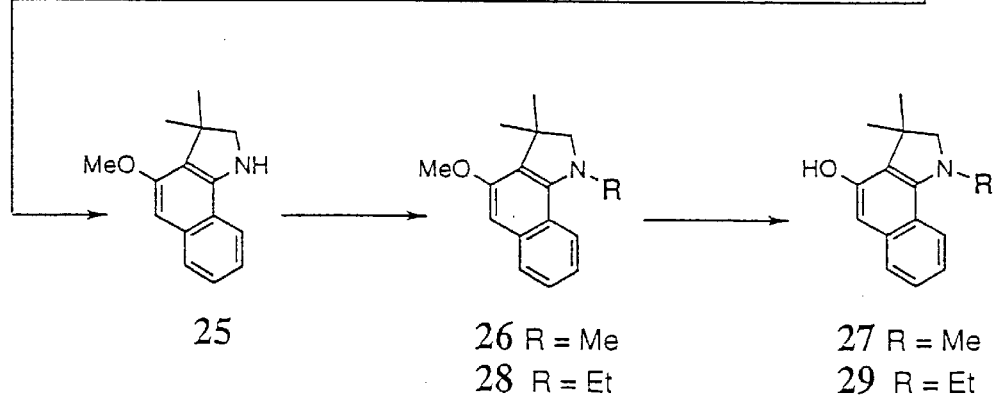

Representative 1-amino-3-hydroxynaphthalene and 1-amino-3-hydroxyanthracene compounds of the invention are shown in FIGS. 1–3, i.e., compounds 4, 9, 15, 17, 22, 27 and 29; FIGS. 10–13, i.e., compounds 62, 63, 68, 73 and 80; and FIGS. 16–20, i.e. compounds 86–109.

Those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

The compounds of the invention may bear multiple positive or negative charges. The net charge of the dyes of the invention may be either positive or negative. The counter ions associated with the dyes are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the dyes in association with any type of counter ion. Moreover, as the compounds can exists in a variety of different forms, the invention is intended to encompass not only forms of the dyes that are in association with counter ions (e.g., dry salts), but also forms that are not in association with counter ions (e.g., aqueous or organic solutions).

Various aspects of the above-described invention achieve one or more of the following important advantages, which are unexpected and surprising, over known fluorescent dye compounds useful for multiplex fluorescent detection: (1) the subject dye compounds may be efficiently excited by a low-cost red laser using wavelengths at or above 630 nm; (2) the emission spectra of the subject dye compounds can be modulated by minor variations in the type and location of nitrogen substituents and/or aryl substituents, allowing for the creation of dye sets having similar absorption characteristics yet spectrally resolvable fluorescence emission spectra; (3) the subject dye compounds may be easily attached to nucleosides, nucleotides or polynucleotides without compromising their favorable fluorescence properties; (4) the subject dye compounds have narrow emission bandwidths, i.e., the emission bandwidth has a full-width at half the maximum emission intensity of below about 70 nm; (5) the subject dye compounds are highly soluble in buffered aqueous solution while retaining a high quantum yield; (6) the subject dye compounds are relatively photostable; and (7) the subject dye compounds have relatively large extinction coefficients, i.e., greater than about 50,000.

Several synthetic methods are available for the synthesis of the 1-amino-3-hydroxynaphthalene compounds described above, different methods being preferred depending on the nature of the ring structure and the nitrogen substituents of the particular compound to be synthesized.

A first synthesis method suitable for the synthesis of 1-substituted-amino-3-hydroxynaphthalene compounds, e.g., 1-diethylamino-3-hydroxynaphthalene 4, is shown in FIG. 1. In this first method, a 3-methoxy-1-hydroxy naphthalene 1 is reacted with dry triethylamine and trifluoromethanesulfonic anhydride to form a crude 3-methoxynaphthalene-1-triflate 2. The triflate 2 is then reacted with an amine, e.g., a secondary amine, e.g., diethylamine, using palladium catalyzed triflate/amine coupling to form the substituted amine compound 3. Compound 3 is then deprotected using a boron tribromide deprotection procedure to produce the 1-amino-3-hydroxynaphthalene product, e.g., 1-diethylamino-3-hydroxynaphthalene 4. An example of this synthesis is provided in Example 1 below.

A second synthesis method suitable for the synthesis of benzoindoline compounds, e.g., N-phenyl-3,3-dimethyl-4-hydroxy-benzoindoline 9, is also shown in FIG. 1. In this method, the 3-methoxynaphthalene-1-triflate 2 is derivatized with a primary amine, e.g., aniline, using a palladium catalyzed triflate coupling reaction to give a secondary amine, e.g., 1-anilino-3-methoxynaphthalene 5. The secondary amine 5 is acylated using an acid chloride, e.g., an haloacetylchloride, to give a disubstituted amide, e.g., 1-amido-3-methoxynaphthalene 6. The tertiary amide 6 is cyclized using a Lewis-acid-catalyzed Friedel-Crafts cyclization procedure to give compound 7, e.g., using $AlCl_3$. Compound 7 is than reduced, e.g., using (lithium aluminum hydride) LAH, to give compound 8. Subsequent methoxy group deprotection by a boron tribromide deprotection procedure gives the benzoindoline, e.g., N-phenyl-3,3-dimethyl-4-hydroxy-benzoindoline 9. An example of this synthesis is provided in Example 2 below.

A third synthesis method suitable for the synthesis of N-substituted-5-hydroxy-(tetrahydro)benzoquinoline compounds, e.g., N-methyl-5-hydroxy-(tetrahydro) benzoquinoline 15, is shown in FIG. 2. In this method, compound 10 is synthesized from methoxy-naphthaldehyde by condensation with malonic acid using a piperidine catalyst in pyridine. Compound 10 is then reduced with hydrogen, followed by LAH reduction, and reacted with trifluoromethanesulfonic anhydride to give the triflate 11. The triflate 11 is reacted with NaN₃ to give compound 12. Compound 12 is complexed with a Lewis acid, e.g., AlCl₃, and refluxed yielding the cyclized benzoquinoline derivative 13. Next, a nitrogen substituent is added, e.g., the nitrogen is alkylated using a conventional alkylation procedure, e.g., the benzoquinoline derivative 13 is reacted with n-butyl lithium and an alkylating agent, e.g., MeI to give compound 14 or propane sultone to give compound 16. The methoxy group is then removed by a boron tribromide procedure giving a N-alkylbenzoquinoline derivative, e.g., compound 15 or 17. An example of this synthesis is provided in Example 3 below.

A fourth synthesis method suitable for the synthesis of N-substituted-2,2,4-trimethyl-5-hydroxy-benzoquinoline compounds, e.g of N-methyl-2,2,4-trimethyl-5-hydroxy-(tetrahydro)benzoquinoline 22, is shown in FIG. 3. In this method, following the procedure of Rosowsky (1965) Jour. Org. Chem. 30:1832, and references therein, 1-amino-3-methoxynaphthalene 18 is reacted with acetone catalyzed by iodine and then quenched with saturated Na₂S₂O₃ to give the benzoquinoline compound 19. Compound 19 is then alkylated with an alkylating agent, e.g., MeI, according to a general alkylation procedure to give compound 20. The alkylated compound 20 is reduced with H₂ catalyzed by Pd/C to give a N-methyl-methoxyquinoline intermediate 21, and subsequent methoxy group deprotection by a general boron tribromide procedure yields the N-substituted-2,2,4-trimethyl-5-hydroxy-benzoquinoline compound, e.g., N-methyl-2,2,4-trimethyl-5-hydroxy-(tetrahydro) benzoquinoline 22. An example of this synthesis is provided in Example 4 below.

A fifth general synthesis method suitable for the synthesis of N-substituted-3,3-dimethyl-4-hydroxy-benzoindoline compounds, e.g N-methyl-3,3-dimethyl-4-hydroxy-benzoindoline 27, is also shown in FIG. 3. In this method, a 1-amino-3-methoxynaphthalene 18 is acylated with an acid chloride, e.g., 2-bromo-2-methylpropionyl chloride, to give compound 23. Compound 23 is cyclized by reaction with AlCl₃ to give compound 24. Compound 24 is then reduced with LAH to give the 3,3-dimethyl-4-methoxybenzoindoline 25. Compound 25 is then alkylated with an alkylating agent, e.g., methyl iodide, to give a N-methyl-3,3-dimethyl-4-methoxybenzoindoline, e.g., compound 26. Subsequent methoxy group deprotection by with boron tribromide gives compound 27. An example of this synthesis is provided in Example 5.

Figure 17A:
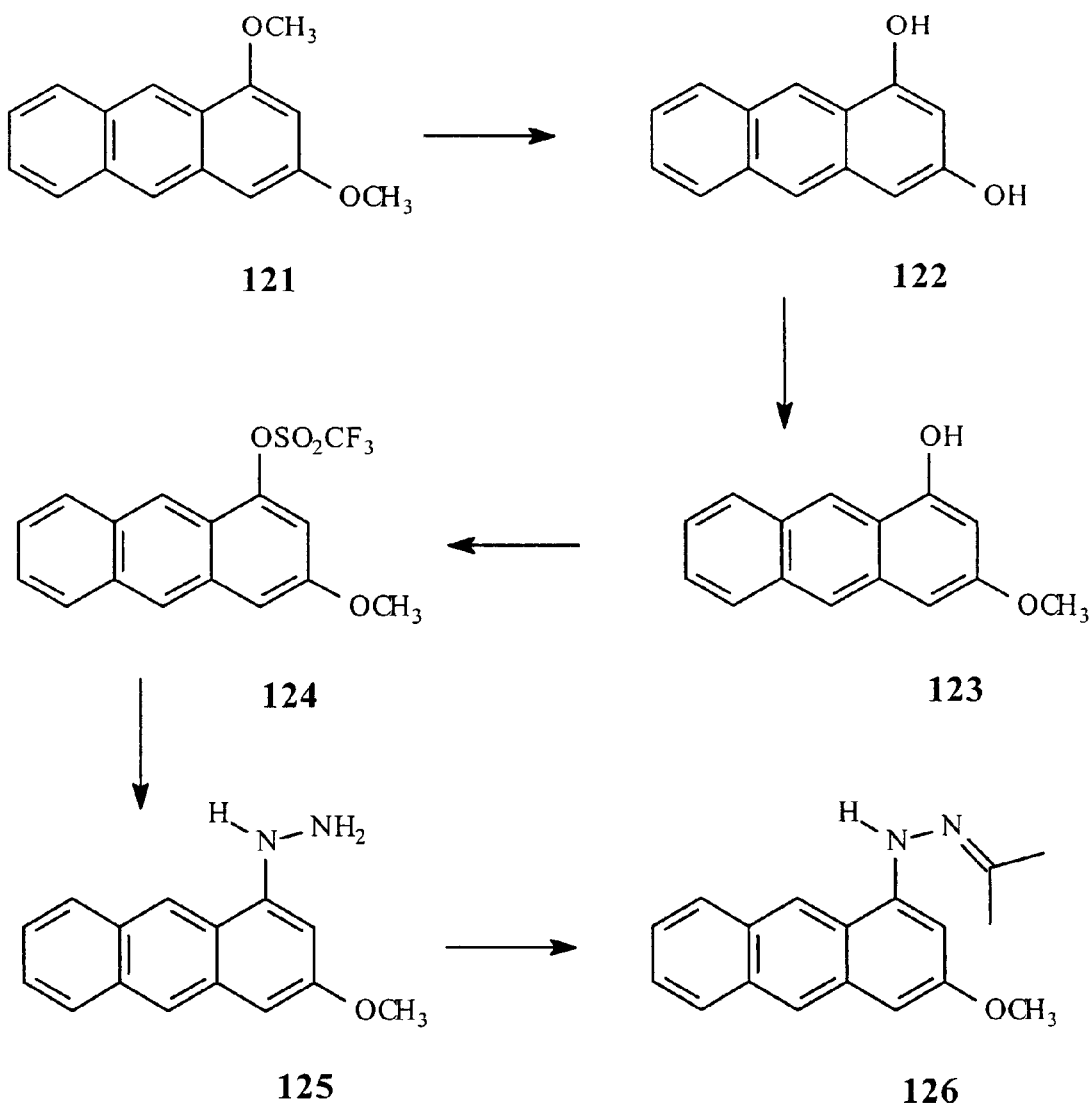
FIG. 17a shows a synthesis of compound 90.

A sixth general synthesis method suitable for the synthesis of aminoanthracene compounds is shown in FIG. 17a. In this method, aminoanthracene compound (methoxynaphthoindoline) 90 was prepared demethylating 1,3-dimethoxyanthracene 121, mono-methylating one of the hydroxyls to give 123, formation of the triflate 124, and displacement by hydrazine to give 125. Hydrazone formation with isobutyraldehyde, Fischer indoline cyclization and reduction with sodium cyanoborohydride gives 90 (Example 15).

Aminonaphthalene and aminoanthracene compounds can be sulfonated with sulfonating agents, such as chlorosulfonic acid. For example aminonaphthalene compound 86 is first nitrogen-protected as the N-sulfonamide compound 87 (FIG. 16, Example 14), then reacted with chlorosulfonic acid in acetic acid and dichloromethane at low temperature and deprotected to give sulfonated compound 89. Similarly, aminoanthracene compound 90 is protected as trifluoroacetylated compound 91, then sulfonated and deprotected to give 93 (FIG. 17b, Example 15). Intermediates 89 and 93 are useful in the synthesis of the sulfonated diarylrhodamine compounds.

V.3 Sulfonated Diarylrhodamine Dye Compounds

A novel class of sulfonated diarylrhodamine dye compounds are useful as molecular labels having the general structures shown as Formulas IIIabc below, including aryl- and nitrogen-substituted forms thereof.

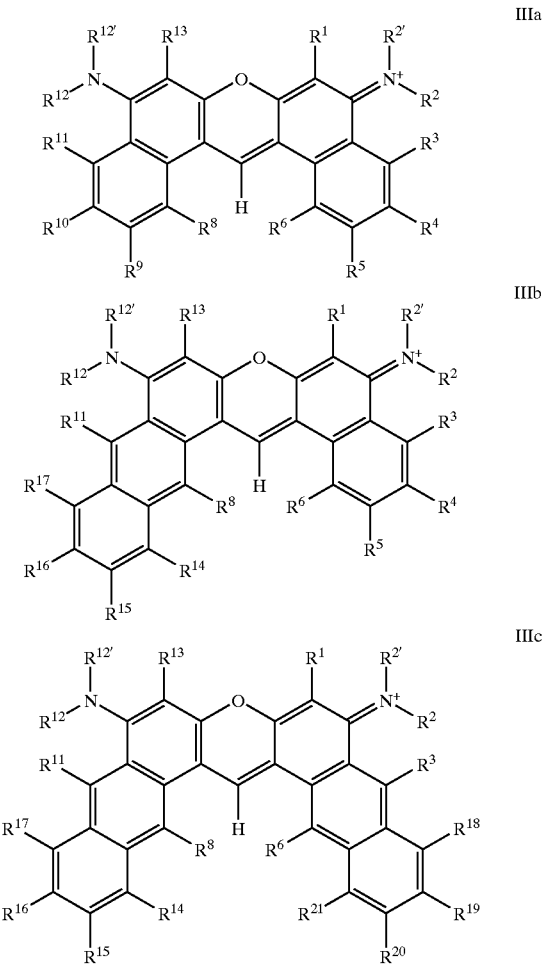

At least one aryl-substituent in Formula IIIabc is sulfonate. The presence of at least aryl-sulfonate group may confer unexpected and beneficial properties on diarylrhodamine compounds, such as modulated solubility, electrophoretic mobility, and spectral enhancements.

In one embodiment of the compounds of Formula IIIabc, the compound includes a first bridging group which when taken together with the C-12-bonded nitrogen and the C-12 and C-13 carbons forms a first ring structure having from 4 to 7 members, and/or a second bridging group which when taken together with the C-2-bonded-nitrogen and the C-1 and C-2 carbons forms a second ring structure having from 4 to 7 members. One or both of the first and second ring structures may have five members. In another embodiment, the five membered ring structure includes one gem disubstituted carbon, wherein the gem substituents are alkyl, e.g., methyl. In an alternative embodiment, the five membered ring is substituted with a linking moiety. In another embodiment, the five membered ring includes one or more nitrogen substituents, as described below. Exemplary sulfonated diarylrhodamine compounds with bridging ring structures include:

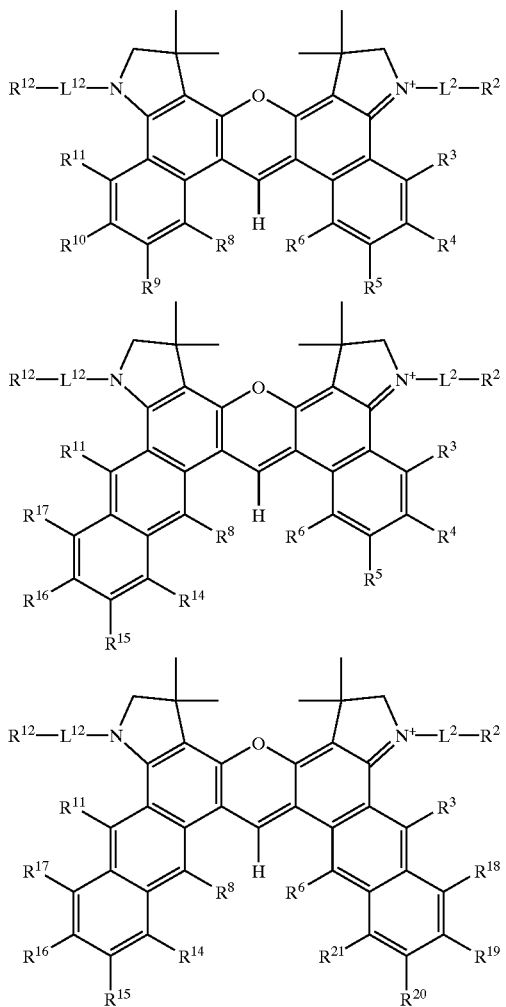

$L^2$ and $L^{12}$ are linkers including alkyldiyl, substituted phenyl, substituted benzyl, substituted biphenyl, and substituted naphthyl.

In yet another embodiment of the invention, the compounds of Formula IIIabc include one or more nitrogen substituents, $R^2$, $R^{2'}$, $R^{12}$, and $R^{12'}$. Such substituents are selected from the group consisting of alkyl, phenyl, aromatic, heterocycle, polycyclic aromatic, water-solubilizing group, linking moiety, and substituted forms thereof. Also, the nitrogen substituents may be alkyl, phenyl, polycyclic aromatic, or substituted forms thereof, where exemplary substituents include linking moiety, and water-solubilizing group.

In another embodiment of this second aspect of the invention, the compounds of Formula IIIabc include a third bridging group which when taken together with the C-12-bonded nitrogen and the C-11 and C-12 carbons forms a third ring structure having from 5 to 7 members, and/or a fourth bridging group which when taken together with the C-2-bonded nitrogen and the C-2 and C-3 carbons forms a fourth ring structure having from 5 to 7 members. One or both of the third and fourth ring structures may have six members. The six membered ring structure may include one gem disubstituted carbon, wherein the gem substituents are alkyl, e.g., methyl.

In another embodiment of the invention, the compounds of Formula IIIabc include aryl substituents at one or more of carbons C-1, C-3 through C-6, C-8 through C-11, and C-14 through C-21. Exemplary aryl substituents include but are not limited to hydrogen, fluorine, chlorine, alkyl, sulfate, sulfonate, sulfone, sulfonamide, sulfoxide, amino, ammonium, amido, nitrile, lower alkoxy, phenoxy, aromatic, phenyl, polycyclic aromatic, water-solubilizing group, heterocycle, and linking moiety, including substituted forms thereof. At least one aryl-substituent is sulfonate. In another embodiment, the compounds of Formula IIIabc include a fused aromatic ring bonded across the C-3 and C-4 carbons, the C-4 and C-5 carbons, the C-9 and C-10 carbons, or the C-10 and C-11 carbons, including substituted forms thereof. The fused aromatic ring may be bonded across the C-3 and C-4 carbons and the C-10 and C-11 carbons, or across the C-9 and C-10 carbons and the C-4 and C-5 carbons, including substituted forms thereof.

Several exemplary dye compounds according to this second aspect of the invention are shown in FIGS. 7 and 10–13, i.e., compounds 41–47 and 67, 72, 76 and 81; and in FIGS. 21, 22a, 22b, 22c, i.e. compounds 110–120 which have unexpected beneficial spectral properties. The extinction coefficient, quantum yield, and brightness are all increased in the sulfonated diarylrhodamine dye compounds 111, 114, 118, 119, 120 compared with their non-sulfonated analog diarylrhodamine dye compounds.

| | Aryl-sulfonated/Non-arylsulfonated | | |
|---|---|---|---|
| Compound | Extinction Coefficient Ratio | Quantum Yield Ratio | Brightness Increase |
| 111 | 1.16 | 1.29 | 1.5 |
| 114 | 2.3 | 0.88 | 2.02 |
| 118 | 1.26 | 1.38 | 1.74 |
| 119 | 1.53 | 1.8 | 2.75 |
| 120 | 1.91 | 3.13 | 5.98 |

All measurements were conducted in 8M urea and 1× Tris/EDTA buffer.

The table above measures the differences in the extinction coefficients, quantum yield, and brightness caused by the two aryl-sulfonate groups in the five exemplary dyes, relative to their non aryl-sulfonate analogs. The brightness increase is calculated by multiplying the extinction coefficient and the quantum yield.

Figure 4:
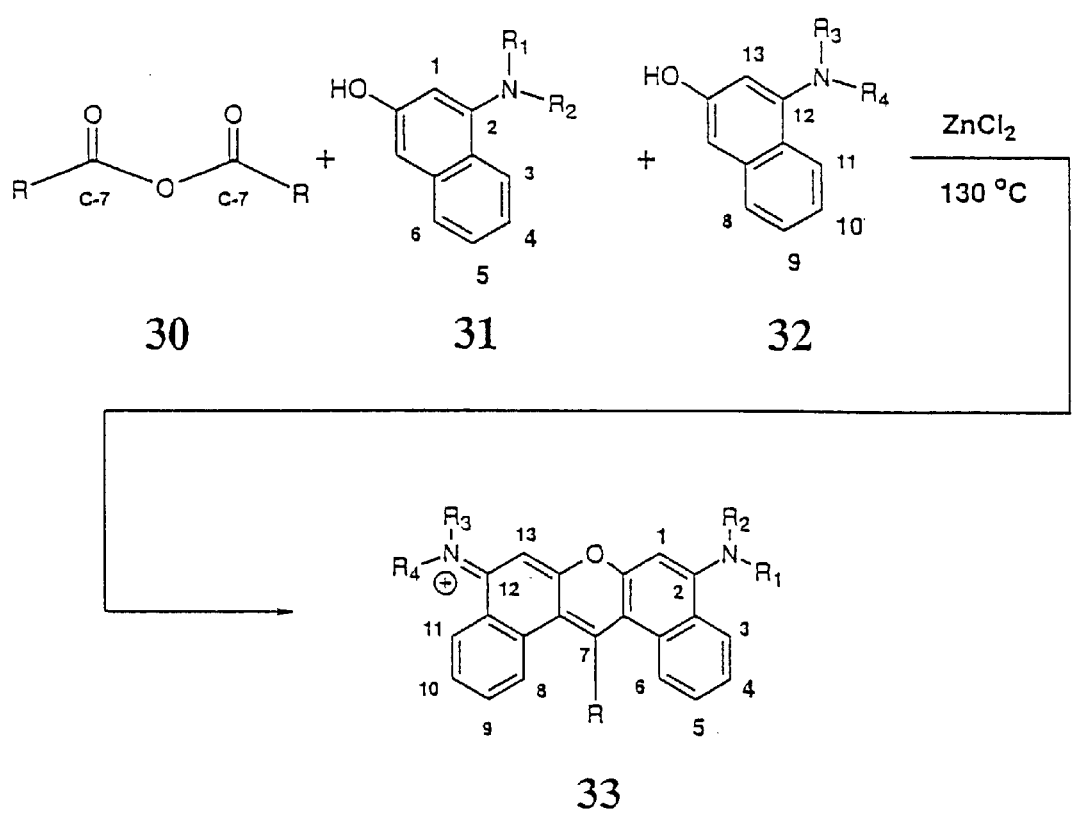
FIG. 4 shows a generalized synthetic pathway for the synthesis of the dibenzorhodamine dye compounds of the invention.
Figure 5:
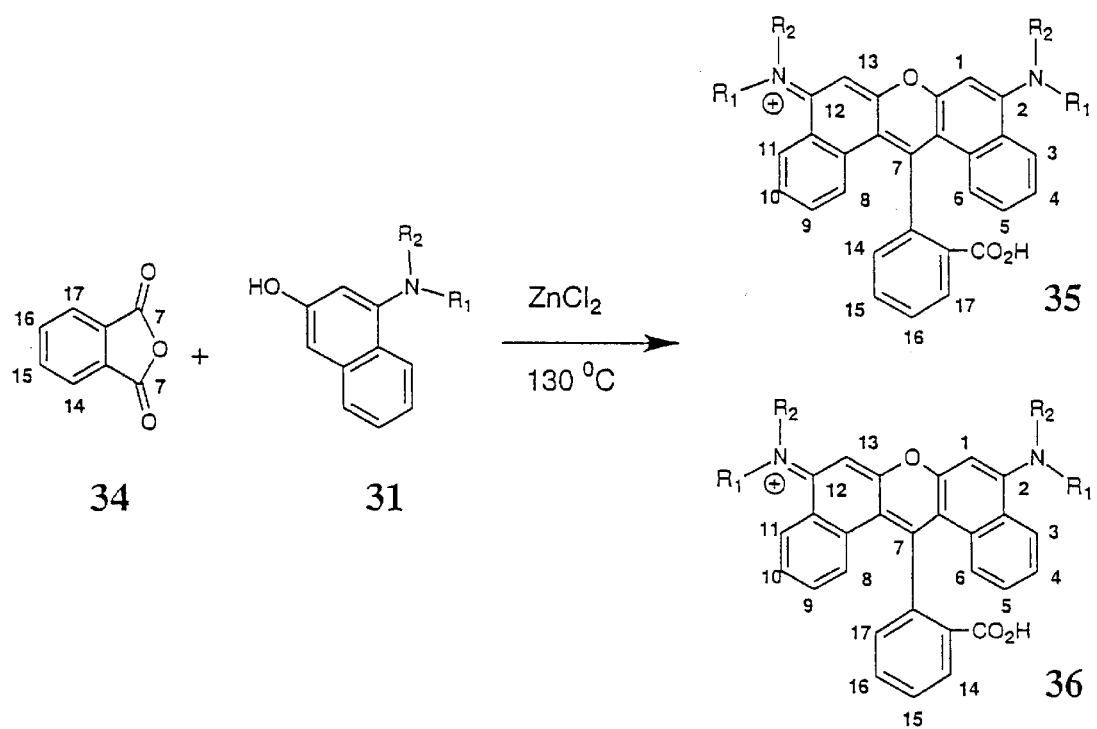
FIGS. 5 and 6 show exemplary synthetic pathways for the synthesis of the dibenzorhodamine dye compounds of the invention.

Generally, the sulfonated diarylrhodamine dyes of the present invention are synthesized as follows (FIG. 4): An anhydride derivative 30, e.g., a phthalic anhydride, is mixed with 1-amino-3-methoxy intermediates 31 and 32, and Lewis acid, e.g., $ZnCl_2$, where the R-substituents in compound 30 may be the same or different, but are preferably the same. Exemplary R-substituents include but are not limited to acetylene, alkyl, phenyl, heterocycle, and substituted forms thereof. The mixture is heated briefly until melting is observed. A solvent, e.g., 1,2-dichlorobenzene, is added to the reaction mixture, and the heterogeneous mixture is heated to about 130° C. to about 180° C. The crude reaction mixture is cooled and purified by normal phase flash chromatography to yield dye compound 33. When the anhydride is part of a substituted phthalic anhydride, e.g., compound 34, two isomers are formed (FIG. 5). The isomers 35 and 36 are separated by PTLC. The isomerically pure dyes are identified by single spots on normal and reverse phase TLC and by their UV/Visible absorption spectra and their long wavelength fluorescent excitation and emission spectra.

Figure 6:
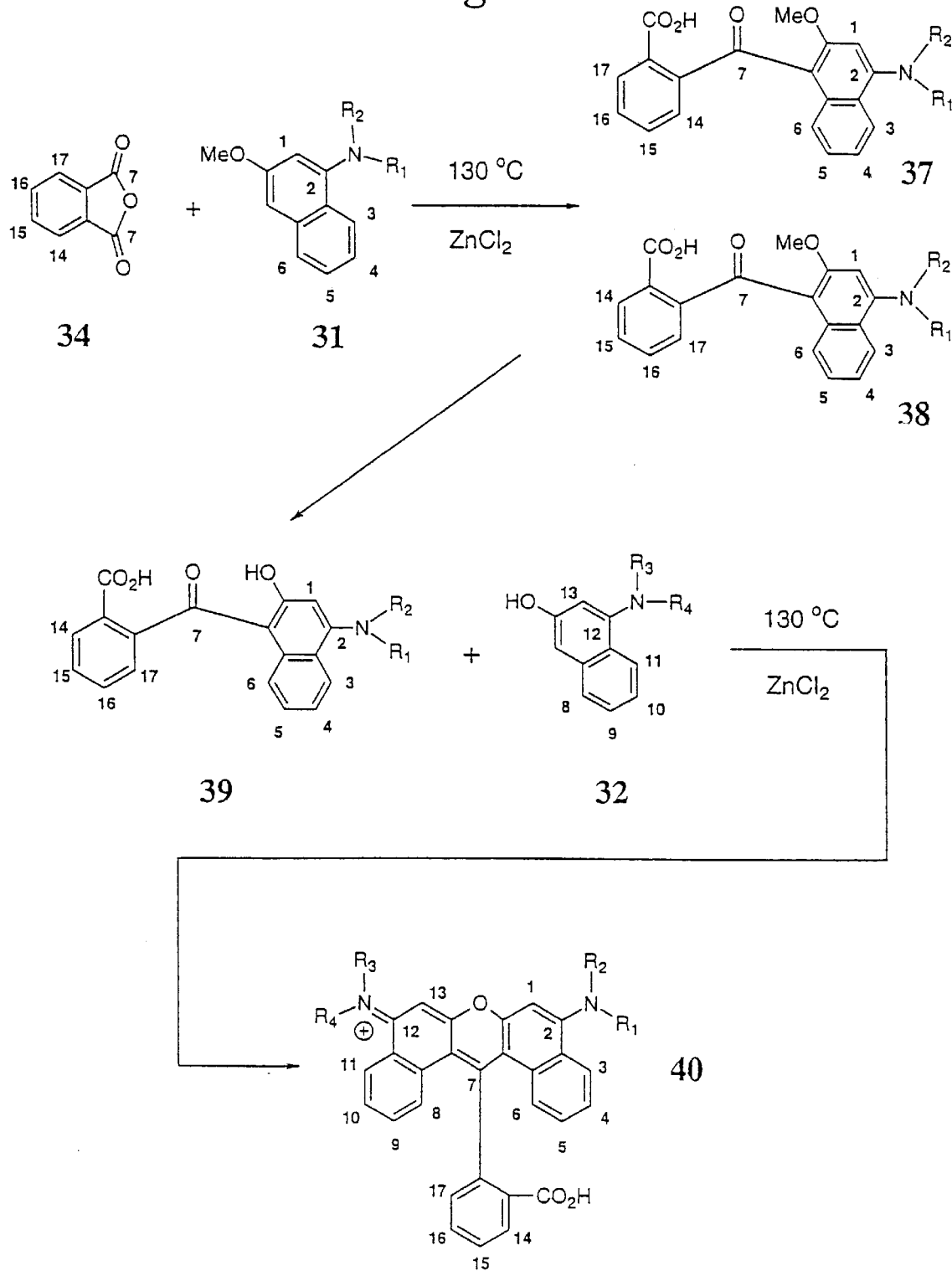

An alternative procedure for the synthesis of asymmetrical dye compounds is shown in FIG. 6. In this process, an anhydride derivative, e.g., phthalic anhydride 34, is mixed with dry nitrobenzene and heated. The mixture is cooled to room temperature and anhydrous AlCl$_3$ is added with stirring. Subsequently a 1-amino-3-methoxy intermediate 31 is added with stirring and the reaction is heated. The reaction is cooled and suspended in EtOAc. The organic layer is washed with saturated NH$_4$Cl, brine, dried over Na$_2$SO$_4$, filtered, and the solvent removed in vacuo. The resulting ketone intermediates 37/38 are purified and separated into distinct isomers 37 and 38 (except where substituents at C-14 and C-17 are the same and substituents at C15 and C-16 are the same) by flash chromatography or recrystallization. The methoxy group of the isomerically pure ketone intermediate 37 or 38 is removed according to a general boron tribromide deprotection procedure. Thus, compound 38 gives the amino-hydroxynaphthalene ketone intermediate 39. Amino-hydroxynaphthalene ketone intermediate 39 is then reacted with a 1-amino-3-methoxy intermediate 32. The reaction is cooled, giving isomerically pure and asymmetrically substituted product 40 that may be further purified by PTLC.

In another method for synthesizing the dibenzorhodamine dyes of the present invention and particularly suited to the synthesis of dyes not substituted at the C-7 position, i.e., pyronine dyes, the dyes are synthesized from hydroxybenzoindoline intermediates generated from O-protected N-substituted 3-hydroxybenzoindoline compounds following deprotection of the oxygen protecting group, e.g. methyl group deprotection by a demethylating reagent, e.g. aluminum chloride, and isolated by normal phase chromatographic purification. According to the synthesis, a hydroxybenzoindoline intermediate, corresponding to one half of a dye molecule, is first reacted with a formylating reagent, e.g. methylformanilide/POCl$_3$, and the ensuing formylated hydroxybenzoindoline intermediate is reacted directly with a different (or same) hydroxybenzoindoline intermediate, corresponding to the other half of the dye molecule. The reaction is run under acidic dehydrating conditions, e.g. POCl$_3$, and heat, e.g. 120–160° C. to give the crude carboxylic acid ester derivatized benzopyronine dye. In some cases, the methoxybenzoindoline intermediate is formylated prior to methyl group deprotection and then the methyl group of the formylated methoxyindoline derivative is deprotected to give the formylated hydroxybenzoindoline intermediate prior to reaction with the second equivalent of hydroxyindoline to give the pyronine dye. The pure dye is isolated after aqueous work-up and normal phase chromatography. The intermediate dye carboxylic acid ester is then hydrolysed with acid, i.e. HBr, to give the free acid dye derivatives after aqueous work-up and normal phase chromatography. N-phenyl substituted dyes may be subsequently sulfonated with a sulfonating agent, e.g., ClSO$_3$H to give a final dye derivative after aqueous work-up and normal phase chromatography.

V.4 Energy Transfer Dyes Incorporating the Sulfonated Diarylrhodamine Dyes

The present invention comprises energy transfer dye compounds incorporating the sulfonated diarylrhodamine dye compounds of Formula IIIabc. Generally, the energy transfer dyes of the present invention include a donor dye which absorbs light at a first wavelength and emits excitation energy in response, an acceptor dye which is capable of absorbing the excitation energy emitted by the donor dye and fluorescing at a second wavelength in response. The donor dye may be attached to the acceptor dye through a linker, the linker being effective to facilitate efficient energy transfer between the donor and acceptor dyes (Lee, "Energy-transfer dyes with enhanced fluorescence", U.S. Pat. No. 5,800,996; Lee "Energy-transfer dyes with enhanced fluorescence", U.S. Pat. No. 5,945,526; Mathies, "Fluorescent labels and their use in separations"; U.S. Pat. No. 5,654,419; Lee (1997) Nucleic Acids Res. 25:2816–22). Alternatively, the donor dye and the acceptor dye may be labelled at different attachment sites on the substrate. For example, an oligonucleotide may be labelled with a donor dye at the 5' terminus and an acceptor dye at the 3' terminus. A polypeptide may be labelled with a donor dye at the carboxyl terminus and an acceptor dye at an internal cysteine or lysine sidechain (Komoriya, "Compositions for the detection of proteases in biological samples and methods of use thereof", U.S. Pat. No. 5,605,809). In the energy-transfer dye of the invention, at least one of the donor or acceptor dyes which label a substrate is a sulfonated diarylrhodamine dye compound. Other dyes comprising the energy-transfer dye may be any fluorescent moiety which undergoes the energy transfer process with a sulfonated diarylrhodamine dye compound, including a fluorescein, rhodol, and a rhodamine. Other dyes include classes of fluorescent dyes such as cyanine, phthalocyanine, squaraine, bodipy, benzophenoxazine, fluorescein, diarylrhodamine, or rhodamine.

Energy-transfer dyes have advantages for use in the simultaneous detection of multiple labelled substrates in a mixture, such as DNA sequencing. A single donor dye can be used in a set of energy-transfer dyes so that each dye has strong absorption at a common wavelength. By then varying the acceptor dye in the energy-transfer set, the acceptor dyes can be spectrally resolved by their respective emission maxima. Energy-transfer dyes also provide a larger effective Stokes shift than non-energy-transfer dyes. The Stokes shift is the difference between the excitation maximum, the wavelength at which the donor dye maximally absorbs light, and the emission maximum, the wavelength at which the acceptor maximally emits light.

Generally the linker between the donor dye and acceptor dye has the structures:

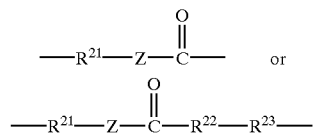

wherein Z is selected from the group consisting of NH, S and O; $R^{21}$ is a $C_1$–$C_{12}$ alkyl attached to the donor dye; $R^{22}$ is a substituent selected from the group consisting of a $C_1$–$C_{12}$ alkyldiyl, a five and six membered ring having at least one unsaturated bond and a fused ring structure which is attached to the carbonyl carbon; and $R^{23}$ includes a functional group which attaches the linker to the acceptor dye. $R^{22}$ may be a five or six membered ring such as cyclopentene, cyclohexene, cyclopentadiene, cyclohexadiene, furan, thiofuran, pyrrole, isopyrrole, isoazole, pyrazole, isoimidazole, pyran, pyrone, benzene, pyridine, pyridazine, pyrimidine, pyrazine, oxazine, indene, benzofuran, thionaphthene, indole and naphthalene. Specifically, the linker may have the structure:

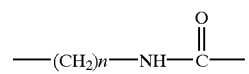

where n ranges from 2 to 10.

Generally also, $R^{23}$ may have the structure:

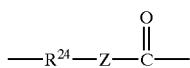

wherein $R^{24}$ is a $C_1$–$C_{12}$.

In one embodiment, the linker between the donor dye and acceptor dye includes a functional group which gives the linker some degree of structural rigidity, such as an alkene, diene, an alkyne, a five and six membered ring having at least one unsaturated bond or a fused ring structure (U.S. Pat. Nos. 5,821,356; 5,770,716; 5,948,648; 6,096,875). The donor dye and the acceptor dye of the energy-transfer dye may be attached by linkers which have the exemplary structures:

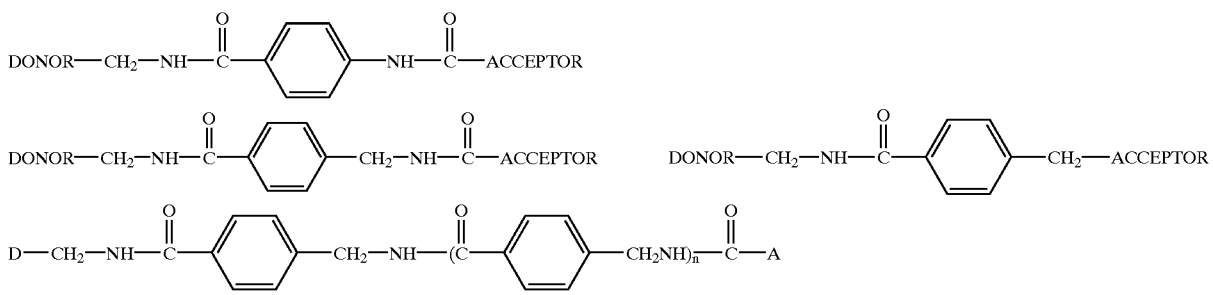

wherein D is a donor dye, A is an acceptor dye and n is 1 or 2. The phenyl rings may be substituted with groups such as sulfonate, phosphonate, and other charged groups.

The attachment sites of the linker between the donor dye and acceptor dye of an energy-transfer dye may be at any position where one or both of the donor dye and acceptor dye is a compound of the present invention. Exemplary attachment sites include $R^2$, $R^{2'}$, $R^{12}$ and $R^{12'}$.

The energy-transfer dye compound is covalently attached to a substrate through a linker. The linker may be a bond, $C_1$–$C_{12}$ alkyldiyl or $C_6$–$C_{20}$ aryldiyl. The linker may bear functional groups including amide, carbamate, urea, thiourea, phosphate, phosphonate, sulfonate, phosphorothioate, and the like. Exemplary linkers include 1,2-ethyldiyl and 1,6-hexyldiyl. The attachment sites of the linker between the energy-transfer dye and the substrate may be at any position on the energy-transfer dye, where one or both of the donor dye and acceptor dye is a sulfonate diarylrhodamine dye of the present invention. Where the substrate is a nucleoside or nucleotide, one attachment site to the energy-transfer dye is on the nucleobase. If the nucleobase is a purine, the linker may be attached at the 8-position. If the nucleobase is a 7-deazapurine, the linker may be attached at the 7-position or 8-position. If the nucleobase is a pyrimidine, the linker may be attached at the 5-position. Where the substrate is an oligonucleotide, attachment sites include the 3' and 5' terminii. Other oligonucleotide attachment sites include the internucleotide phosphate or phosphate-analog linkage, or at a position on the sugar, e.g. 2' or 4'. Where the substrate is a polypeptide (peptide or protein), attachment sites include the amino and carboxyl termini, and lysine residue amino groups.

V.5 Methods of Labelling

The present invention comprises labelling reagents wherein sulfonated diarylrhodamine compounds are in reactive form, i.e. with a linking moiety, to react with substrates. The present invention also includes substrates labelled, i.e. conjugated, with the compounds of the invention, Formula IIIabc. Substrates can be virtually any molecule or substance to which the dyes of the invention can be conjugated, including by way of example and not limitation, a polynucleotide, a nucleotide, a nucleoside, a polypeptide, a carbohydrate, a ligand, a substantially enantiomerically pure compound, a particle, a surface, a lipid, a solid support, organic and inorganic polymers, and combinations and assemblages thereof, such as chromosomes, nuclei, living cells (e.g., bacteria or other microorganisms, mammalian cells, tissues, etc.), and the like. A particle may include a nanoparticle, a microsphere, a bead, or a liposome. A surface may be glass or other non-porous planar material. The compounds of the invention are conjugated with the substrate via an optional linker by a variety of means, including hydrophobic attraction, ionic attraction, and covalent attachment.

Labelling typically results from mixing a sulfonated diarylrhodamine bearing a linking moiety, a substrate, and a suitable solvent, using conjugation methods well-known in the art (Hermanson, *Bioconjugate Techniques*, (1996) Academic Press, San Diego, Calif. pp. 40–55, 643–71), followed by separation of the labelled substrate, conjugate, from any unconjugated starting materials or unwanted by-products. The conjugate can be stored dry or in solution for later use.

The sulfonated diarylrhodamine may include a linking moiety at one of the substituent positions. A linking moiety is typically an electrophilic functional group, capable of forming a covalent bond by reacting with nucleophilic functionality on a substrate. Nucleophilic functionality may include, for example, alcohols, alkoxides, amines, hydroxylamines, and thiols. Alternatively, a linking moiety may include nucleophilic functionality that reacts with an electrophilic group on a substrate. Examples of linking moieties include azido, monosubstituted primary amine, disubstituted secondary amine, thiol, hydroxyl, halide, epoxide, N-hydroxysuccinimidyl ester, carboxyl, isothiocyanate, sulfonyl chloride, sulfonate ester, silyl halide, chlorotriazinyl, succinimidyl ester, pentafluorophenyl ester, maleimide, haloacetyl, epoxide, alkylhalide, allyl halide, aldehyde, ketone, acylazide, anhydride, iodoacetamide and an activated ester.

Figure 14:
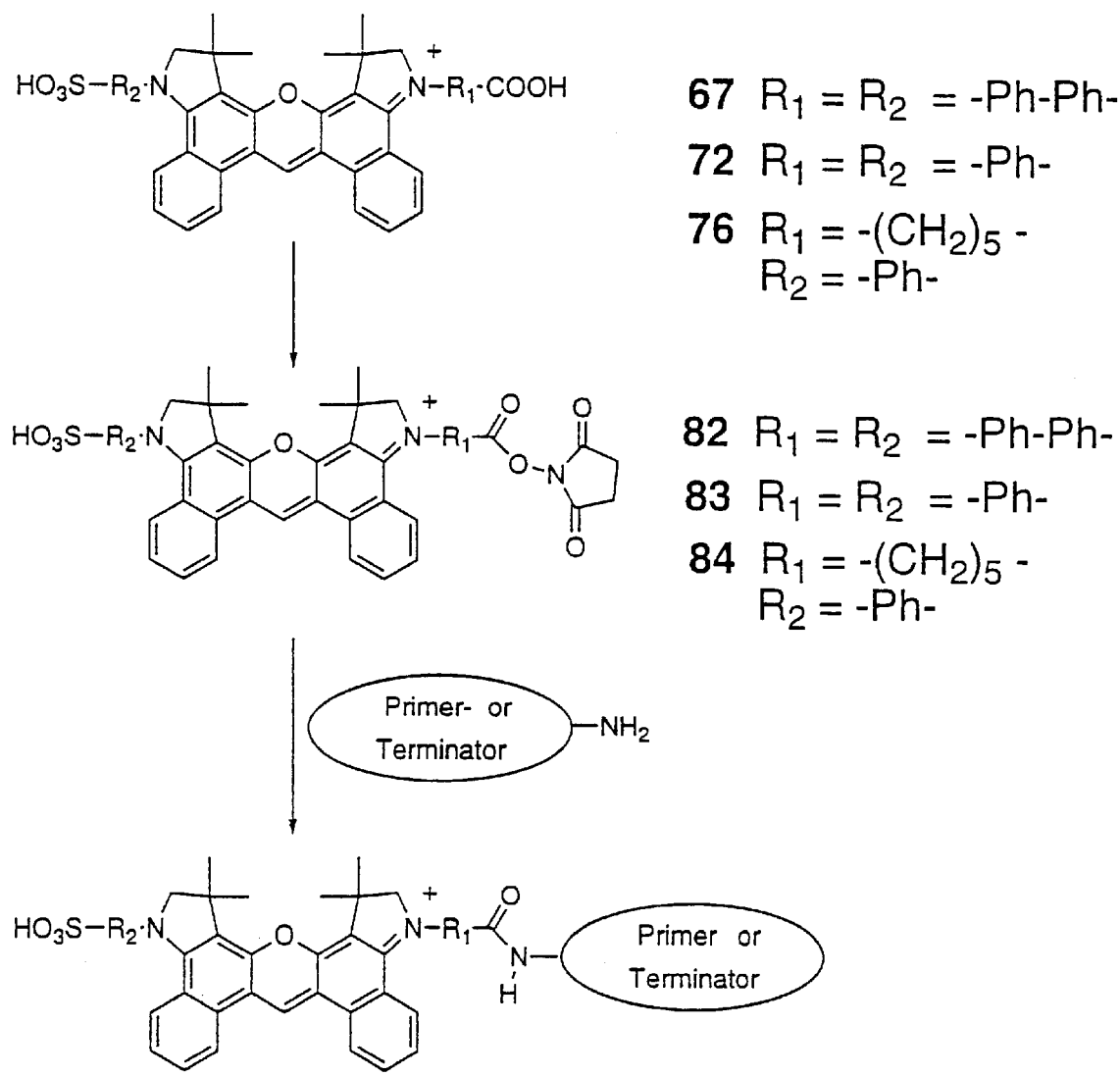
FIG. 14 shows a synthesis of compounds 82–84.

One linking moiety is N-hydroxysuccinimidyl ester (NHS) of a carboxyl group substituent of the sulfonated diarylrhodamine compound (FIG. 14). The NHS ester form of the compound is a labelling reagent. The NHS ester of the dye may be preformed, isolated, purified, and/or characterized, or it may be formed in situ and reacted with a nucleophilic group of a substrate, such as an oligonucleotide, a nucleoside, a nucleotide, a polypeptide, or the like (Brinkley, M. (1992) Bioconjugate Chem. 3:2–13). Typically, the carboxyl form of the dye is activated by reacting with some combination of: (1) a carbodiimide reagent, e.g. DCC (dicyclohexylcarbodiimide), DIPCDI (diisopropylcarbodiimide), or a uronium reagent, e.g. TSTU (O-(N-Succinimidyl)-N,N,N', N'-tetramethyluronium tetrafluoroborate, HBTU (O-benzotriazol-1-yl)-N,N,N',N'-tetramethyluronium hexafluorophosphate), HATU (O-(7-azabenzotriazol-1-yl)-N,N,N',N'-tetramethyluronium hexafluorophosphate); (2) an activator, such as 1-hydroxybenzotriazole (HOBt); and (3) N-hydroxysuccinimide to give the NHS ester of the dye, e.g. compounds 82, 83, 84 in FIG. 14 and 85 in FIG. 15.

In some cases, the sulfonated diarylrhodamine compound and the substrate may be coupled by in situ activation of the compound and reaction with the substrate to form the sulfonated diarylrhodamine-substrate conjugate in one step. Other activating and coupling reagents include TBTU (2-(1H-benzotriazo-1-yl)-1-1,3,3-tetramethyluronium hexafluorophosphate), TFFH (N,N',N",N'"-tetramethyluronium 2-fluoro-hexafluorophosphate), PyBOP (benzotriazole-1-yl-oxy-tris-pyrrolidino-phosphonium hexafluorophosphate, EEDQ (2-ethoxy-1-ethoxycarbonyl-1,2-dihydro-quinoline), DCC, DIPCDI, MSNT (1-(mesitylene-2-sulfonyl)-3-nitro-1H-1,2,4-triazole, and aryl sulfonyl halides, e.g. triisopropylbenzenesulfonyl chloride.

Another reactive linking group is a phosphoramidite form of sulfonated diarylrhodamine compounds. Phosphoramidite dye reagents are particularly useful for the automated synthesis of oligonucleotides labelled with the dyes of the invention. Most conveniently, phosphoramidite dye reagents may be coupled to oligonucleotides bound to a solid support during the normal course of solid-phase synthesis. Oligonucleotides are commonly synthesized on solid supports by the phosphoramidite method (Caruthers, M. and Beaucage, S. "Phosphoramidite compounds and processes", U.S. Pat. No. 4,415,732; Caruthers, M. and Matteucci, M. "Process for preparing polynucleotides", U.S. Pat. No. 4,458,066; Beaucage, S. and Iyer, R. (1992) "Advances in the synthesis of oligonucleotides by the phosphoramidite approach", Tetrahedron 48:2223–2311).

Phosphoramidite sulfonated diarylrhodamine reagents can be nucleosidic or non-nucleosidic. Non-nucleosidic forms of the phosphoramidite reagents have the general Formula IV:

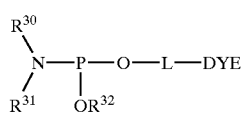

IV where DYE is a protected or unprotected form of sulfonated diarylrhodamine IIIabc, including energy-transfer dye. L is a linker. $R^{30}$ and $R^{31}$ taken separately are $C_1$–$C_{12}$ alkyl, $C_4$–$C_{10}$ aryl) and cycloalkyl containing up to 10 carbon atoms, or $R^{30}$ and $R^{31}$ taken together with the phosphoramidite nitrogen atom may form a saturated nitrogen heterocycle. $R^{32}$ is a phosphite ester protecting group which prevents unwanted extension of the oligonucleotide. Generally, $R^{32}$ is stable to oligonucleotide synthesis conditions yet is able to be removed from a synthetic oligonucleotide product with a reagent that does not adversely affect the integrity of the oligonucleotide or the dye. $R^{32}$ may be: (i) methyl, (ii) 2-cyanoethyl; —$CH_2CH_2CN$, or (iii) 2-(4-nitrophenyl)ethyl; —$CH_2CH_2(p-NO_2Ph)$. Embodiments of phosphoramidite reagents include where: (i) $R^{30}$ and $R^{31}$ are each isopropyl, (ii) $R^{30}$ and $R^{31}$ taken together is morpholino, (iii) L is $C_1$–$C_{12}$ alkyl, (iv) $R^{32}$ is 2-cyanoethyl, and (v) DYE is attached at $R^{18}$ or $R^{19}$ by a linker. The linker, L, may alternatively be:

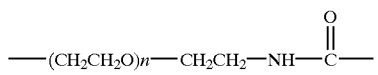

where n ranges from 1 to 10. An example of phosphoramidite reagent IV has the structure:

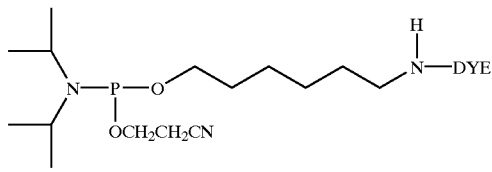

Phosphoramidite dye reagents IV effect labelling of a substrate with a sulfonated diarylrhodamine compound of the invention. Where the substrate is an oligonucleotide, the dye will be attached at the 5' terminus of the oligonucleotide, as a consequence of the typical 3' to 5' direction of synthesis, or at the 3' terminus of the oligonucleotide when the 5' to 3' direction synthesis method is practiced (Wagner (1997) Nucleosides & Nucleotides 16:1657–60). Reagent IV may be coupled to a polynucleotide which is bound to a solid support, e.g. through the 3' terminus. Other phosphoramidite dye reagents, nucleosidic and non-nucleosidic, allow for labelling at other sites of an oligonucleotide, e.g. 3' terminus, nucleobase, internucleotide linkage, sugar. Labelling at the nucleobase, internucleotide linkage, and sugar sites allows for internal and multiple labelling with fluorescent dyes.

A sulfonated diarylrhodamine compound of the invention may be converted to a non-nucleosidic, phosphoramidite labelling reagent by any known method of phosphitylation of nucleophilic functionality with trivalent phosphitylating reagents. For example, when the compound contains a carboxyl group, e.g. 110–120, the carboxyl may be activated, e.g. to the NHS, and amidated with 6-amino-1-hexanol. The resulting hydroxyl may be phosphitylated with bis(diisopropylamino)cyanoethylphosphite or chloro-diisopropylamino-cyanoethylphosphine to give the phosphoramidite dye-labelling reagent IV (Theisen (1992) "Fluorescent dye phosphoramidite labelling of oligonucleotides", in Nucleic Acid Symposium Series No. 27, Oxford University Press, Oxford, pp. 99–100). Alternatively, the carboxyl group of the compound may be reduced to the hydroxyl, to be phosphitylated.

The phosphoramidite reagent IV reacts with a hydroxyl group, e.g. 5' terminal OH of an oligonucleotide bound to a solid support, under mild acid activation, to form an internucleotide phosphite group which is then oxidized to an internucleotide phosphate group. In some instances, the sulfonated diarylrhodamine compound may contain functional groups that require protection either during the synthesis of the phosphoramidite reagent or during its subsequent use to label molecules such as oligonucleotides. The protecting group(s) used will depend upon the nature of the functional groups, and will be apparent to those having skill in the art (Greene, T. and Wuts, P. Protective Groups in Organic Synthesis, 2nd Ed., John Wiley & Sons, New York, 1991). Generally, the protecting groups used should be stable under the acidic conditions (e.g. trichloroacetic acid, dichloroacetic acid) commonly employed in oligonucleotide synthesis to remove 5'-hydroxyl protecting groups (e.g., dimethoxytrityl) and labile under the basic conditions (ammonium hydroxide, aqueous methylamine) used to deprotect and/or cleave synthetic oligonucleotides from solid supports.

Polypeptides, antibodies, and other biopolymers comprised of amino acids and amino acid analogs may be covalently labelled by conjugation with the sulfonated diarylrhodamine compounds of the invention. Typically, the compound is in electrophilic form, e.g. NHS reactive linking group, which reacts with a nucleophilic group of the peptide, e.g. amino terminus, or amino side chain of an amino acid such as lysine. Alternatively, the dye may be in nucleophilic form, e.g. amino- or thiol-reactive linking group, which may react with an electrophilic group of the peptide, e.g. NHS of the carboxyl terminus or carboxyl side chain of an amino acid. Labelled polypeptides preferably retain their specific binding and recognition properties in interacting with cell surface and intracellular components. The sulfonated diarylrhodamine compound, acting as a dye, provides a detection element for localizing, visualizing, and quantitating the binding or recognition event. Polypeptides can also be labelled with two moieties, a fluorescent reporter and quencher, which together undergo fluorescence resonance energy transfer (FRET). The fluorescent reporter may be partially or significantly quenched by the quencher moiety in an intact polypeptide. Upon cleavage of the polypeptide by a peptidase or protease, a detectable increase in fluorescence may be measured (Knight, C. (1995) "Fluorimetric Assays of Proteolytic Enzymes", Methods in Enzymology, Academic Press, 248:18–34).

V.6 Labelled Nucleotides

One class of labelled substrates include conjugates of nucleosides and nucleotides that are labelled with the sulfonated diarylrhodamine compounds of the invention. Such labelled nucleosides and nucleotides are particularly useful for labelling polynucleotides formed by enzymatic synthesis, e.g., labelled nucleotide 5'-triphosphates used in the context of PCR amplification, Sanger-type polynucleotide sequencing, and nick-translation reactions.

Nucleosides and nucleotides can be labelled at sites on the sugar or nucleobase moieties. Nucleobase labelling sites include the 8-C of a purine nucleobase, the C-7 or C-8 of a 7-deazapurine nucleobase, and the 5-position of a pyrimidine nucleobase. Between a nucleoside or nucleotide and a dye, a linker may attach to a sulfonated diarylrhodamine compound at any position.

The labelled nucleoside or nucleotide may be enzymatically incorporatable and enzymatically extendable. Nucleosides or nucleotides labelled with compounds of the invention may have formula V:

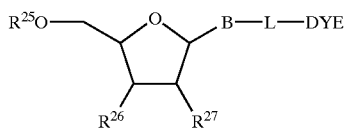

V where DYE is a protected or unprotected form of compounds IIIabc, including energy-transfer dye. B may be any nucleobase, e.g. uracil, thymine, cytosine, adenine, 7-deazaadenine, guanine, and 8-deazaguanosine. $R^{25}$ is H, monophosphate, diphosphate, triphosphate, thiophosphate, or phosphate ester analog. $R^{26}$ and $R^{27}$, when taken alone, are each independently H, HO, F and a phosphoramidite. Where $R^{26}$ or $R^{27}$ is phosphoramidite, $R^{25}$ is an acid-cleavable hydroxyl protecting group, e.g. dimethoxytrityl, which allows subsequent monomer coupling under automated synthesis conditions (U.S. Pat. Nos. 4,415,732 and 4,458,066; Beaucage, S. and Iyer, R. (1992) "Advances in the synthesis of oligonucleotides by the phosphoramidite approach", Tetrahedron 48:2223–2311).

Where the labelled nucleoside or nucleotide is a terminator, $R^{26}$ and $R^{27}$ are selected to block polymerase-mediated template-directed polymerization. In terminator nucleotides, $R^{26}$ and $R^{27}$, when taken alone, are each independently H, F, and a moiety which blocks polymerase-mediated template-directed polymerization, or when taken together form 2'-3'-didehydroribose. In formula V, when both $R^{26}$ and $R^{27}$ are hydroxyl, the resultant compounds are labelled ribonucleosides and ribonucleotides (NTP). When $R^{27}$ is hydrogen and $R^{26}$ is hydroxyl, the resultant compounds are labelled 2'-deoxyribonucleosides and nucleotides (dNTP). When $R^{26}$ and $R^{27}$ are each hydrogen, the resultant compounds are 2',3'-dideoxyribonucleosides and nucleotides (ddNTP). Labelled ddNTP find particular use as terminators in Sanger-type DNA sequencing methods utilizing fluorescent detection. Labelled 2'-deoxyribonucleoside-5'-triphosphates (dNTP) find particular use as reagents for labelling DNA polymerase extension products, e.g., in the polymerase chain reaction or nick-translation. Labelled ribonucleoside-5'-triphosphates (NTP) find particular use as reagents for labelling RNA polymerase extension products.

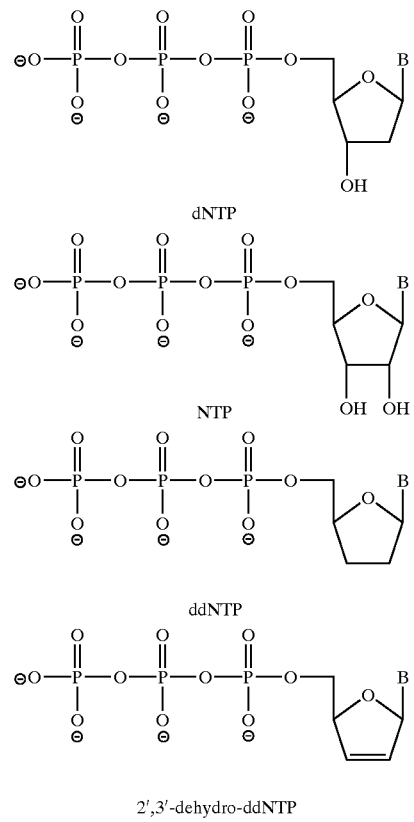

2',3'-dehydro-ddNTP

Alkynylamino-linked compounds V, where L includes an alkyndiyl group, are useful for conjugating sulfonated diarylrhodamine compounds to nucleosides, nucleotides and analogs therein. Their synthesis is taught in EP 87305844.0 and Hobbs, (1989) J. Org. Chem. 54:3420. The corresponding nucleoside mono-, di- and triphosphates are obtained by standard techniques (for example, the methods described in U.S. Pat. Nos. 5,821,356; 5,770,716; 5,948,648; 6,096,875). Methods for synthesizing compounds V with modified propargylethoxyamido linkers L can also be found in these patents. Additional synthesis procedures suitable for use in synthesizing compounds according to structural formula V are described, for example, in Gibson (1987) Nucl. Acids Res. 15:6455–6467; Gebeyehu (1987) Nucl. Acids Res. 15:4513–4535; Haralambidis (1987) Nucl. Acids Res. 15:4856–4876; Nelson (1986) Nucleosides and Nucleotides. 5(3):233–241; Bergstrom (1989) J. Am. Chem. Soc. 111:374–375; U.S. Pat. Nos. 4,855,225; 5,231,191 and 5,449,767, which are incorporated herein by reference. Any of these methods can be routinely adapted or modified as necessary to synthesize the full range of labelled nucleosides, nucleotides, and analogs described herein.

One embodiment of the alkynyl linker L may be:

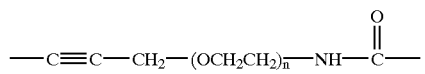

wherein is 0, 1, or 2.

Energy-transfer dye pairs can be conjugated to a nucleotide 5'-triphosphate by linking through a nucleobase amino group to: (i) an activated ester of a energy-transfer dye pair, or (ii) stepwise coupling to one dye, e.g. $R^{11}$-protected aminomethyl, $R^{18}$-carboxyl fluorescein, then coupling the unprotected $R^{11}$-aminomethyl to the second dye of the pair.

Alternative synthetic routes to energy-transfer nucleotides and polynucleotides, with different convergent schemes may be practiced. The substrate, dye, and linker subunits, or synthons, may be assembled for coupling in any order. For example, the energy-transfer pair of donor dye and acceptor dye may be covalently attached through a linker and then coupled to the nucleotide or polynucleotide. Many different synthetic routes can be practiced which result in the labelling of nucleotides with the dyes of the invention. Reactive functionality, such as carboxylic acid, amino, hydroxyl groups, may require protection, utilizing the vast art of organic synthesis methodology.

V.7 Labelled Oligonucleotides

Oligonucleotides are commonly synthesized on solid supports by the phosphoramidite method (U.S. Pat. Nos. 4,415,732; 4,973,679; 4,458,066; Beaucage, S. and Iyer, R. (1 992) Tetrahedron 48:2223–2311) using commercially available phosphoramidite nucleosides, supports e.g. silica, controlled-pore-glass (U.S. Pat. No. 4,458,066) and polystyrene (U.S. Pat. Nos. 5,047,524 and 5,262,530) and automated synthesizers (Models 392, 394, 3948 DNA/RNA Synthesizers, Applied Biosystems).

Another class of labelled substrates includes conjugates of oligonucleotides and the compounds of the invention. Such conjugates may find utility as DNA sequencing primers, PCR primers, oligonucleotide hybridization probes, oligonucleotide ligation probes, double-labelled 5'-exonuclease (TaqMan™) probes, size standards for electrophoresis, i.e. "lane standards" or "lane markers", and the like (Fung, U.S. Pat. No. 4,757,141; Andrus, "Chemical methods for 5' non-isotopic labelling of PCR probes and primers" (1995) in PCR 2. *A Practical Approach*, Oxford University Press, Oxford, pp. 39–54; Hermanson, *Bioconjugate Techniques*, (1996) Academic Press, San Diego, Calif. pp. 40–55, 643–71; Mullah (1998) "Efficient synthesis of double dye-labelled oligodeoxyribonucleotide probes and their application in a real time PCR assay", Nucl. Acids Res. 26:1026–1031). A labelled oligonucleotide may have formula VI:

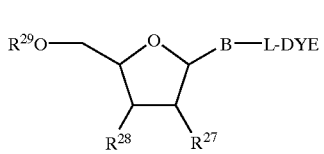

where the oligonucleotide comprises 2 to 1000 nucleotides. DYE is a protected or unprotected form of compounds I or II, including energy-transfer dye. B is any nucleobase, e.g. uracil, thymine, cytosine, adenine, 7-deazaadenine, guanine, and 8-deazaguanosine. L is a linker. $R^{27}$ is H, OH, halide, azide, amine, $C_1$–$C_6$ aminoalkyl, $C_1$–$C_6$ alkyl, allyl, $C_1$–$C_6$ alkoxy, $OCH_3$, or $OCH_2CH=CH_2$. $R^{22}$ is H, phosphate, internucleotide phosphodiester, or internucleotide analog. $R^{29}$ is H, phosphate, internucleotide phosphodiester, or internucleotide analog. In this embodiment, the nucleobase-labelled oligonucleotide VI may bear multiple dyes of the invention attached through the nucleobases. Nucleobase-labelled oligonucleotide VI may be formed by: (i) enzymatic incorporation of enzymatically incorporatable nucleotide reagents V where $R^{25}$ is triphosphate, by a DNA polymerase or ligase, and (ii) coupling of a nucleoside phosphoramidite reagent by automated synthesis. Whereas, nucleobase-labelled oligonucleotides VI may be multiply labelled by incorporation of more than one incorporatable nucleotide V, labelling with a dye label reagent such as IV leads to singly 5'-labelled oligonucleotides, according to formula VII:

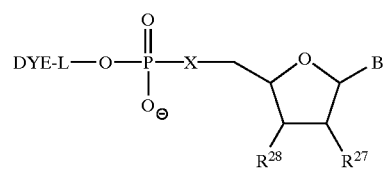

where X is O, NH, or S; $R^{27}$ is H, OH, halide, azide, amine, $C_1$–$C_6$ aminoalkyl, $C_1$–$C_6$alkyl, allyl, $C_1$–$C_6$ alkoxy, $OCH_3$, or $OCH_2CH=CH_2$; $R^{28}$ is H, phosphate, internucleotide phosphodiester, or internucleotide analog; and L is $C_1$–$C_{12}$ alkyl, aryl, or polyethyleneoxy of up to 100 ethyleneoxy units.

The linker L in formulas VI or VII may be attached at any site on the sulfonated diarylrhodamine compound IIIabc of the invention, DYE.

In a first method for labelling synthetic oligonucleotides, a nucleophilic functionality, e.g. a primary aliphatic amine, is introduced at a labelling attachment site on an oligonucleotide, e.g. a 5' terminus. After automated, solid-support synthesis is complete, the oligonucleotide is cleaved from the support and all protecting groups are removed. The nucleophile-oligonucleotide is reacted with an excess of a label reagent containing an electrophilic moiety, e.g. isothiocyanate or activated ester, e.g. N-hydroxysuccinimide (NHS), under homogeneous solution conditions (Hermanson, *Bioconjugate Techniques*, (1996) Academic Press, San Diego, Calif. pp. 40–55, 643–71; Andrus, A. "Chemical methods for 5' non-isotopic labelling of PCR probes and primers" (1995) in PCR 2. *A Practical Approach*, Oxford University Press, Oxford, pp. 39–54). Labelled oligonucleotides VII may be formed by reacting a reactive linking group form, e.g. NHS, of a dye, with a 5'-aminoalkyl oligonucleotide (U.S. Pat. No. 4,757,141).

In a second method, a label is directly incorporated into the oligonucleotide during or prior to automated synthesis, for example as a support reagent (Mullah, "Solid support reagents for the direct synthesis of 3'-labelled polynucleotides", U.S. Pat. No. 5,736,626; Nelson, "Multifunctional controlled pore glass reagent for solid phase oligonucleotide synthesis", U.S. Pat. No. 5,141,813) or as a phosphoramidite reagent IV. Certain fluorescent dyes and other labels have been functionalized as phosphoramidite reagents for 5' labelling (Theisen (1992) *Nucleic Acid Symposium Series* No. 27, Oxford University Press, Oxford, pp. 99–100).

Generally, if the labelled oligonucleotide is made by enzymatic synthesis, the following procedure may be used. A target DNA is denatured and an oligonucleotide primer is annealed to the template DNA. A mixture of enzymatically-incorporatable nucleotides or nucleotide analogs capable of supporting continuous template-directed enzymatic extension of the primed target (e.g., a mixture including dGTP, dATP, dCTP and dTTP or dUTP) is added to the primed target. At least a fraction of the nucleotides are labelled terminators V, e.g. ddNTP or 3'F-dNTP, labelled with a sulfonated diarylrhodamine dye IIIabc. A polymerase enzyme is next added to the mixture under conditions where the polymerase enzyme is active. A labelled oligonucleotide is formed by the incorporation of the labelled nucleotides or terminators during polymerase-mediated strand synthesis. In an alternative enzymatic synthesis method, two primers are used instead of one: one complementary to the (+) strand of the target and another complementary to the (−) strand of the target, the polymerase is a thermostable polymerase and the reaction temperature is cycled between a denaturation temperature and an extension temperature, thereby exponentially synthesizing a labelled complement to the target sequence by PCR (Innis (1990) *PCR Protocols*, Eds., Academic Press).

Polynucleotides labelled with the sulfonated diarylrhodamine compounds of the present invention may be additionally labelled with moieties that affect the rate of electrophoretic migration, i.e. mobility-modifying labels. Mobility-modifying labels include polyethyleneoxy units, —$(CH_2CH_2O)_n$— where n may be 1 to 100 (U.S. Pat. No. 5,624,800). Preferably, n is from 2 to 20. The polyethyleneoxy units may be interspersed with phosphate groups. Specifically labelling sulfonated diarylrhodamine-labelled polynucleotides with additional labels of polyethyleneoxy of discrete and known size allows for separation by electrophoresis, substantially independent of the number of nucleotides in the polynucleotide. That is, polynucleotides of the same length may be discriminated upon by the presence of spectrally resolvable dye labels and mobility-modifying labels. Polynucleotides bearing both dye labels and mobility-modifying labels may be formed enzymatically by ligation or polymerase extension of the single-labelled polynucleotide or nucleotide constituents.

V.8 Methods Utilizing the Sulfonated Diarylrhodamine Dyes

Methods requiring simultaneous detection of multiple spatially-overlapping analytes may benefit from sulfonated diarylrhodamine dyes as labels. The sulfonated diarylrhodamine compounds of the present invention are well suited for any method utilizing fluorescent detection, such as polymerase chain reaction (PCR) amplification, DNA sequencing, antisense transcriptional and translational control of gene expression, genetic analysis, and DNA probe-based diagnostic testing (Kricka, L. (1992) *Nonisotopic DNA Probe Techniques*, Academic Press, San Diego, pp.3–28). Fluorescence detection of fluorescent dye-labelled oligonucleotides is the basis for nucleic acid sequence detection assays such as 5' exonuclease assay (Livak, U.S. Pat. No. 5,723,591), FRET hybridization (Tyagi, S. and Kramer, F. (1996) "Molecular Beacons: Probes that fluoresce upon hybridization", Nature Biotechnology, 14:303–08), genetic linkage mapping (Dib (1996) "A comprehensive genetic map of the human genome based on 5,264 microsatellites", Nature 380:152–54) and oligonucleotide-ligation assay (Grossman (1994) "High-density multiplex detection of nucleic acid sequences: oligonucleotide ligation assay and sequence-coded separation", Nucl. Acids Res. 22:4527–34).

The present invention is particularly well suited for detecting classes of differently-labelled polynucleotides that have been subjected to a biochemical separation procedure, such as electrophoresis (Rickwood and Hames, Eds., *Gel Electrophoresis of Nucleic Acids: A Practical Approach*, IRL Press Limited, London, 1981). The electrophoretic matrix may be a sieving polymer, e.g. crosslinked or uncrosslinked polyacrylamide, or other amide-containing polymer, having a concentration (weight to volume) of between about 2–20 weight percent (Madabhushi, U.S. Pat. Nos. 5,552,028; 5,567,292; 5,916,426). The electrophoretic matrix may be configured in a slab gel or capillary format (Rosenblum, (1997) Nucleic Acids Res. 25:3925–29; Mathies, U.S. Pat. No. 5,274,240).

Subsequent to electrophoretic separation, the dye-polynucleotide conjugates may be detected by measuring the fluorescence emission from the dye labeled polynucleotides, e.g. by high intensity illumination mercury vapor lamps, lasers, or the like. The illumination means may be a laser having an illumination beam at a wavelength above about 600 nm. Also, the dye-polynucleotides may be illuminated by laser light generated by a He-Ne gas laser or a solid-state diode laser. The fluorescence is then detected by a light-sensitive detector, e.g., a photomultiplier tube, a charged coupled device, or the like. Exemplary electrophoresis detection systems are described elsewhere, e.g., U.S. Pat. Nos. 5,543,026; 5,274,240; 4,879,012; 5,091,652 and 4,811,218.

V.8A Primer Extension

In one category of methods referred to herein as "fragment analysis" or "genetic analysis" methods, polynucleotide fragments labelled with fluorescent dyes, including sulfonated diarylrhodamine compounds, are generated through template-directed enzymatic synthesis using labelled primers or nucleotides, e.g. by ligation or polymerase-directed primer extension. A primer oligonucleotide hybridizes by complementary base-pairing with a target sequence to form a primer-target hybrid. Primer extension products are generated by enzymatic incorporation of nucleotides at the 3' terminus of the primer in the hybrid. When the primer or nucleotide is labelled with a sulfonated diarylrhodamine dye of the invention, labelled primer extension products are generated. These polynucleotide fragments may be subjected to a size-dependent separation process, e.g., electrophoresis or chromatography, and the separated fragments are detected subsequent to the separation, e.g., by laser-induced fluorescence (Hunkapiller, U.S. Pat. No. 4,811,218). Multiple classes of polynucleotides may be separated simultaneously and the different classes are distinguished by spectrally resolvable labels, including dyes of the invention. In electrophoresis, the classes separate on the basis of electrophoretic migration rate.

V.8B DNA Sequencing

The sulfonated diarylrhodamine compounds are well suited for use in automated 4-color DNA sequencing systems with multi-color fluorescent detection capability. The system may use an excitation light source having a wavelength greater than about 630 nm, e.g., a helium-neon gas laser or a solid state diode laser.

The chain termination methods of DNA sequencing, i.e. dideoxy DNA sequencing, or Sanger-type sequencing, and fragment analysis may be employed (Sanger (1977) "DNA sequencing with chain-terminating inhibitors", Proc. Natl. Acad. Sci. USA 74:5463–5467). Exemplary chain-terminating nucleotide analogs include the 2',3'-dideoxynucleoside 5'-triphosphates (ddNTP) which lack the 3'-OH group necessary for 3' to 5' DNA chain elongation. Primers or ddNTP may be labelled with the sulfonated diarylrhodamine dyes of the invention and detected by fluorescence after separation of the fragments by high-resolution electrophoresis. Dyes can be linked to functionality on the 5' terminus of the primer, e.g. amino (U.S. Pat. No. 4,757,141), on the nucleobase of an oligonucleotide primer; or on the nucleobase of a dideoxynucleotide (U.S. Pat. Nos. 5,770,716; 5,821,356; 5,151,507).

Figure 22A:
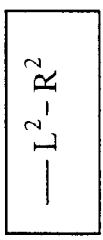
FIG. 22a shows sulfonated dibenzorhodamine compounds 110–113.
Figure 22A:
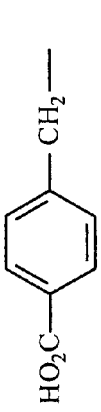
Figure 22A:
Figure 22A:
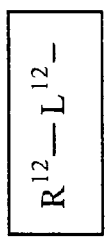
Figure 22A:
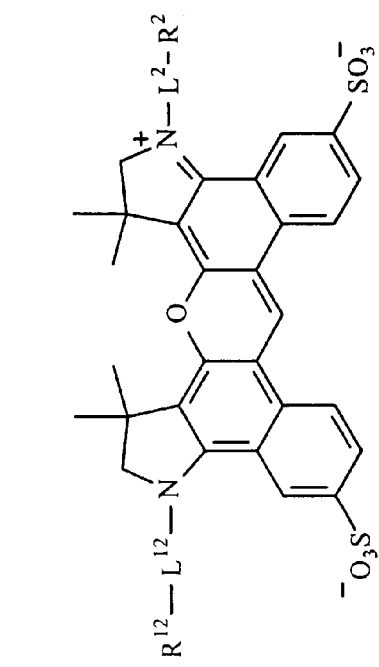
Figure 22B:
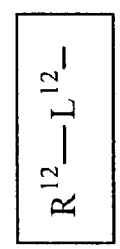
FIG. 22b shows sulfonated benzo-naphthorhodamine compounds 114–116.
Figure 22B:
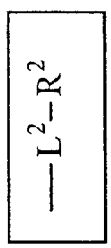
Figure 22B:
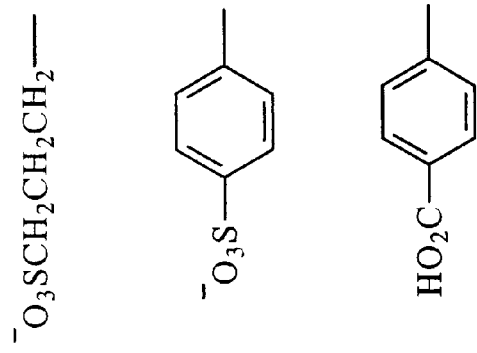
Figure 22B:
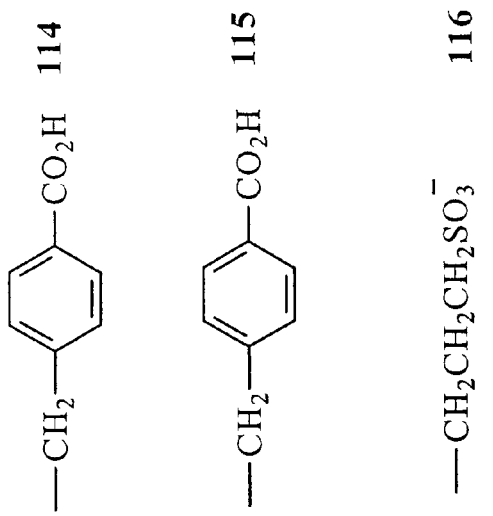
Figure 22B:
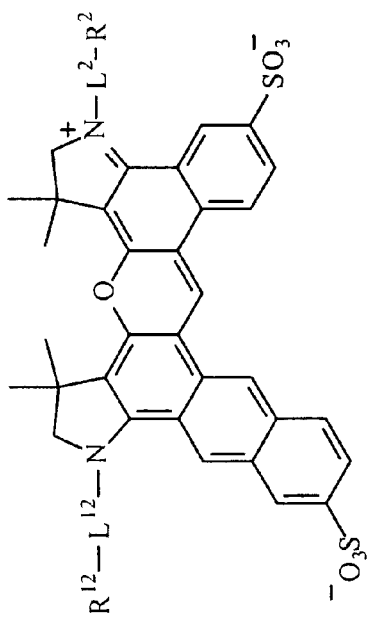
Figure 22C:
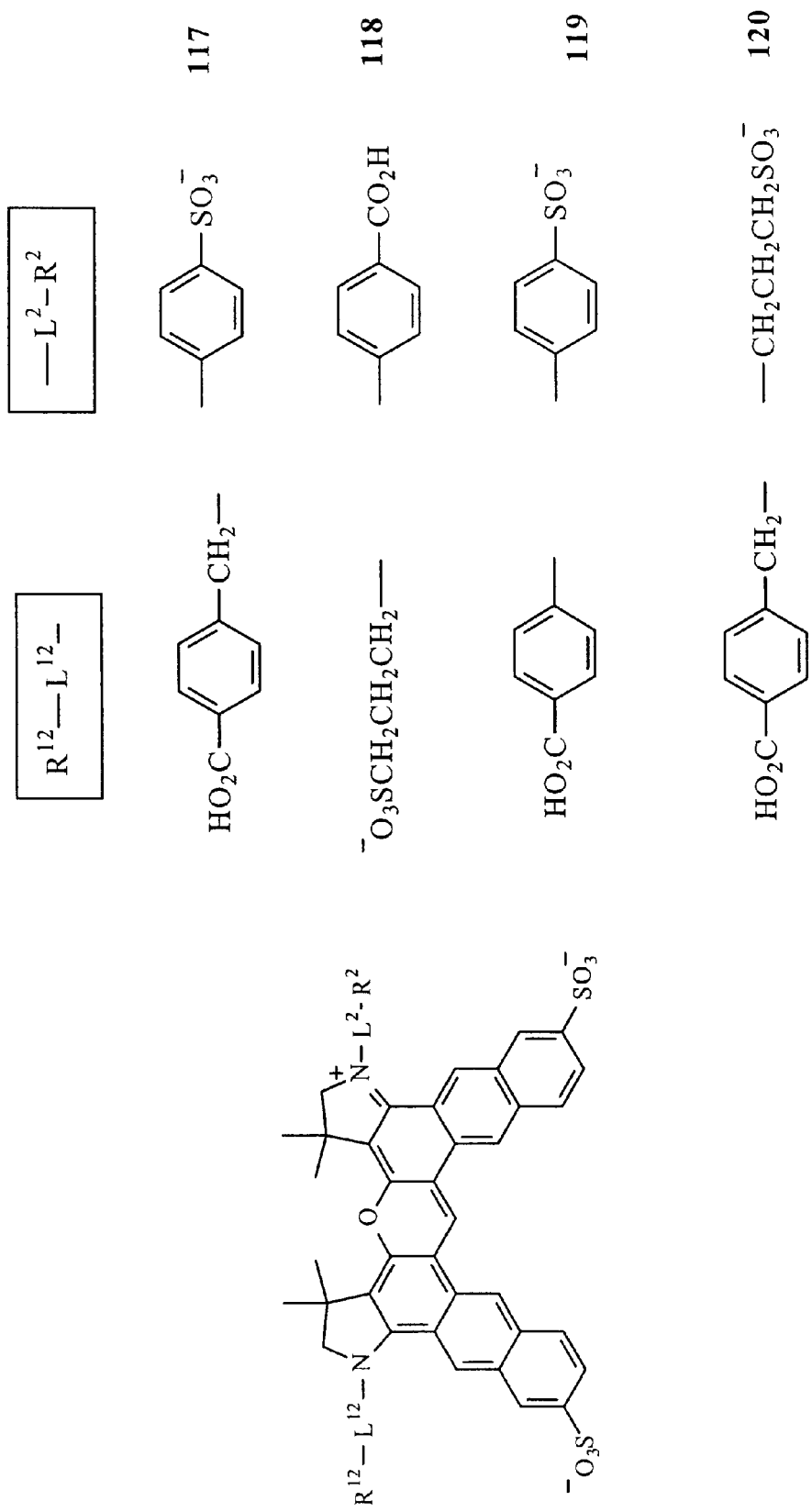
FIG. 22c shows sulfonated dinaphthorhodamine compounds 117–120.

Each of the terminators bears a different fluorescent dye and collectively the terminators of the experiment bear a set of spectrally-resolvable fluorescent labels including one or more of the sulfonated diarylrhodamine dyes of the invention. In an exemplary fragment analysis method, fragments labelled with dyes are identified by relative size, i.e. sequence length, under electrophoresis conditions. Correspondence between fragment size and sequence is established by incorporation of the four possible terminating nucleotides ("terminators") and the members of a set of spectrally resolvable dyes (U.S. Pat. No. 5,366,860). The set of spectrally resolvable dyes includes at least one sulfonated diarylrhodamine compound. One set of four sulfonated diarylrhodamine dyes with well resolved emissions consists of 110, 114, 115, and 119 (FIGS. 22a, 22b, 22c). Another set consists of 110, 114, 116, and 119. Yet another set consists of 110, 114, 119, and 120. Sets of dyes may include any combination of dyes 110–120, or any sulfonated diarylrhodamine dyes generally. A set may include one more sulfonated diarylrhodamine dyes and one or more dye from other structural classes, e.g. fluoresceins, non-sulfonated rhodamines, cyanines, squaraines, and the like.

Labelled nucleotides V may be employed in sequencing as a set of four terminators including the four nucleobases, B=A,G,C,T (or U) and analogs thereof. The combination of B, linker L, and DYE influences the electrophoretic mobility of the polynucleotide fragments, spectral resolution, and the rate of incorporation by polymerase during primer extension.

V.8C Ligation

The covalent joining of nucleic acid probes by ligase enzymes is one of the most useful tools available to molecular biologists. When two probes are annealed to a template nucleic acid where the two probes are adjacent and without intervening gaps, a phosphodiester bond can be formed between a 5' terminus of one probe and the 3' terminus of the other probe by a ligase enzyme, (Whiteley, U.S. Pat. No. 4,883,750; Landegren, (1988) "A ligase mediated gene detection technique", Science 241:1077–80; Nickerson, "Automated DNA diagnostics using an ELISA-based oligonucleotide assay" (1990) Proc. Natl. Acad. Sci USA 87:8923–27). Oligonucleotide ligation assays detect the presence of specific sequences in target DNA sample. Where one or both probes are labelled with a dye, the ligation product may be detected by fluorescence. One or both probes may be labelled with a sulfonated diarylrhodamine dye. Ligation products may be detected by electrophoresis, chromatography, or other size- or charge-based separation method.

V.8D Amplication

The sulfonated diarylrhodamine compounds of the invention find applications as labels on 5'-labelled oligonucleotide primers for the polymerase chain reaction (PCR) and other nucleic acid amplification and selection methods. PCR applications include the use of labelled oligonucleotides for genotyping by variable number tandem repeat (VNTR), short tandem repeat (STR), and microsatellite methods of amplification of repeat regions of double-stranded DNA that contain adjacent multiple copies of a particular sequence, with the number of repeating units being variable. In such PCR genotyping methods, the PCR primer may be labelled with a sulfonated diarylrhodamine of the invention.

In one embodiment, sulfonated diarylrhodamine compounds may be used in quantitative methods and reagents that provide real time or end-point measurements of amplification products during PCR (U.S. Pat. Nos. 5,210,015; 5,538,848). The exonuclease assay (Taqman®) employing fluorescent dye-quencher probes (U.S. Pat. No. 5,723,591; Mullah, (1998) "Efficient synthesis of double dye-labelled oligodeoxyribonucleotide probes and their application in a real time PCR assay", Nucl. Acids Res. 26:1026–1031) gives direct detection of polymerase chain reaction (PCR) products in a closed-tube system, with no sample processing beyond that required to perform the PCR. In the Taqman assay, the polymerase that conducts primer extension and amplifies the polynucleotide also displaces and cleaves a probe annealed to target sequence by 5' to 3' exonuclease activity. In a Taqman-type assay, the probe is self-quenching, labelled with fluorescent dye and quencher moieties, either of which may be dyes of the invention. Spectral overlap allows for efficient energy transfer (FRET) when the probe is intact (Clegg, (1992) "Fluorescence resonance energy transfer and nucleic acids", Meth. Enzymol. 211:353–388). When hybridized to a target sequence, the probe is cleaved during PCR to release a fluorescent signal that is proportional to the amount of target-probe hybrid present (U.S. Pat. Nos. 5,538,848; 5,723,591).

The progress of amplification can be monitored continuously, i.e. real-time detection. Spectrally-resolvable sulfonated diarylrhodamine dyes of the invention are useful in genotyping experiments after PCR amplification of target. In particular, a set of primer oligonucleotides, labelled at the 5' terminus, each with different dyes, can amplify multiple loci and discriminate single nucleotide polymorphisms (SNP) and alleles. Electrophoretic separation of the dye-labelled amplification products, with size standards, establishes a profile or characteristic data set indicating a certain genotype dependent on the set of primer sequences.

V.8E Hybridization Assays

Certain fluorescent dye-quencher probes which hybridize to target nucleic acids are useful in hybridization assays. When the probe is not hybridized to target, the probe may attain conformations that allow spatial proximity between the fluorescent dye and the quencher moieties resulting in fluorescence quenching. Upon hybridization to target, the moieties are physically separated, quenching ceases or diminishes, and fluorescence increases. Where the fluorescence is detectable or quantitated, the presence of target sequence in the sample is deduced. The sulfonated diarylrhodamine dyes of the invention can also be employed as the fluorescent dye or the quencher moiety. Fluorescent dye-quencher probes with self-complementary sequences that form a "hairpin" region, so called "Molecular beacons" (Tyagi and Kramer) undergo the fluorescent change upon hybridization to their complementary target sequence, e.g. in situ quantitation of mRNA in living cells. Hybridization probes labelled with different fluorescent dyes, including the sulfonated diarylrhodamine dyes of the invention, enable multiplex, homogeneous hybridization assays to be carried out in sealed reaction tubes.

Hybridization assays can also be carried out on solid-phase arrays of probes immobilized in pre-determined loci, addressable by specific reagent delivery or interrogation/detection. For example, a sample containing a target polynucleotide labelled with a sulfonated diarylrhodamine dye may be delivered to an array of immobilized probes. Where the polynucleotide hybridizes to an immobilized probe by base-pairing, the fluorescence from the target-probe complex at that location may be detected. From the fluorescence detection pattern and/or intensity, the sequence of the polynucleotide may be deduced, and the presence of absence of a particular polynucleotide sequence in the sample may be determined.

V.9 Kits

The invention includes kits comprising the sulfonated diarylrhodamine compounds of the invention and/or their labelled conjugates. In one embodiment, the kits are useful for conjugating an sulfonated diarylrhodamine compound with a linking moiety to another molecule, i.e. a substrate. Such kits generally comprise an sulfonated diarylrhodamine of the invention including an optional linking moiety and reagents, enzymes, buffers, solvents, etc. suitable for conjugating the dye to another molecule or substance. The sulfonated diarylrhodamine may be an acceptor or donor of an energy-transfer dye.

On one embodiment, the kits are useful for labelling enzymatically synthesized oligonucleotides and polynucleotides with the sulfonated diarylrhodamines of the invention. Such kits generally comprise a labelled enzymatically-incorporatable nucleotide or nucleotide analog according to the invention, a mixture of enzymatically-incorporatable nucleotides or nucleotide analogs capable of supporting continuous primer extension and a polymerase enzyme. The labelled enzymatically-incorporatable nucleotide or nucleotide analog is a compound according to structure V, for example, a labelled terminator. Polymerases may be thermostable, such as AMPLITAQ® DNA polymerase FS (Applied Biosystems, Foster City, Calif.).

Alternatively, the kit may include one or more oligonucleotide primers. The primers may be labelled with sulfonated diarylrhodamines and energy-transfer dyes including sulfonated diarylrhodamines.

VI. EXAMPLES

The invention will be further clarified by a consideration of the following examples, which are intended to be purely exemplary of the invention and not to in any way limit its scope.

Example 1

Synthesis of 1-Diethylamino-3-Hydroxynaphthalene 4 (FIG. 1)

3-Methoxy-1-hydroxynaphthalene 1 (1 gm), synthesized from 1,3-dihydroxynaphthalene by the method of K. H. Bell and L. F. McCaffery (1993), Aust. J. Chem. 46:731, was suspended in dry $CH_2Cl_2$ (30 ml). Dry triethylamine (1.2 equivalents) was added and the reaction was cooled to $-5°$ C. Trifluoromethanesulfonic anhydride (1.1 equivalents) suspended in $CH_2Cl_2$ (15 ml) was added dropwise with vigorous stirring over a period of 2 hours. The reaction was allowed to come to room temperature and subjected to aqueous work up using 5% HCl and $CH_2Cl_2$. The resulting crude 3-methoxynaphthalene-1-triflate 2 was purified by normal phase flash chromatography employing an EtOAc/Hexane (1:10) mobile phase.

The purified 3-methoxynaphthalene-1-triflate 2 was converted to the 1-diethylamino-3-methoxynaphthalene 3 using the palladium-catalyzed triflate/amine coupling procedure of J. P. Wolfe and S. L. Buchwald (1996) Jour. Org. Chem. 61:1133. The 3-methoxy-naphthalene-1-triflate 2 (1 gram) was suspended in 100 ml of dry toluene with 0.015 equivalents of (S)-(−)-2,2'-bis(diphenylphosphino)-1,1'-binaphthyl (BINAP), 0.005 equivalents of tris(dibenzylideneacetone) dipalladium ($Pd_2(dba)_3$), and 3 equivalents of dry diethyl amine. The reaction was purged with argon, and 3.3 equivalents of solid sodium t-butoxide was added with stirring. The reaction was then heated, and stirred for 16 hours at 80° C. in an oil bath. The reaction was allowed to come to room temperature and subjected to aqueous work up using 5% HCl and $CH_2Cl_2$ resulting in a crude 1-diethylamino-3-methoxynaphthalene 3, which was purified by normal phase flash chromatography employing EtOAc: hexane (1:49) as the mobile phase ($^1$HNMR: $CDCl_3$ d 8.20 (broad d, 1H, J=9 Hz), 7.72(broad d, 1H, J=7.8 Hz), 7.43 (dt, 1H, J=7.2, 1.2 Hz), 7.34 (dt, 1H, J=7.7, 1.2 Hz), 6.88 (d, 1H, J=2.4 Hz), ), 6.82 (d, 1H, J=2.4 Hz), 3.93 (s, 3H), 3.21 (q, 4H, J=7.2 Hz), 1.08 (t, 6H, J=7.2 Hz)).

Next, the methyl group of the 1-diethyl-amino-3-methoxy-naphthalene 3 was removed by boron tribromide deprotection as follows. The 1-amino-3-methoxy-naphthalene (100 mg) was suspended in dry $CH_2Cl_2$ (5 ml) and the mixture was cooled to $-70°$ C. in a dry ice/acetone bath. Boron tribromide (10 equivalents) was added dropwise and the reaction was stirred for 30 minutes, then placed in a refrigerator (0° C.) overnight. The reaction was quenched at $-70°$ C. by careful addition of MeOH (10 ml). Solid $NaHCO_3$ (30 equivalents) was added and the reaction was warmed to room temperature, then briefly heated to reflux. The mixture was cooled and filtered, the filtrate was acidified with AcOH, and the solvent was removed in vacuo to give the crude 1-diethylamino-3-hydroxynaphthalene 4, which was purified by normal phase flash chromatography employing EtOAc: hexane (1:4) as the mobile phase.

Example 2

Synthesis of N-Phenyl-3,3-Dimethyl-Hydroxy-Benzoindoline 9 (FIG. 1)

The 3-methoxynaphthalene-1-triflate 2 was derivatized with aniline according to the palladium catalyzed triflate/amine coupling reaction described above in Example 1 to give the 1-anilino-3-methoxynaphthalene 5.

The 1-anilino-3-methoxynaphthalene 5 was acetylated by an amino group acetylation procedure as follows. The 1-amino-3-methoxynaphthalene 5 (500 mg) and 1.2 equivalents of dry $Et_3N$ were suspended in 10 ml of dry $CH_2Cl_2$ and cooled to $-5°$ C. using an ice/NaCl bath. 1.1 equivalent of 2-bromo-2-methylpropionylchloride was added dropwise and the reaction was stirred for 1 hour at $-5°$ C. and stirred at room temperature for an additional 1 hour. The reaction was allowed to come to room temperature and subjected to aqueous work up using 5% HCl and ethylacetate resulting in the crude intermediate 1-(bromoalkyl)amido-3-methoxy-naphthalene 6, which was purified by normal phase flash chromatography employing EtOAc: hexane (1:9) as the mobile phase.

The 1-(bromoalkyl)amido-3-methoxy-naphthalene 6 was cyclized using an $AlCl_3$ catalyzed Friedel-Crafts cyclization procedure as follows. 1 to 3 equivalents of AlCl$_3$ in nitrobenzene was added to the 1-(bromoalkyl)amido-3-hydroxynaphthalene 6. The reaction was heated to 130° C. and reacted for 1 hour. Aqueous work-up using NH$_4$Cl and EtOAc gave the crude N-phenyl-benzoindolinone intermediate 7, which was purified by normal phase flash chromatography employing EtOAc: hexane (1:4) as the mobile phase. The amide carbonyl group of the N-phenyl-benzoindoline intermediate 7 was then reduced with LAH to give compound 8 ($^1$HNMR: CDCl$_3$ d 7.71 (d, 1H, J=7.8 Hz), 7.32 (m, 2H), 7.24 (m, 2H), 7.07 (bt, 1H, J=6.6 Hz), 6.96 (m, 3H), 6.84 (s, 1H), 3.97 (s, 3H), 3.92 (s, 2H), 1.44 (s, 6H).

Methoxy group deprotection of compound 8 was effected using the boron tribromide deprotection procedure described in Example 1, resulting in the N-phenyl-3,3-dimethyl-hydroxy-benzoindoline 9.

Example 3

Synthesis of N-Methyl-5-Hydroxy-(Tetrahydro) benzoquinoline 15 (FIG. 2)

Compound 10 was synthesized by condensation of methoxy-naphthaldehyde and malonic acid employing piperidine catalysis in pyridine. Compound 10 was reduced with hydrogen over 10% Pd/carbon, followed by LAH reduction, and reacted as outlined for the synthesis of compound 2 above with trifluoromethanesulfonic anhydride to give the triflate 11. Triflate 11 was then reacted with NaN$_3$ (3 equiv.) in DMF at 100° C. for 6 hours. Then, the reaction was allowed to come to room temperature and subjected to aqueous work up using pure water and EtOAc resulting in pure compound 12. Compound 12 was suspended in dry CH$_2$Cl$_2$, complexed with 3 to 5 equivalents of solid AlCl$_3$, and refluxed for 2 hours yielding compound 13.

Compound 13 was alkylated with MeI according to a general amino group alkylation procedure as follows. The 3-methoxybenzoquinoline derivative (100 mg) 13 was suspended in 5 ml of dry THF and cooled to −5° C. (ice/NaCl). 1.1 equivalents of n-butyl lithium (1 M) was added dropwise, and the reaction was stirred for 1 hour. 3 equivalents of the MeI alkylating agent was added slowly and the reaction was allowed to stir at room temperature for 2 hours. Aqueous work-up using NH$_4$Cl and EtOAc gave a crude alkylated 3-methoxybenzoquinoline intermediate 14. Intermediate 14 was then purified by normal phase flash chromatography employing EtOAc: hexane (1:19) as the mobile phase ($^1$HNMR: CDCl$_3$ d 8.1 (broad d, 1H, J=8.1 Hz), 7.68(dd, 1H, J=8.1, 1.8 Hz), 7.34 (m, 2H), 6.8 (s, 1H), 3.92 (s, 3H), 3.21 (m, 2H), 2.94 (s, 3H), 2.77 (t, 2H, J=6.6 Hz), 1.92 (m, 2H)). Subsequent methoxy group deprotection by the general boron tribromide procedure described above in Example 1 resulted in the N-methyl-hydroxybenzoquinoline derivative 15.

Example 4

Synthesis of 3-(5-Hydroxybenzoquinolin-1-yl) propanesulfonic acid 17 (FIG. 2)

Compound 13 was synthesized according to the procedure outlined above in Example 3 for the synthesis of the N-methyl-hydroxybenzoquinoline derivative 15. Compound 13 was then alkylated according to the general amino group alkylation procedure described above in Example 3, this time using 1,3-propane sultone as the alkylating agent rather than MeI, to give a 5-methoxybenzoquinoline-N-propanesulfonic acid intermediate 16 ($^1$HNMR: CD$_3$OD d 7.94 (d, 1H, J=8.7 Hz), 7.65 (d, 1H, J=8.4 Hz), 7.32 (t, 1H), 7.27 (t, 1H), 6.85 (s, 1H), 4.89 (s, 3H), 3.20 (m, 2H), 3.08 (bt, 2H, J=6 Hz), 2.91 (m, 2H), 2.72 (t, 2H, J=6.6 Hz), 2.33 (m, 2H), 1.89 (m, 2 H). Subsequent methoxy group deprotection of compound 16 by the general boron tribromide procedure described above in Example 1 resulted in the 3-(5-hydroxybenzoquinolin-1-yl) propanesulfonic acid 17.

Example 5

Synthesis of N-Methyl-2,2,4-Trimethyl-5-Hydroxy-(Tetrahydro)benzoquinoline 22 (FIG. 3)

1-Amino-3-methoxynaphthalene 18 was synthesized according to the procedure of G. T. Morgan and E. D. Evans (1919), J. Chem. Soc. 115:1126, or as described in Example 10. Following the procedure of A. Rosowsky and E. J. Modest (1965) Jour. Org. Chem. 30: 1832, 18 (1 gm) was dissolved in dry acetone (50 ml), and 0.01 equivalent of iodine was added to the solution. The reaction was heated and stirred for 16 hours, cooled, and then quenched with saturated Na$_2$S$_2$O$_3$. The reaction mixture was then subjected to aqueous work up using saturated Na$_2$S$_2$O$_3$ and EtOAc resulting in the crude methoxybenzoquinoline 19. The methoxybenzoquinoline 19 was purified by flash chromatography using an EtOAc/hexane 1:9 mobile phase. Compound 19 was then alkylated with MeI according to the general amino group alkylation procedure described above in Example 3 to give compound 20. Compound 20 was reduced with H$_2$ in a Parr hydrogenator at 70 psi and 10% Pd/C catalysis to give a N-methyl-2,2,4-trimethyl-5-methoxybenzoquinoline intermediate 21 ($^1$HNMR: CDCl$_3$ d 8.20 (bd, 1H, J=7.5 Hz), 7.65 (bd, 1H, J=7.5 Hz), 7.33 (m, 2H), 6.89 (s, 1H), 3.94 (s, 3H), 3.14 (b sextet, 1H, J=6.6 Hz), 2.80 (3, 3H), 1.89 (d, 2H, J=8.7), 1.42 (d, 3H, J=6.9 Hz), 1.34 (s, 3H), 1.05 (s, 3H). Subsequent methoxy group deprotection of compound 21 by the general boron tribromide procedure described above in Example 1 gave the N-methyl-5-hydroxy-(tetrahydro) benzoquinoline 22.

Example 6

Synthesis of N-Methyl-3,3-Dimethyl-4-Hydroxy-Benzoindoline 27 (FIG. 3)

1-Amino-3-methoxynaphthalene 18 was acetylated with 2-bromo-2-methylpropionyl chloride according to the general amino group acylation procedure described above in Example 2 to give compound 23. Compound 23 was cyclized by the Friedel-Crafts cyclization procedure described above in Example 2 to give compound 24. Next, compound 24 was reduced with 3 equivalents LAH in THF to give the 4-methoxybenzoindoline 25. Compound 25 was alkylated using the general amino group alkylation procedure described above in Example 3 using methyl iodide as the alkylating agent to give a N-methyl-3,3-dimethyl-4-methoxybenzoindoline intermediate 26 ($^1$HNMR: CDCl$_3$ d 8.07 (bd, 1H, J=8.4 Hz), 7.69 (bd, 1H, J=8.1 Hz), 7.33 (bt, 1H, J=7.8 Hz), 7.22 (bt, 1H, J=8.1 Hz), 6.70 (s, 1H), 3.92 (s, 3H), 3.32 (s, 2H), 3.32 (s, 3H), 1.44 (s, 6H). Subsequent methoxy group deprotection of compound 26 by the general boron tribromide procedure described in Example 1 resulted in the N-methyl-3,3-dimethyl-4-hydroxy-benzoindoline 27.

Example 7

Synthesis of N-Ethyl-3,3-Dimethyl-4-Hydroxy-Benzoindoline 29 (FIG. 3)

The 4-methoxybenzoindoline 25 was synthesized as described above in Example 6. Compound 25 was alkylated by the general amino group alkylation procedure described in Example 3 employing ethyl iodide as the alkylating agent to give the N-ethyl-3,3-dimethyl-4-methoxybenzoindoline intermediate 28 ($^1$HNMR: CDCl$_3$ d 7.90 (d, 1H, J=8.7 Hz), 7.68 (d, 1H, J=8.1 Hz), 7.32 (bt, 1H, J=7.5 Hz), 7.22 (bt, 1H, J=6.9 Hz), 6.69 (s, 1H), 3.83 (s, 3H), 3.52 (q, 2H J=7.5 Hz), 3.38 (s, 2H), 1.46 (s, 6H), 1.27 (t, 3H, J=7.5 Hz). Subsequent methoxy group deprotection of compound 28 by the general boron tribromide procedure described in Example 1 yielded the N-ethyl-3,3-dimethyl-4-hydroxy-benzoindoline 29.

Example 8

Synthesis of Selected Dibenzorhodamine Dye Compounds

General Procedure A (FIG. 5). A solid phthalic anhydride derivative 34 was mixed with 1.4 equivalents of an aminohydroxy intermediate 31 and 2.8 equivalents of ZnCl$_2$. The oven dried reaction vessel was capped with a rubber septa and purged with Argon. The solid mixture was heated briefly at 130° C. until melting was observed, e.g., after approximately 15 minutes. 1,2-Dichlorobenzene (approximately 10 equivalents) was added by syringe to the reaction mixture, and the heterogeneous mixture was heated to 130 to 170° C. for 4 hours. The crude reaction mixture was cooled, suspended in a minimal amount of MeOH:CH$_2$Cl$_2$ (1:19), loaded directly onto a normal phase flash chromatography column, and the crude dye was eluted with an MeOH:CH$_2$Cl$_2$ (1:19) mobile phase. When necessary, the dye was purified and separated into distinct isomers 35 and 36 by PTLC developed with MeOH:CH$_2$Cl$_2$ (1:9). The isomerically pure dye, which migrated as a single spot on silica TLC eluting with 1:9 MeOH:CH$_2$Cl$_2$, was identified by its UV/Visible absorption spectra and its long wavelength fluorescent excitation and emission spectra.

General Procedure B (FIG. 6). In the general procedure outlined in FIG. 6, a solid phthalic anhydride derivative 34 (100 mg) was placed in a round bottom flask capped with a rubber septa and purged with dry argon. Dry nitrobenzene (2 ml) was added and heated to dissolve the anhydride. The mixture was cooled to room temperature and 3 to 6 equivalents of anhydrous AlCl$_3$ was added with stirring to dissolve the solid. Subsequently, 1 equivalent of a 1-amino-3-methoxynaphthalene intermediate 31 was added with stirring and the reaction was heated to 130° C. for 1 hour. The reaction was then cooled and suspended in EtOAc. The organic layer was washed with saturated NH$_4$Cl and brine, dried over Na$_2$SO$_4$, filtered, and the solvent was removed in vacuo. When necessary, the resulting ketone intermediate 37/38 was purified and separated into distinct isomers 37 and 38 using normal phase flash chromatography using (MeOH:CH$_2$Cl$_2$, 1:19) as the mobile phase, or by recrystallization. The methoxy group of the isomerically pure intermediate 37 or 38 was removed according to the general boron tribromide deprotection procedure described in Example 1 to give amino-hydroxynaphthalene ketone 39. The amino-hydroxynaphthalene ketone 39 (100 mg) was then reacted at 130° C. with 1 equivalent of a 1-amino-3-naphthalene intermediate 32 in dry 1,2-dichlorobenzene (2 ml) for 2 hours. The reaction was cooled, giving isomerically pure and asymmetrically substituted product 40 that was purified as in General Procedure A above.

Figure 7:
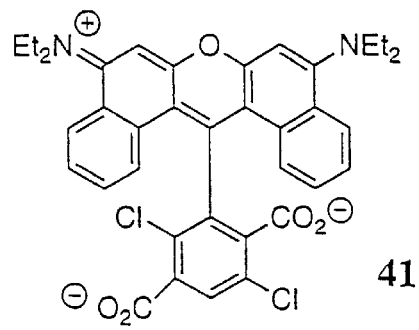
FIG. 7 shows the structures of several exemplary dibenzorhodamine dye compounds of the invention.
Figure 7:
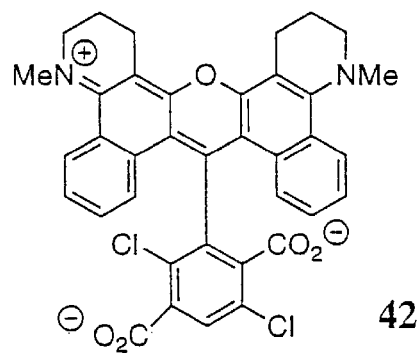
Figure 7:
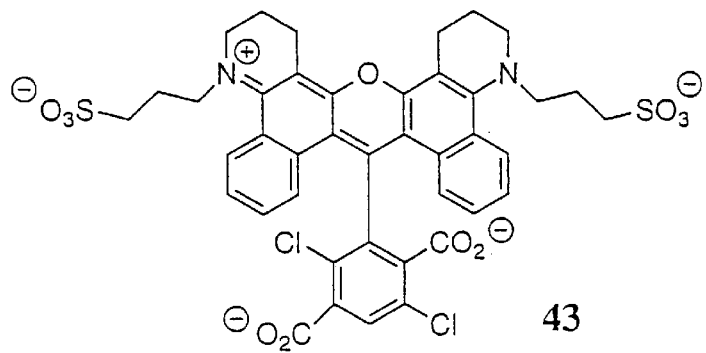
Figure 7:
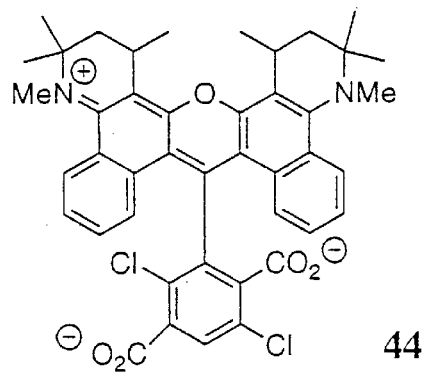
Figure 7:
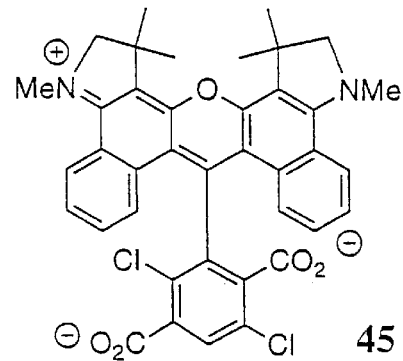
Figure 7:
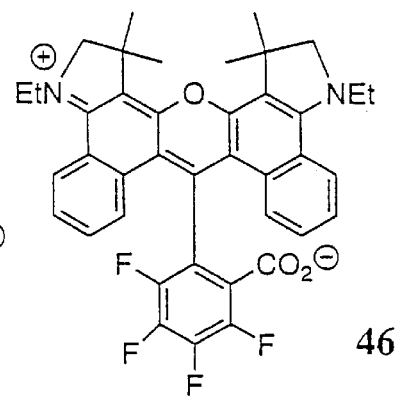
Figure 7:
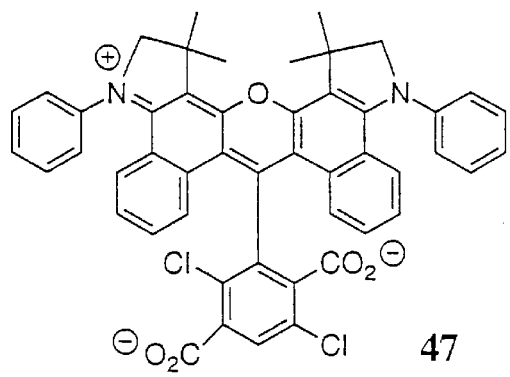

Synthesis of Dibenzorhodamine Dye 41 (FIG. 7). General procedure A was followed employing dichlorotrimellitic anhydride as the phthalic anhydride derivative, i.e., compound 34 where the substituents at C-14 and C-17 are Cl and the substituent at C-15 is CO$_2$H, and 1-diethylamino-3-hydroxynaphthalene 4 as the aminohydroxy intermediate 31.

Synthesis of Dibenzorhodamine Dye 42 (FIG. 7). General procedure A was followed employing dichlorotrimellitic anhydride as the phthalic anhydride derivative, i.e., compound 34 where the substituents at C-14 and C-17 are Cl and the substituent at C-15 is CO$_2$H, and N-methyl-5-hydroxy-benzoquinoline 15 as the aminohydroxy intermediate 31.

Synthesis of Dibenzorhodamine Dye 43 (FIG. 7). General procedure A was followed employing dichlorotrimellitic anhydride as the phthalic anhydride derivative, i.e., compound 34 where the substituents at C-14 and C-17 are Cl and the substituent at C-15 is CO$_2$H, and 5-hydroxy-benzoquinoline 17 as the aminohydroxy intermediate 31.

Synthesis of Dibenzorhodamine Dye 44 (FIG. 7). General procedure A was followed employing dichlorotrimellitic anhydride as the phthalic anhydride derivative, i.e., compound 34 where the substituents at C-14 and C-17 are Cl and the substituent at C-15 is CO$_2$H, the N-methyl-2,2,4-trimethyl-5-hydroxy-benzoquinoline 22 as the aminohydroxy intermediate 31.

Synthesis of Dibenzorhodamine Dye 45 (FIG. 7). General procedure A was followed employing dichlorotrimellitic anhydride as the phthalic anhydride derivative, i.e., compound 34 where the substituents at C-14 and C-17 are Cl and the substituent at C-15 is CO$_2$H, and N-methyl-3,3-dimethyl-4-hydroxy-benzoindoline 27 as the aminohydroxy intermediate 31.

Synthesis of Dibenzorhodamine Dye 46 (FIG. 7). General procedure A was followed employing tetrafluorophthalic anhydride as the phthalic anhydride derivative, i.e., compound 34 where the substituents at C-14 to C-17 are F, and N-ethyl-3,3-dimethyl-4-hydroxy-benzoindoline 29 as the aminohydroxy intermediate 31.

Synthesis of Dibenzorhodamine Dye 47 (FIG. 7). General procedure A was followed employing dichlorotrimellitic anhydride as the phthalic anhydride derivative, i.e., compound 34 where the substituents at C-14 and C-17 are Cl and the substituent at C-15 is CO$_2$H, and N-phenyl-3,3-dimethyl-4-hydroxy-benzoindoline 9 as the aminohydroxy intermediate 31.

Example 9

Spectral Properties of Selected Dibenzorhodamine Dye Compounds

The following table presents important spectral properties of several representative dibenzorhodamine dye compounds of the invention. All spectra were recorded at room temperature, in 1×TBE buffer and 8 M urea, for the free dye having 0.05 absorption at the dye's $\lambda_{max,abs}$. Dye concentration was approximately $10^{-6}$ M.

| Dye | Absorption Maximum (nm) | Emission Maximum (nm) | Full Width at Half Max (nm) |
| --- | --- | --- | --- |
| 41 | 585 | 614 | 59 |
| 42 | 609 | 634 | 42 |
| 43 | 597 | 637 | 47 |
| 44 | 598 | 640 | 50 |
| 45 | 639 | 650 | 31 |
| 46 | 639 | 652 | 33 |
| 47 | 632 | 676 | 66 |

Example 10

Figure 8:
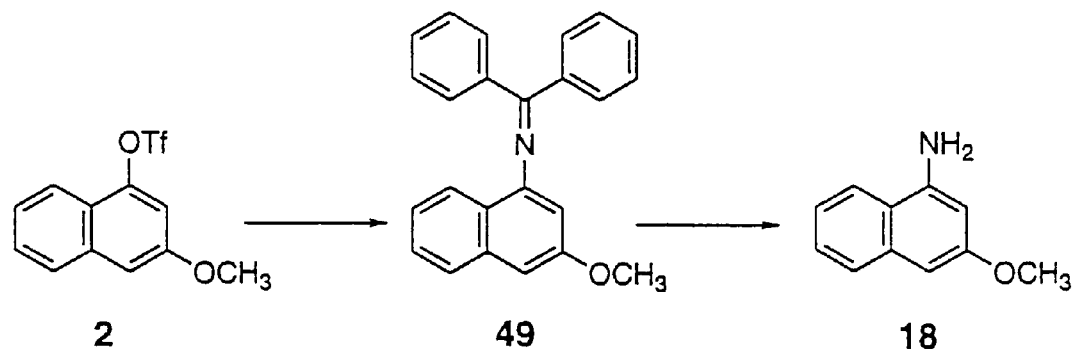
FIG. 8 shows a synthesis of compound 18.
Figure 9:
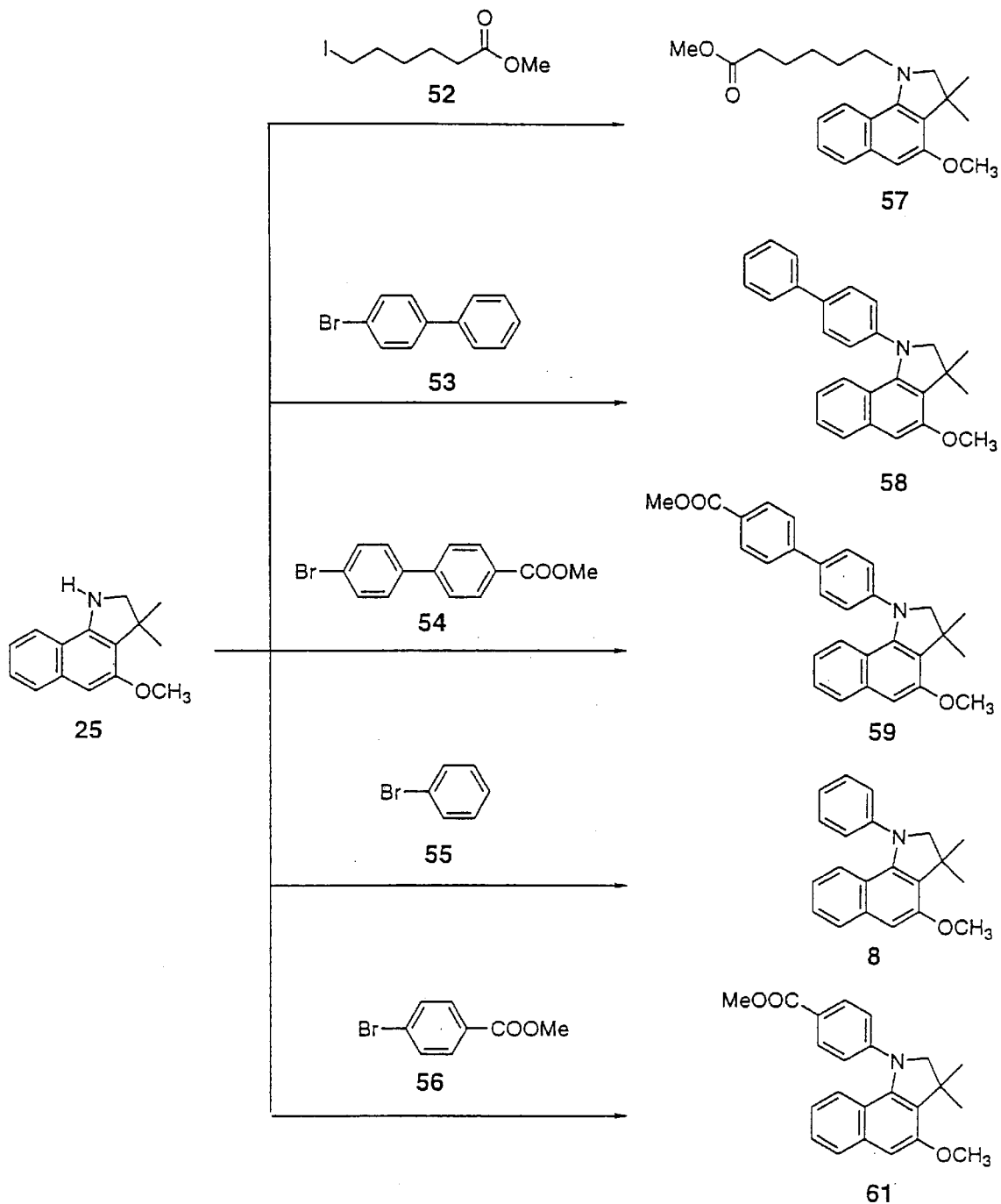
FIG. 9 shows a synthesis of compounds 57–61.

Synthesis of 3,3-dimethyl-hydroxy-benzoindoline 25 (FIGS. 8 and 9)

Compound 2 was converted to 1-amino-3-methoxynaphthalene 18 using the palladium-catalyzed triflate/imine coupling and hydrolysis procedure of Buchwald (Buchwald, S.L. et al Tetrahedron Letters, 1997, 38/36, 6367–6370) as follows (FIG. 8).

The 3-methoxy-naphthalene-1-triflate 2 (25 g) was mixed with 0.013 equivalents of tris(dibenzylideneacetone)-dipalladium ($Pd_2(dba)_3$), 0.04 equivalents of racemic 2,2'-bis(diphenylphosphino)-1,1'-binaphthyl (±BINAP), 1.3 equivalents of potassium carbonate, 1.3 equivalents of cesium carbonate, and 1.5 equivalents of benzophenone imine. Alternatively, potassium or sodium t-butoxide (2.6 equivalents) could be used as a substitute base for the reaction. The reaction mixture was suspended in 75 ml of dry toluene and 75 ml of dry tetrahydrofuran and stirred for 24 hours at 120° C. in an oil bath. A mixture of 75 ml of hexane/ethyl acetate (9:1) was added to the reaction mixture, and the mixture was eluted through silica gel with hexane/ethyl acetate (3:2). The elutant was collected and then concentrated under reduced pressure. To the concentrated oil, hexane/ethyl acetate (9:1) was added to crystallize out 1-benzophenone imino-3-methoxynaphthalene 49 as yellow crystals (20.0 g, 72.6%). The mother liquor was concentrated and hexane/ethyl acetate (9:1) was added to crystallize out a second crop of 49 as yellow crystals (3.0 g, 10.9%). (Total yield: 83.5%).

Compound 49 was hydrolyzed under acid conditions to give 18 as follows. Compound 49 (27 gm) was suspended in 150 ml of 1,4-dioxane and 100 ml of 5% sulfuric acid ($H_2SO_4$). The reaction was then heated and stirred for 1 hour at 50° C. in an oil bath. The reaction mixture was cooled to room temperature and washed with 150 ml of hexane/ethyl acetate (3:2). The solution was then basified with ice cold aqueous NaOH to pH 10–11, and extracted three times with ethyl acetate. The combined organic extract was dried with sodium sulfate ($Na_2SO_4$) and evaporated under reduced pressure to give 18 as pale brown oil which crystallized upon standing (13.9 g, 100%).

Compound 25, 3,3-dimethyl-hydroxy-benzoindoline, was synthesized from 18 according to the procedure described above in Example 6.

Example 11

Synthesis of N-Substituted Methoxybenzoindoline Intermediates 57–61 (FIG. 9)

Compound 25 was employed as a common intermediate to synthesize the N-substituted derivatives 57–61 by either alkylative substitution or palladium catalysed coupling to the secondary amine group (FIG. 9).

Synthesis of N-(6-hexanoic acid)-3,3-dimethyl-hydroxy-benzoindoline 57

Compound 25 (2.3 g) was alkylated by treating with 3 equivalents of commercially available methyl-6-iodohexanoic acid 52 and 3 equivalents of diisopropylethylamine. The mixture was suspended in 23 ml of dry toluene and heated at 130° C. in an oil bath with stirring for 18 hours. The solvent was evaporated under reduced pressure to give crude N-(6-hexanoic acid)-3,3-dimethyl-hydroxy-benzoindoline 57. Crude 57 was dissolved in dichloromethane and purified by normal phase flash chromatography eluting with hexane/ethyl acetate (99:1)(yield 2.55 g, 74%).

Synthesis of N-(biphenyl)-3,3-dimethyl-hydroxy-benzoindoline 58

Compound 25 (2.3 g) was N-arylated by palladium catalysed coupling according to the established procedure (Buchwald, et al J. Org., 1997, 62, 6066–6068) as follows: Compound 25 (2 g) was mixed with 1.4 equivalents of 4-bromo-biphenyl 7, sodium t-butoxide 1.3 equivalents), 0.013 equivalents of tris(dibenzylideneacetone)dipalladium ($Pd_2(dba)_3$), 0.04 equivalents of racemic 2,2'-bis(diphenylphosphino)-1,1'-binaphthyl (±BINAP). The reaction mixture was suspended in 100 ml of dry toluene, stirred well, and heated at 130° C. in an oil bath overnight (16 hrs.). The reaction mixture was quenched with aqueous ammonium chloride ($NH_4Cl$) and extracted (3x) with ethyl acetate. The organic extract was dried with anhydrous $Na_2SO_4$. Hexane (equal volume) was added to the crude reaction mixture and it was eluted through silica-gel with hexane/ethyl acetate (1:1). The solvent was evaporated under reduced pressure and the residue was purified by normal phase flash chromatography eluting with hexane/ethyl acetate (98:2) to give N-(biphenyl)-3,3-dimethyl-hydroxy-benzoindoline 58 (yield 85% ) as white powder.

Synthesis of N-(carboxybiphenyl)-3,3-dimethyl-hydroxy-benzoindoline 59

Compound 54 was synthesized from commercially available bromo-biphenyl-methyl ketone by a haloform reaction to give the bromo-biphenyl acid, followed by esterification employing established procedures. Compound 25 was N-arylated with 54 according to the established procedure (Buchwald, etal Tetrahedron Letters, 1997, 38/36, 6359–6362) as follows: Compound 25 (0.4 g) was mixed with 1.4 equivalents of compound 54. 0.013 equivalents of tris(dibenzylideneacetone)dipalladium ($Pd_2(dba)_3$), 0.04 equivalents of racemic 2,2'-bis(diphenylphosphino)-1,1'-binaphthyl (±BINAP), and 3 equivalents of cesium carbonate. The reaction mixture was suspended in 100 ml of dry toluene and 100 ml of dry tetrahydrofuran , then heated at 130° C. in an oil bath and stirred for 18 hours. The reaction was cooled and hexane (30 ml) was added to the crude mixture. The crude product was eluted through silica-gel with hexane/ethyl acetate (3:2). The solvent was removed under reduced pressure and the N-(carboxybiphenyl)-3,3-dimethyl-hydroxy-benzoindoline 59 was purified by normal phase flash chromatography eluting with hexane/ethyl acetate: (95:5) (bright yellow solid yield 0.25 g, 32%).

Synthesis of N-phenyl-3,3-dimethyl-hydroxy-benzoindoline 60

Compound 25 was N-arylated with iodobenzene or bromobenzene as described above for synthesis of compound 58 from compound 25. Pure N-phenyl-3,3-dimethyl-hydroxy-benzoindoline 8 was isolated after normal phase flash chromatography employing hexane/ethyl acetate: (98:2).

Synthesis of N-carboxyphenyl-3,3-dimethyl-hydroxy-benzoindoline 61

Compound 25 was N-arylated with methyl iodobenzoate or methyl bromobenzoate as described above for synthesis of compound 59. Pure N-carboxyphenyl-3,3-dimethyl-hydroxy-benzoindoline 61 was isolated after normal phase flash chromatography employing hexane/ethyl acetate: (95:5).

Example 12

Synthesis of Dibenzorhodamine Dyes 67, 72, 76 and 81 (FIGS. 10–13)

Figure 10:
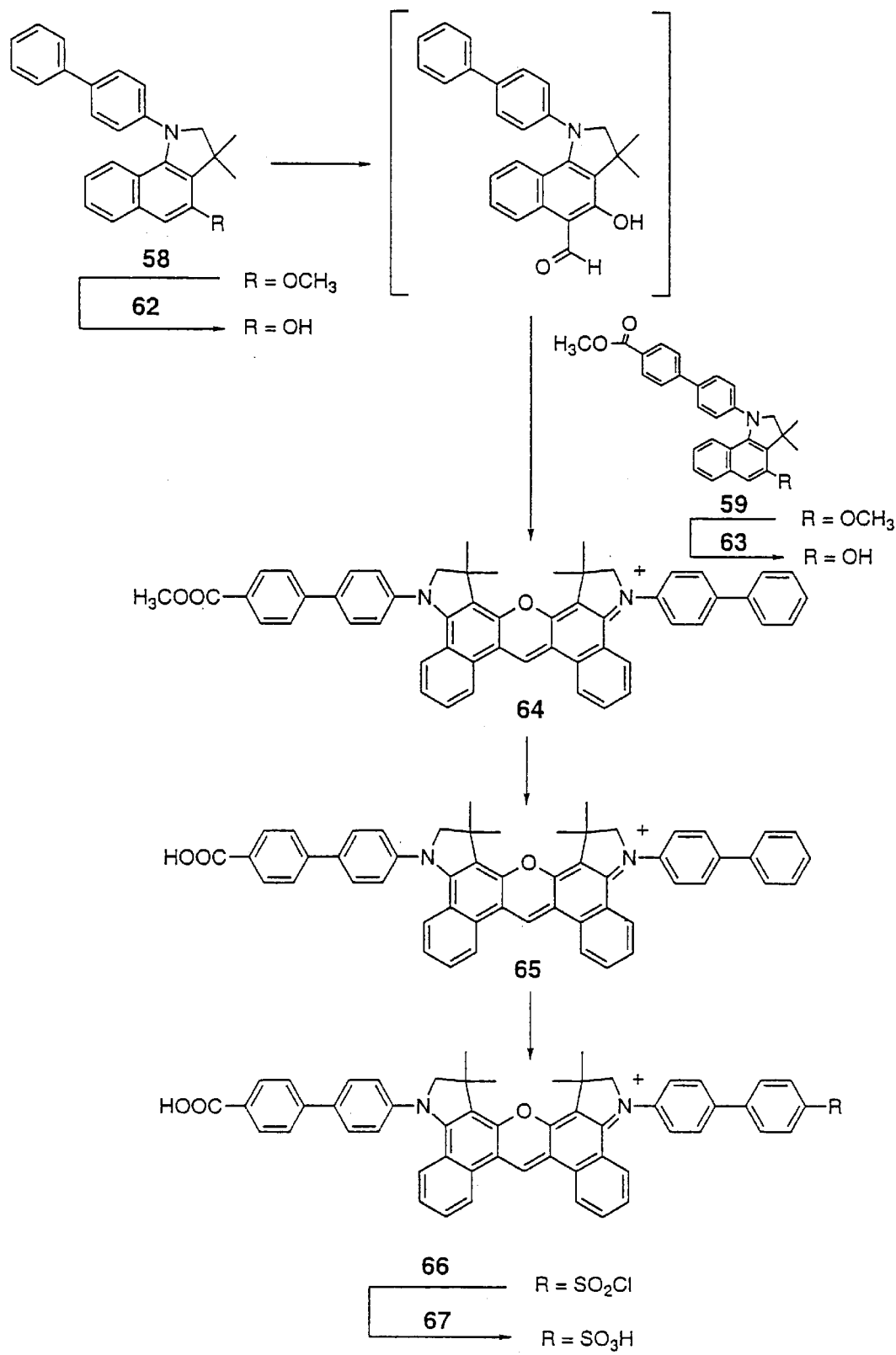
FIG. 10 shows a synthesis of compound 67.

Synthesis of Dye 67 (FIG. 10). Hydroxyindoline 62 was obtained by demethylation of compound 58 using aluminum chloride (AlCl$_3$) according to the following procedure: Compound 58 (2 g), and aluminum chloride (6 g) were thoroughly mixed under a strong stream of argon and the reaction mixture purged for 10 minutes with argon. The solid mixture was heated under Argon in an oil bath from 90° C. to 120° C. over 20 min. The reaction mixture was cooled and the solids suspended in dichloromethane and transferred into a solution of ice and dilute H$_2$SO$_4$. The aqueous layer was extracted five times, the combined organic extract was washed with saturated sodium chloride, and dried over sodium sulfate. After filtration, the solvent was evaporated under reduced pressure and pure 62 (0.13 g) was isolated after normal phase flash chromatography eluting with dichloromethane/methanol (99:1). Hydroxyindoline 63 was generated from compound 59 employing the same procedure as that for conversion of compound 58 to compound 62.

Next, one equivalent of a 1:1complex of N-methylformanilide and phosphorous oxychloride in dry dichloromethane was added to one equivalent of 62 in a small pear flask (100 mg in a 5 ml flask). The reaction mixture was heated at 80° C. in an oil bath under a stream of Argon until the dichloromethane was evaporated leaving a dark red oil. Nitrobenzene (300 ul) was added followed by addition of 2 equivalents of POCl$_3$. To the above solution was added one equivalent of 63 suspended in nitrobenzene (500 ul). The reaction mixture was heated from 80° C. to 155° C. over 25 min. and then kept at 155° C. for 15 minutes. The reaction was cooled and transferred with dichloromethane to 5% HCl. The aqueous layer was saturated with brine and extracted 3× with dichloromethane. The combined organic extracts were separated and evaporated under reduced pressure to give the crude dye derivative 64. Crude 64 was suspended in acetic acid (3 ml) and 5% HCl (3 ml) and heated at 60° C. for 1 hour. The reaction mixture was then poured into a solution of ice, saturated aqueous sodium chloride, and extracted 3 times with dichloromethane. After evaporation of the combined oroanic layers, the pure monocarboxylated asymmetric dye derivative 65 was then purified from the other two symmetric dye products, the bis-biphenyl and bis-carboxybiphenyl dyes, by normal phase flash chromatography eluting with dichloromethane/methanol (9:1).

Finally, the purified dye derivative 65 was sulfonated to give dye 67 as follows. Dye derivative 65 (30 mg) and 3 equivalents of anhydrous sodium sulfate were suspended in dry dichloromethane (50 ml) at 0° C. under Argon. To the above solution, 5 equivalents of chlorosulfonic acid (ClSO$_3$H) were added and the reaction mixture was stirred at room temperature for 18 hours. The reaction mixture was quenched with saturated aqueous sodium chloride/5% HCl and the aqueous layer extracted 3 times with dichloromethane. The organic extract was evaporated under reduced pressure to give crude dye 66. Crude dye 66 was suspended in a solution of dioxane and 5% HCl (2:1) and stirred at room temperature for 20 hours. The solution was then concentrated under reduced pressure, suspended in saturated aqueous sodium chloride and extracted 3 times with dichloromethane. The solvent was evaporated to give crude dye 67. Pure dye 67 was isolated by normal phase preparative thin layer chromatography (PTLC) developed with methanol/dichloromethane (1:4) or flash chromatography eluting with methanol/dichloromethane (1:9).

Figure 11:
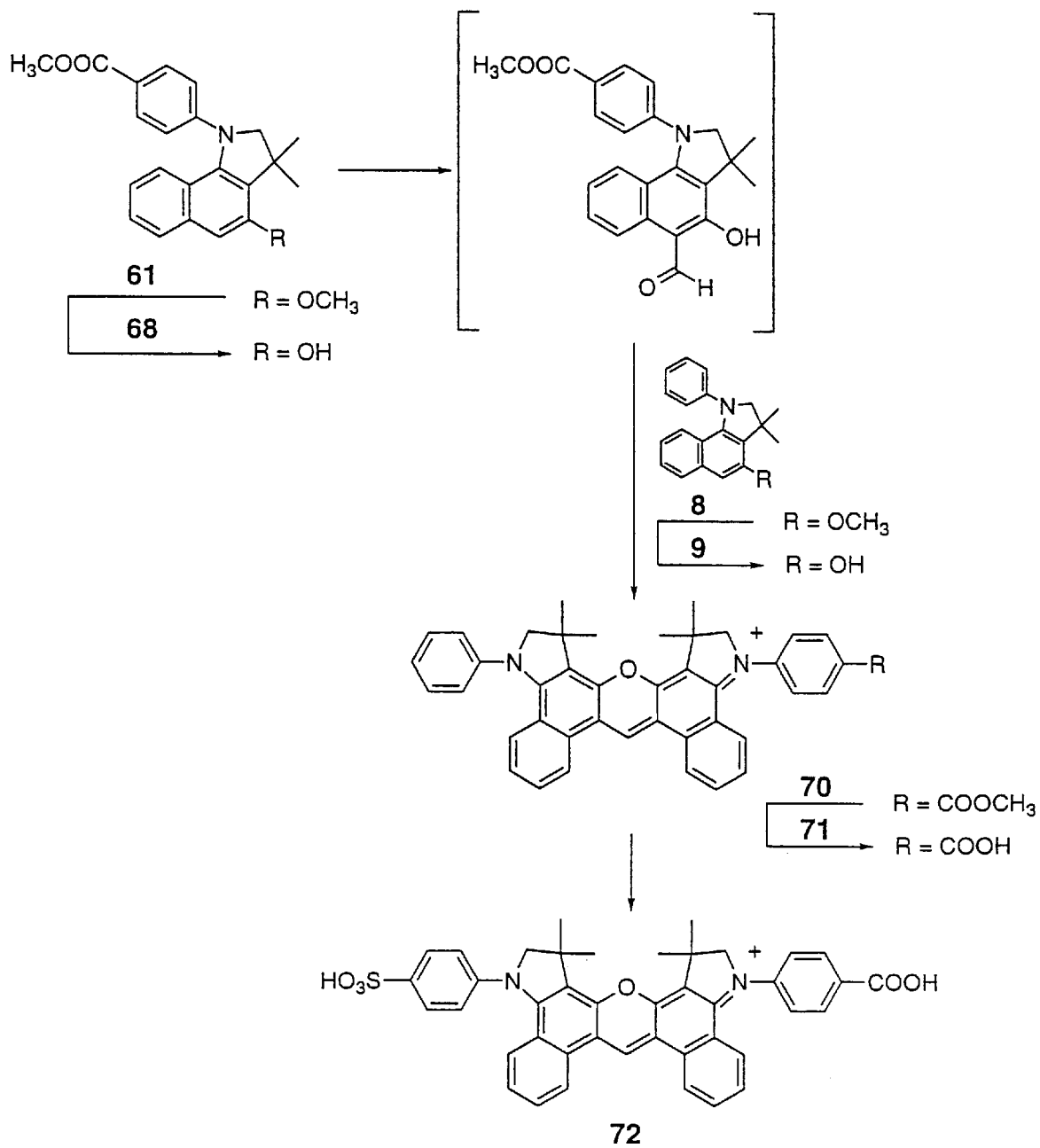
FIG. 11 shows a synthesis of compound 72.

Synthesis of Dye 72 (FIG. 11)

Compound 61 was demethylated to give compound 68, and compound 8 was demethylated to give compound 9, both employing the aluminum chloride deprotection procedure described above for conversion of compound 58 to compound 62. Compound 68 was reacted with the methyl formanilide/POCl$_3$ complex, and subsequently with compound 9 to generate dye derivative 70 as described for the synthesis of dye derivative 64 from compounds 62 and 63. Crude dye derivative 70 was hydrolysed by acid to give dye derivative 71 according to the procedure for generation of dye derivative 65 from 64 above. The pure asymmetric dye derivative 71 was purified by PTLC from the two symmetric bis-phenyl and bis-carboxyphenyl dye products. The purified dye 71 was then sulfonated and hydrolysed to give crude dye 72 as described above for generation of dye 67 from dye derivative 65. Pure dye 72 was isolated by normal phase preparative thin layer chromatography (PTLC) developed with methanol/dichloromethane (1:4) or flash chromatography eluting with methanol/dichloromethane (1:9).

Figure 12:
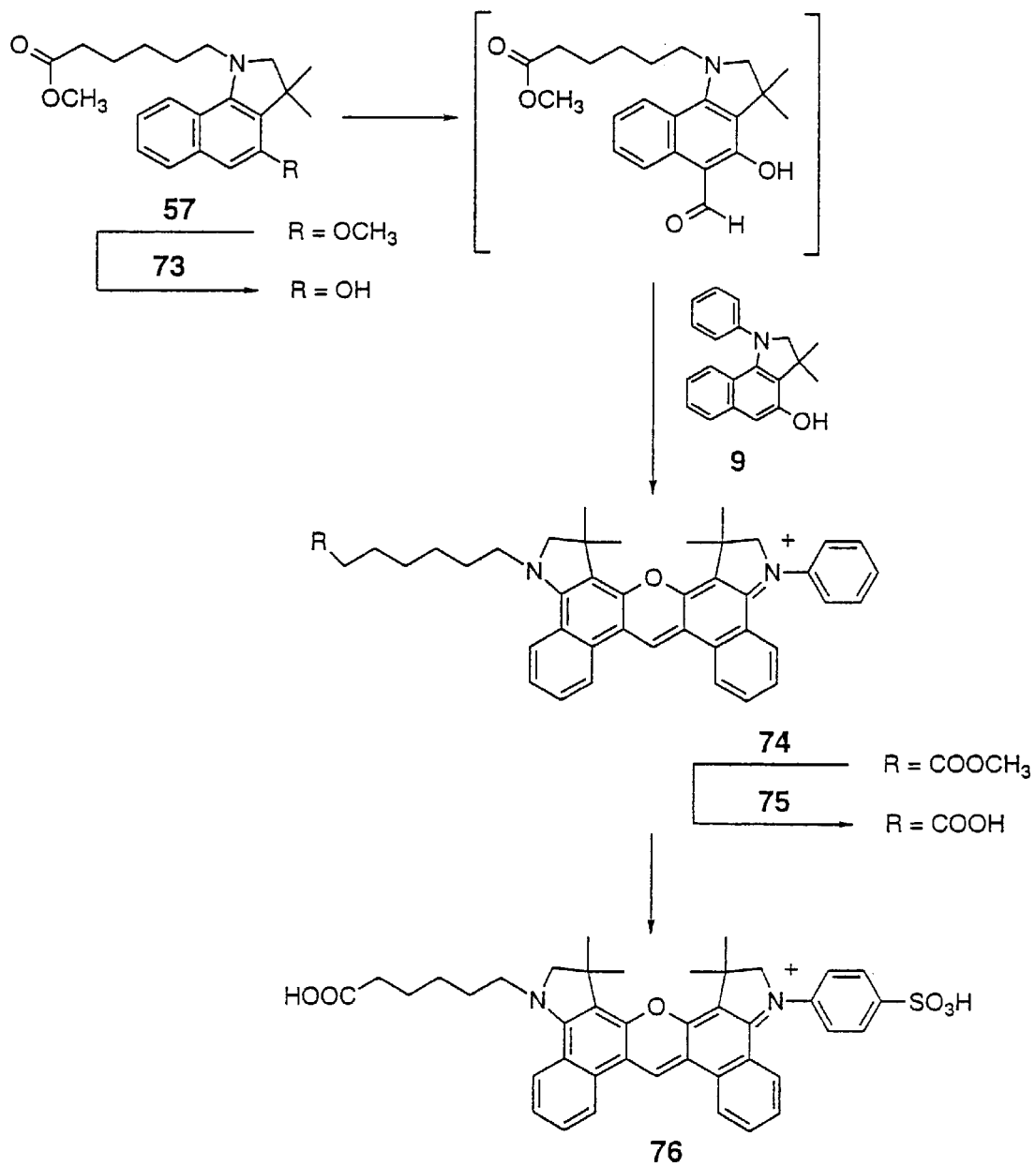
FIG. 12 shows a synthesis of compound 76.

Synthesis of Dye 76 (FIG. 12)

Compound 57 was demethylated to give compound 73 by boron tribromide deprotection, and compound 8 was demethylated to give 9 employing the aluminum chloride deprotection procedure described above for conversion of compound 58 to compound 62. Compound 57 reacted with the methyl formanilide/POCl$_3$ complex under the standard conditions, and subsequently with compound 9 under the standard conditions to generate dye derivative 74 as described above in Example 7. Crude dye derivative 74 was hydrolysed by standard acid hydrolysis to give dye derivative 75. The pure asymmetric dye derivative 75 was purified by PTLC from the two symmetric bisphenyl and bis-hexanoic dye products. The purified dye 75 was then sulfonated by the standard procedure described for formation of 67 from 65 to give crude dye 76. Pure dye 76 was isolated by normal phase preparative thin layer chromatography (PTLC) developed with methanol/dichloromethane (1:4) or flash chromatography eluting with methanol/dichloromethane (1:9).

Figure 13:
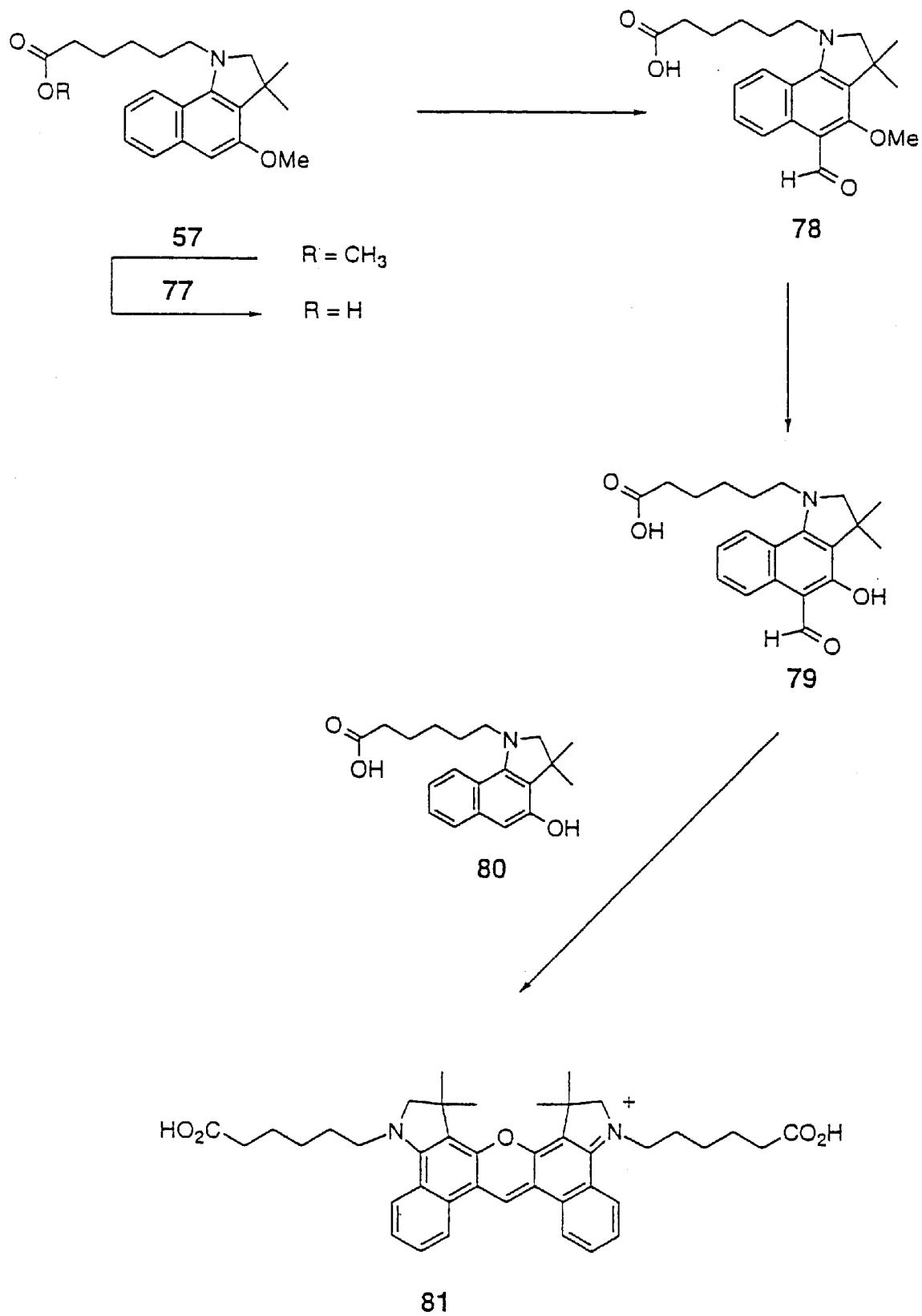
FIG. 13 shows a synthesis of compound 81.

Synthesis of Dye 81 (FIG. 13)

Compound 57 (0.313 g) was saponified by treatment with 7 equivalents of 1M KOH in methanol at room temperature over 3 hours. The solution was concentrated to dryness and the oil extracted well with ethyl acetate and 5% hydrochloric acid solution. The organic layer was dried with sodium sulfate and concentrated to a colorless oil. Pure 77 was isolated by normal phase chromatography eluting with 5% methanol/dichloromethane/0.1% acetic acid (yield 0.243 g; 84%).

Next, compound 77 (0.360 gm) was dissolved in dry dichloromethane (2 ml) and a solution of dichloromethyl-methyl ether (2.6 equivalents) and tin tetrachloride (4 equivalents). The solution was refluxed for 1.5 hrs. The mixture was extracted with ethyl acetate and 3M hydrochloric acid solution. The organic layer was washed with water and brine, dried over anhydrous Na$_2$SO$_4$. concentrated to an oil, and used without purification. There was an approximately equimolar mixture of compound 77 and 78 at this point, based on thin layer chromatography. This oil was dissolved in dry dichloromethane (8 ml), and cooled to −78° C. Demethylation of the mixture was carried out by established boron tribromide procedures to yield a mixture of Compounds 79 and 80. The resultant crude oil was dissolved in dry dichloromethane (5 ml) and phosphorus oxychloride (2 equivalents) was added; nitrobenzene (5 ml) was then added. The mixture was heated from 80 to 150° C. over 45 minutes and promptly removed from heat. The workup and isolation was performed as in Example 12 for the synthesis of compound 67 to yield crude dye 81. Pure dye 81 was isolated by PTLC as described in Example 12 for the synthesis of compound 67, yielding 32 mg.

Example 13

Figure 15:
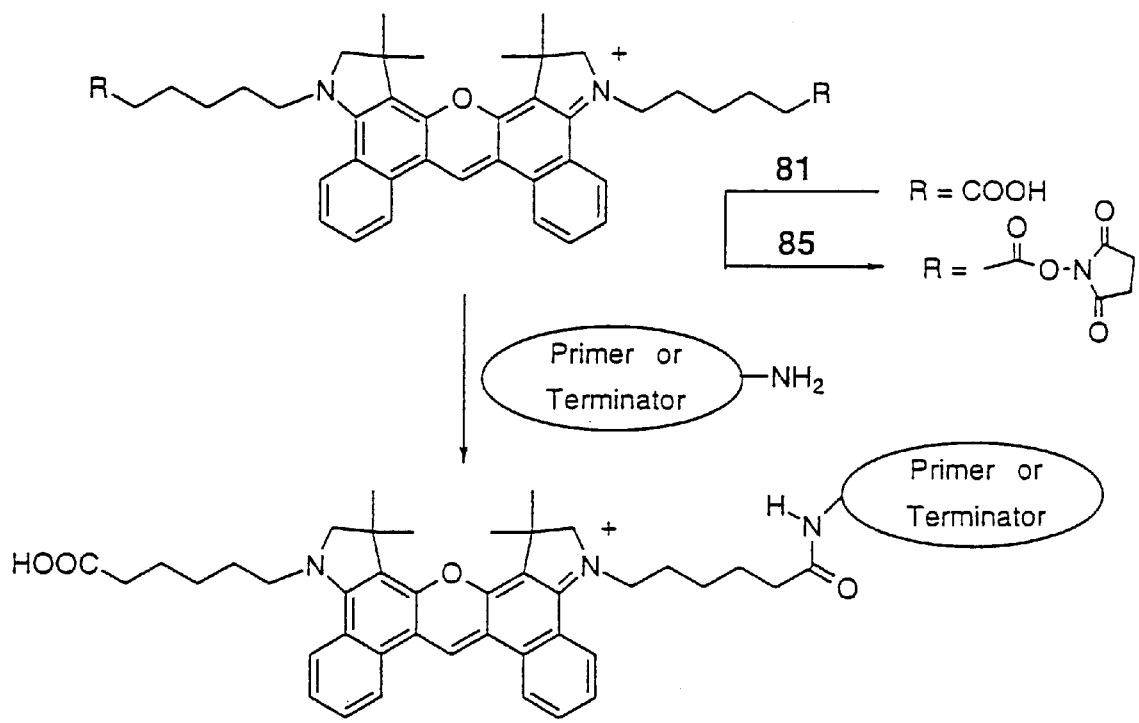
FIG. 15 shows a synthesis of compound 85.

Synthesis of Dye Carboxy N-Hydroxysuccinimide Derivatives of Compounds 67, 72, 76, and 81 and Coupling the Derivatives to Nucleotides and Polynucleotides (FIGS. 14 and 15)

The N-hydroxysuccinimide (NHS) derivatization of the carboxylic acid dyes 67, 72, 76, and 81 was accomplished by one of two methods. For synthesis of the NHS dyes 82, 83, and 84, Method A was employed with O-(N-succinimidyl)-N,N,N',N'-tetramethyluronium tetrafluoroborate reagent, while for dye 85, Method B was employed with dicyclohexylcarbodiimide (DCC) and N-hydroxysuccinimide.

Method A: The dye was suspended in dry DMF (5 mg dye: 300 µl DMF) with 6 equivalents of diisopropylethyl amine. To the dye solution was added 15 equivalents of O-(N-succinimidyl)-N,N,N',N'-tetramethyluronium tetrafluoroborate and the reaction was stirred for 15 minutes at room temperature. The reaction was transferred with dichloromethane into 5% HCl (20 ml). The aqueous layer was made salty by addition of saturated NaCl and extracted 3 times with dichloromethane. The combined organic layers were concentrated to dryness and the crude dye-NHS purified by normal phase flash chromatography eluting with MeOH/CH$_2$Cl$_2$ (1:9).

Method B: The dye and 20 equivalents of N-hydroxysuccinimide were suspended in dry dichloromethane (5 mg: 500 µl CH$_2$Cl$_2$). Nine equivalents of dicyclohexylcarbodiimide were added and the reaction was stirred for 1 hour at room temperature. The reaction was quenched and the pure dye-NHS isolated as for Method A.

Attachment of the NHS derivatives to nucleotides and polynucleotides was performed as follows. Amino group substituted oligomer or terminator was suspended in formamide (5×10$^{-4}$ M) and 15 equivalents of diisopropylethylamine were added. An excess (5–10 equivalents) of dye-NHS suspended in DMSO (5 mg/60 µl) were added with stirring at room temperature. The reaction was stirred at room temperature for 4 hours. To the reaction mixture was added 3 M NaOAc to give 0.5 M NaOAc. Four times the reaction volume of EtOH were added and the mixture was cooled. The precipitated dye labeled oligomer was isolated by centrifugation and purified by reverse phase HPLC eluting with 30% AcCN/0.1×TEAA buffer.

Example 14

Figure 16:
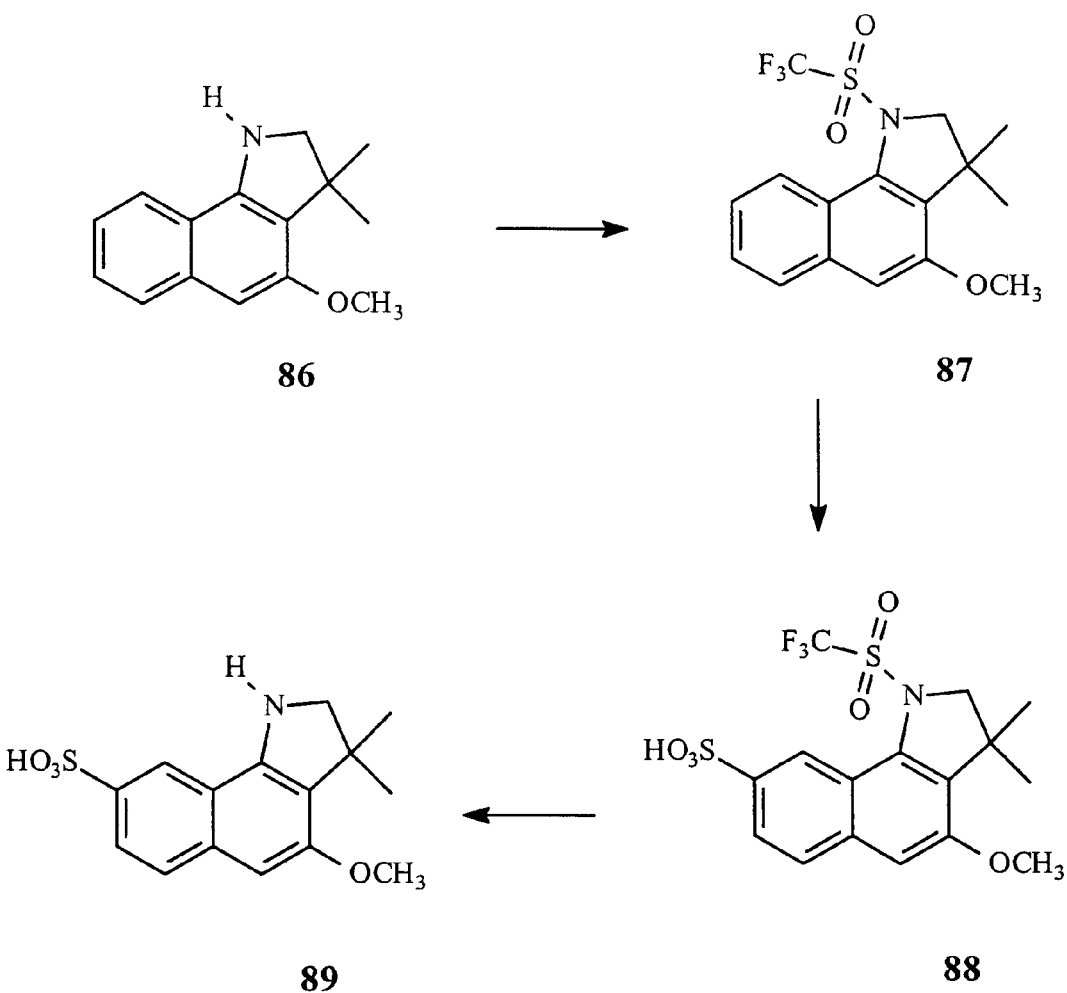
FIG. 16 shows a synthesis of compound 89.
Figure 17B:
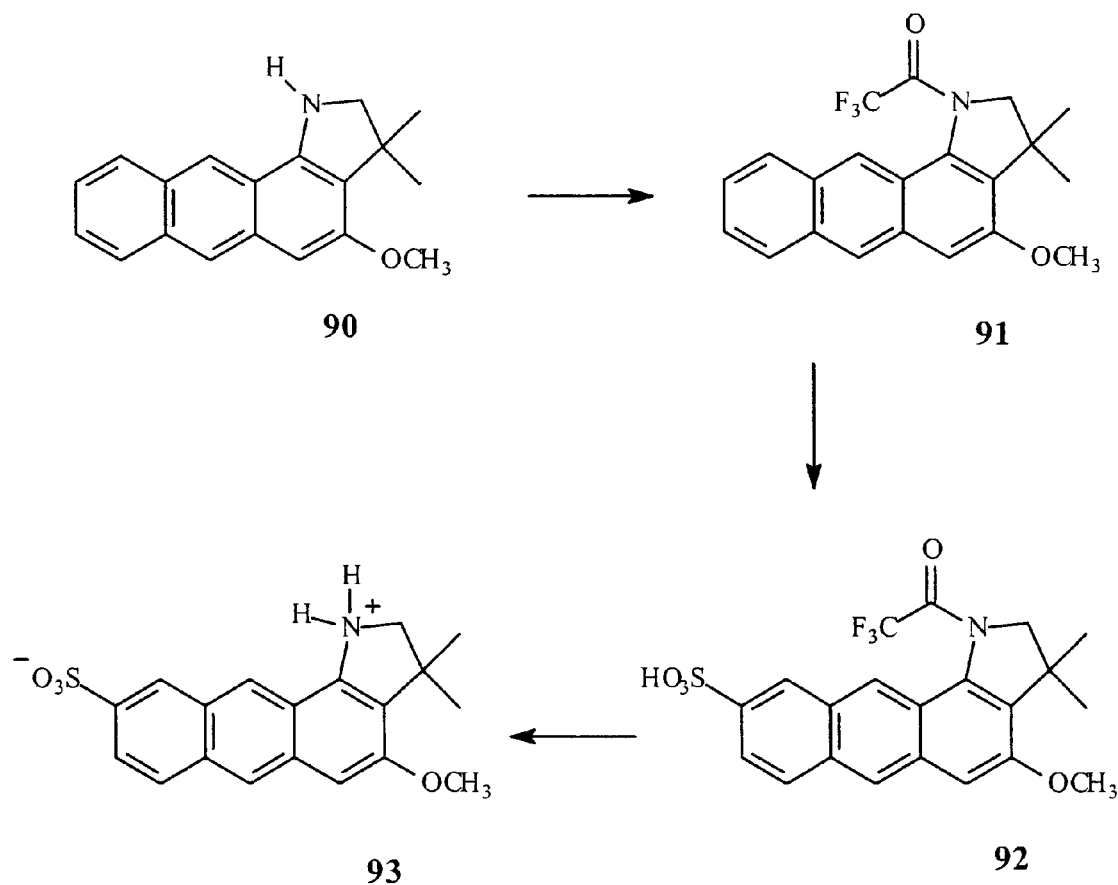
FIG. 17b shows a synthesis of compound 93.
Figure 18:
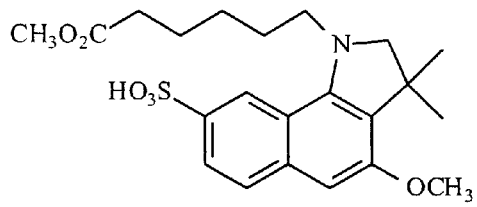
FIG. 18 shows compounds 94–99.
Figure 18:
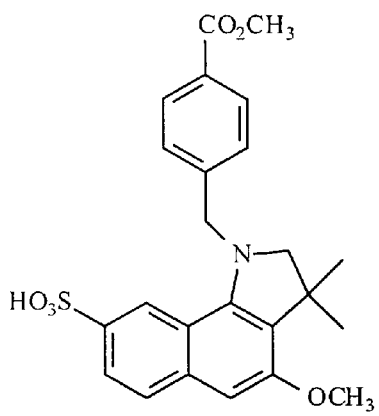
Figure 18:
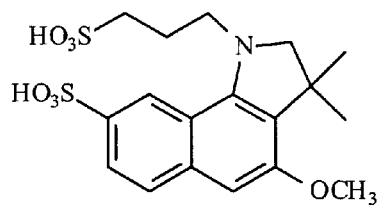
Figure 18:
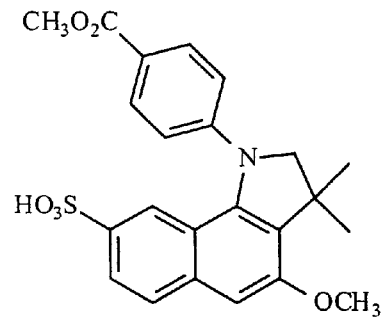
Figure 18:
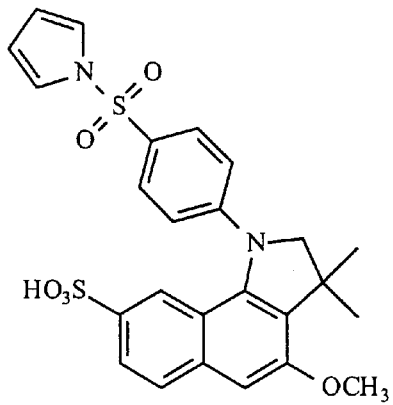
Figure 18:
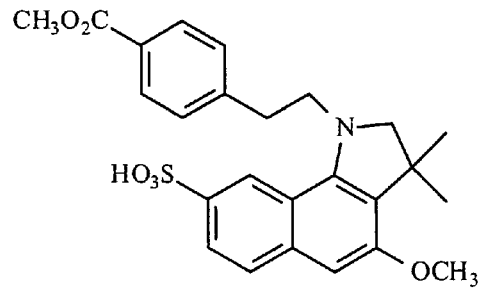
Figure 19:
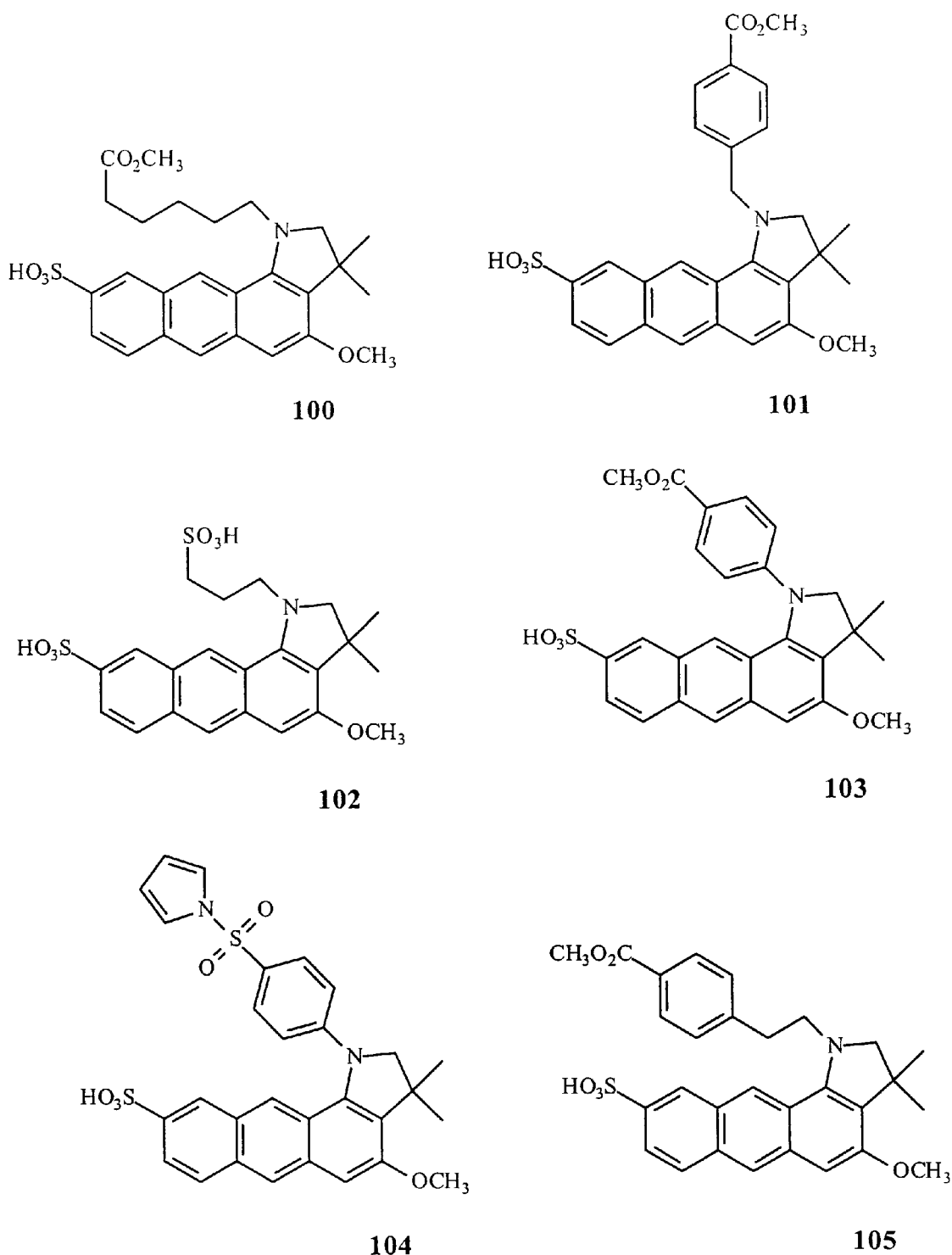
FIG. 19 shows compounds 100–105.

Synthesis of Sulfomethoxybenzoindoline 89 (FIG. 16)

Methoxybenzoindoline 86 (1 gram, 0.0044 mole) was suspended in 50 ml of dry CH$_2$Cl$_2$, and the solution was cooled to –20° C. in a water/acetone dry ice bath and purged well with argon (FIG. 16). To the stirred solution, 1.1 equivalents (0.82 ml) of trifluoromethanesulfonic acid anhydride were added dropwise. After addition of the anhydride was complete, the reaction was maintained at –20° C. and stirred while 2 equivalents of dry triethylamine (1.2 ml) were added dropwise. After one hour the reaction was quenched at –20° C. by addition of 5% HCl, and the aqueous phase was extracted 3 times with CH$_2$Cl$_2$. The combined organic layers were washed with saturated NaHCO$_3$, brine, dried with NaSO$_4$, filtered, and the solvent removed under vacuum. The crude product was purified by normal phase chromatography eluting with hexane:CH$_2$Cl$_2$ (3:2) to give 2.3 grams of the sulfonamide 87 (68% yield).

In a 250 ml round bottom flask, sulfonamide 87 (1 gram, 0.00279 mole) and granular anhydrous Na$_2$SO$_4$ (0.1 gram) were suspended in 100 ml of dry CH$_2$Cl$_2$. The reaction mixture was purged well with argon and cooled to 0° C. To the rapidly stirred solution, one equivalent of chlorosulfonic acid (185 µl) was added dropwise. The reaction was allowed to warm to room temperature and stirred under argon for 16 hours. The reaction was quenched by addition of 50 ml of THF, 75 ml of 1 M NaOH, and stirred for 2 hours. One equivalent of tetrabutylammonium hydrogensulfate (1 gram) was added to the mixture and the aqueous phase was extracted 5× with CH$_2$Cl$_2$. The organic phase was concentrated under vacuum to an oily solid mixture of 88 and other regioisomers. Purification by normal phase chromatography eluting with MeOH:CH$_2$Cl$_2$ (8:92) gave one gram of pure 88 (53% yield) mono tetrabutylammonium salt.

Sulfonamide 88 tetrabutylammonium salt (1 gram) was suspended in 50 ml of dry THF. Lithium aluminum hydride (20 equivalents, 1 gram) was added carefully and the reaction was refluxed under argon for 2 hours. The reaction was quenched by the careful addition of ice and then 50 ml of 1 M NaOH. Tetrabutylammonium hydrogensulfate (1 gram) was added to the mixture, and the mixture was concentrated under vacuum to remove most of the THF. The mixture was transferred to a separatory funnel and extracted 5× with CH$_2$Cl$_2$. The combined organic layers were concentrated to an oil under vacuum and purified by normal phase chromatography eluting with MeOH:CH$_2$Cl$_2$ (8:92) to give 0.733 gram of pure 89 (89% yield) tetrabutylammonium salt.

Example 15

Synthesis of sulfomethoxynaphthoindoline 93 (FIGS. 17a and 17b)

Methoxynaphthoindoline 90 was prepared by heating 24.9 gm of 1,3-dimethoxyanthracene 121 (Fitzgerald (1992) Jour. Org. Chem. 57:7122–26) in 48% HBr (175 ml) and glacial acetic acid (450 ml) for 1 hour at 90° C. (FIG. 17a). The reaction mixture was poured slowly into ice and water with stirring. A precipitate of 1,3-dihydroxyanthracene 122 formed immediately, which was filtered, washed with 300 ml cold water, and collected as a brown solid. Compound 122 was added to 0.14 M HCl in methanol at 5° C. and kept at 5° C. for 3 hours under argon. The reaction mixture was diluted with cold water (1000 ml) and extracted three times with a 3:2 mixture of hexane:ethylacetate. The combined organic extracts were washed with sat. NaCl and dried with Na$_2$SO$_4$. After filtering, removing solvent under vacuum, and normal phase silica gel chromatography eluting with hexane and ethylacetate, 123 was obtained as a bright yellow solid (6.93 gm, 66%).

Trifluoromethanesulfonic acid anhydride (6.8 ml) was slowly added to a stirred solution of 123 (7.0 gm, 0.031 moles) and dichloromethane (600 ml) at –60° C. under argon. After 20 minutes, triethylamine (5.65 ml) was added dropwise to the reaction. The reaction mixture was stirred at –30° C. for 30 minutes, then poured in 5% aqueous sulfuric acid. The mixture was then extracted with 400 ml of a 2:3 mixture of hexane:dichloromethane, washed with sat. NaCl, dried with Na$_2$SO$_4$, filtered, and concentrated under vacuum. Normal phase silica gel chromatography eluting with hexane and ethylacetate, gave 124 as a light yellow oil which solidified upon cooling. Hydrazine (6 ml) was added to a stirred solution of 124 (6 gm, 0.017 moles), $Cs_2CO_3$ (30 gm, $Pd_2(dba)_3$ (0.75 gm), BINAP (1.5 gm), toluene (100 ml), and THF (100 ml) at room temperature under argon, and then heated at 90–100° C. for 1 hour. The cooled solution was filtered and the solvent removed under vacuum to give 125 as a brown solid. A solution of 125 in absolute ethanol and isobutyraldehyde (14 ml) was heated at 90–100° C. The solution was evaporated to dryness and purified by normal phase silica gel chromatography eluting with hexane and ethylacetate, to give 126 as a bright yellow solid.

A solution of 126 in glacial acetic acid (150 ml) was heated at 88° C. for 1 hour under argon with stirring. The solution was cooled in an ice bath and $NaCNBH_3$ (3 gm) was added in portions over 15 minutes and stirred at room temperature for an additional 15 minutes. The acetic acid was removed under vacuum, the residue was suspended in dichloromethane, and washed with 1N NaOH, sat. $NH_4Cl$, and sat. NaCl. Solvent was removed under vacuum and the residue was purified by normal phase silica gel chromatography eluting with hexane and ethylacetate, to give 90 as a light yellow solid (2.5 gm, 53%).

Methoxynaphthoindoline 90 (1 gram, 3.6 mmole) was suspended in 40 ml of dry $CH_2Cl_2$, the solution was cooled to 0° C. in an ice bath and purged with argon (FIG. 17). To the stirred solution, 1.5 equivalents of trifluoroacetic anhydride (0.76 ml) were added dropwise. After addition of the anhydride is complete, the reaction was maintained at 0° C. and stirred while 2 equivalents of dry triethylamine (1 ml) were added dropwise. After one hour the reaction was quenched by addition of 5% HCl, and the aqueous phase was extracted 3× with $CH_2Cl_2$. The combined organic layers were washed with saturated $NaHCO_3$, brine, and the organic layer was dried with $NaSO_4$, filtered, and the solvent removed under vacuum. The crude product was purified by normal phase chromatography employing 1:4 EtOAc:hexane to give 1 gram of 91, a yellow solid (yield 74%).

The trifluoroacetamide 91 (1 gram, 2.7 mmole), was suspended in 60 ml of glacial acetic acid and 6 ml of dry $CH_2Cl_2$. The solution was purged well with argon and cooled to 0° C. The solution was stirred well and chlorosulfonic acid (4 ml, 20 equivalents) was added dropwise. The reaction was allowed to warm to room temperature and stir for three days. The reaction was quenched by addition of a minimal amount of ice (approximately one gram). The solvents were removed en vacuo with addition of toluene to help remove the acetic acid. The crude reaction mixture was suspended in a minimal amount of 1:4 MeOH:$CH_2Cl_2$ and partially purified by passage through a silica gel plug, eluting first with $CH_2Cl_2$ and then increasing to 1:20 MeOH:$CH_2Cl_2$ to give a mixture of 92 and other sulfonated regioisomers.

The mixture including 92 was deprotected by suspension in 100 ml of MeOH containing one ml of water and 1.5 grams of $K_2CO_3$. The reaction was stirred for 30 minutes at room temperature. The crude reaction mixture was passed through a plug of silica gel eluting with MeOH and the solvent was removed en vacuo. The desired isomer sulfomethoxynaphthoindoline 93 (0.350 gram, yield 37%) was separated from the byproduct isomers by normal phase chromatography employing gradient elution from 1:9 to 1:6 MeOH:$CH_2Cl_2$ (FIG. 17b).

Example 16

Figure 20:
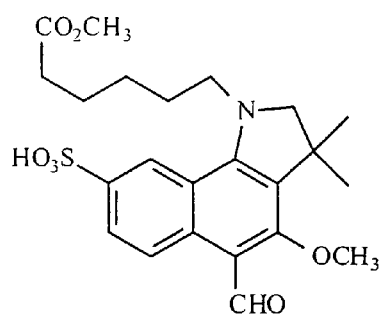
FIG. 20 shows compounds 106–109.
Figure 20:
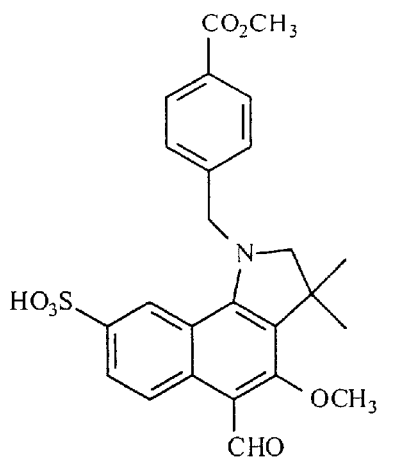
Figure 20:
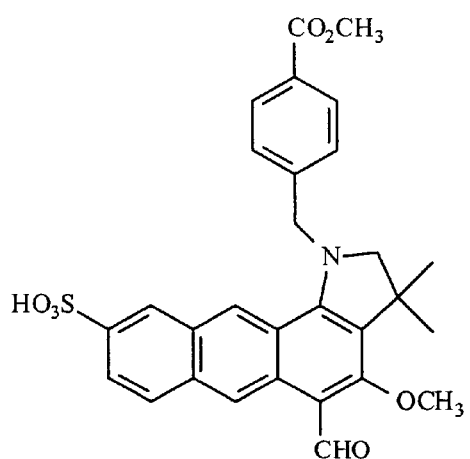
Figure 20:
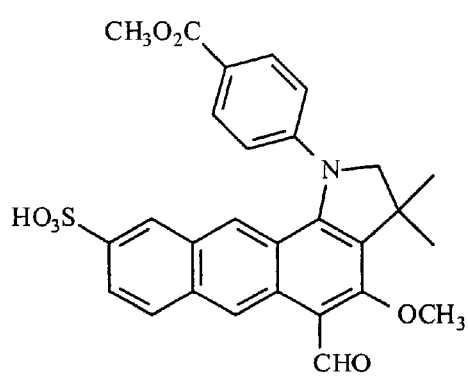
Figure 21:
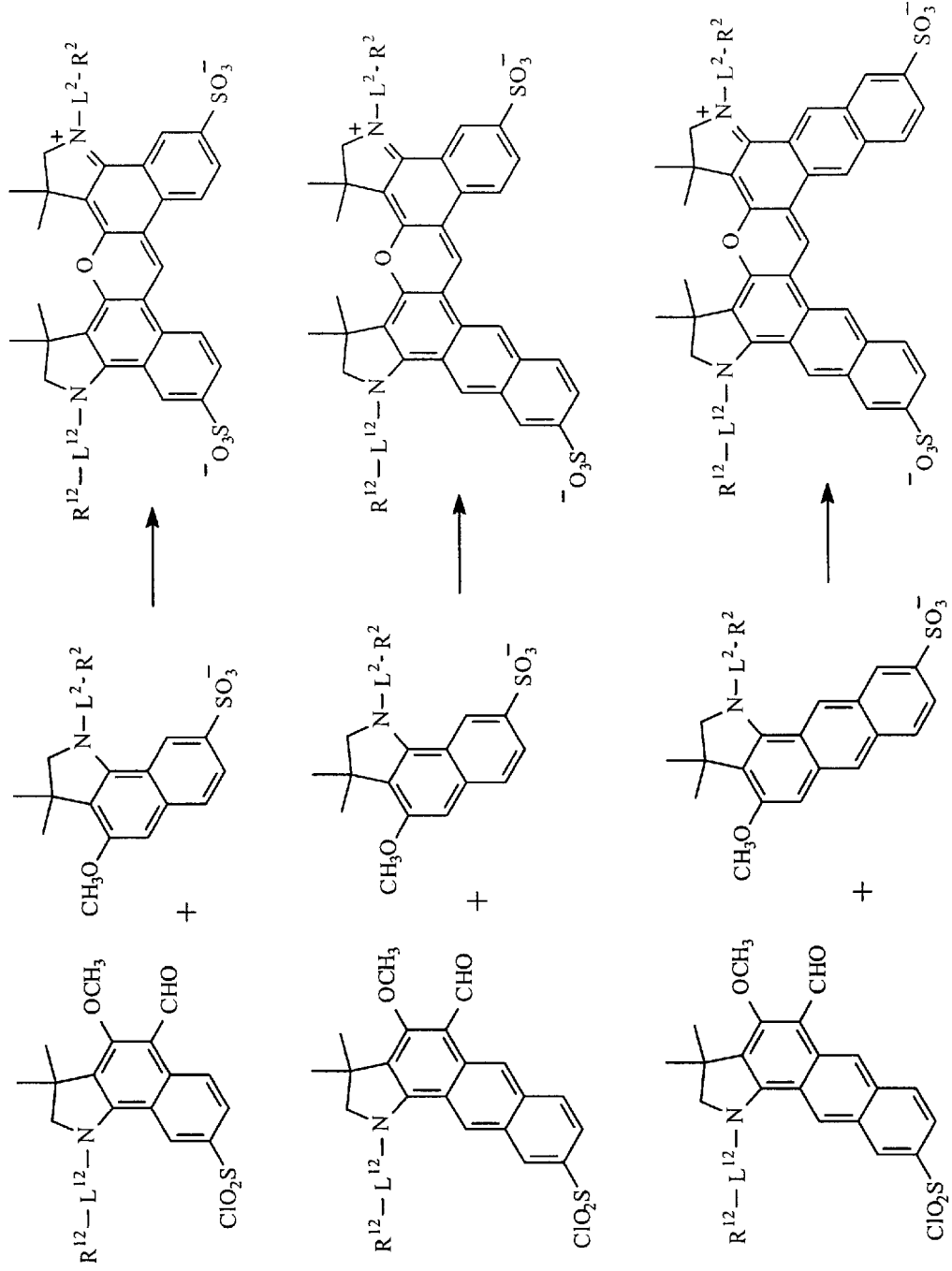
FIG. 21 shows cyclization reactions to form sulfonated dibenzorhodamine compounds (top), sulfonated benzo-naphthorhodamine compounds (middle), and sulfonated dinaphthorhodamine compounds (bottom).

Synthesis of formyl-sulfomethoxybenzoindoline 106 (FIG. 20)

N-methylcarboxyhexyl-sulfomethoxybenzoindoline 94 (FIG. 18) was prepared by alkylation of 89 with methyl 6-bromohexanoate with heating. In a 100 ml round bottom flask, one gram (918, 1.1 mmole) of 94, as a tetrabutylammonium salt mix, was suspended in 25 ml dry $CH_2Cl_2$. The solution is purged well with argon and cooled to 0° C. in an ice bath. To the stirred solution was added dropwise 5 equivalents of a freshly generated 1:1 Vilsmeyer complex of $POCl_3$/DMF in $CH_2Cl_2$ (5 equivalents complex in approximately 1 ml $CH_2Cl_2$, see below). The reaction was removed from the ice bath and stirred for 1 hour at room temperature. The reaction was quenched by addition of saturated $NaHCO_3$ (10 ml) and THF (20 ml) and stirring at room temperature for 30 minutes. The mixture is transferred with $CH_2Cl_2$ into a separatory funnel, the organic layer was removed, the aqueous layer is extracted 3 times with $CH_2Cl_2$, and the combined organic layers are concentrated to give crude 106 (FIG. 20). From the crude oil, pure aldehyde 106 was isolated by normal phase chromatography employing EtOAc: hexane (1:2), as a yellow solid (0.222 gram, 42% yield).

Example 17

Synthesis of formyl-sulfomethoxynaphthoindoline 108 (FIG. 20)

Sulfomethoxynaphthoindoline 101 (FIG. 19) was prepared by alkylation of 93 (FIG. 18) with methyl 4-(bromomethyl)benzoate with heating. In a 100 ml round bottom flask, one gram (1 mmole) of 101 as the tetrabutylammonium salt was suspended in 25 ml of dry dichloromethane. The solution was purged well with argon and cooled to 0° C. in an ice bath. To the stirred solution was added 5 equivalents of a freshly generated 1:1 Vilsmeyer complex of $POCl_3$/DMF in $CH_2Cl_2$ (5 equivalents in approximately 1 ml $CH_2Cl_2$, see below). After stirring for one hour at room temperature, the reaction was quenched by addition of saturated $NaHCO_3$ (10 ml) and THF (20 ml) and stirred at room temperature for 30 minutes. The mixture was transferred to a separatory funnel with $CH_2Cl_2$, the organic layer was removed and the aqueous layer extracted 3 times with $CH_2Cl_2$. The combined organic layers were concentrated to give crude 108 (FIG. 20). The crude product was subjected to normal phase chromatography employing EtOAc:hexane (1:2), to give 0.497 gram of pure aldehyde product 108 as a yellow solid (90% yield).

Vilsmeyer Reagent: A 10 ml flask was charged with 8.5 ml of dry $CH_2Cl_2$ and 660 ul of dry DMF. The solution was cooled to 0° C. and purged well with argon. To this stirred solution was added dropwise 790 $\mu$l of $POCl_3$. The reaction was stirred at 0° C. for 15 min prior to use. The requisite amount of complex is then removed with a syringe as needed.

Example 18

Synthesis of sulfonated dibenzorhodamine dye 111 (FIG. 22a)

N-propylsulfonate benzoindoline 96 (FIG. 18) was prepared by alkylation of 89 (FIG. 16) with 1,3-propane sultone with heating. Into a 20 ml pear flask were added 50 mg of formyl benzoindoline 106 (FIG. 20), 1.2 equivalents 96, 5 ml dry $CH_2Cl_2$ and 3 ml dry nitrobenzene. The mixture was stirred and heated to 110° C. under a steam of argon until most of the $CH_2Cl_2$ was evaporated. Excess phosphorus oxychloride (300 ul, 60 equivalents) was added in one portion and the reaction was heated with stirring for 2 hours.

The reaction was allowed to cool briefly, then 5 ml of MeOH were added and the reaction was heated to reflux for 5 minutes. The MeOH and some excess nitrobenzene were removed en vacuo, and the crude mixture was loaded onto a normal phase silica gel column. The dye 111 was eluted by gradient elution from 100% $CH_2Cl_2$ to 1:9 $MeOH:CH_2Cl_2$. The fractions containing esterified dye 111, as indicated by the visible absorption spectrum (Absorption maximum at 638 nm in MeOH) and fluorescence emission spectrum (Emission maximum at 651 nm in MeOH), and mass spectrum (Molecular ion plus 3 methyl groups equal 871.5, calculated 871.3), were collected and concentrated to an oil. The sulfonate and carboxylate methyl ester groups were hydrolyzed by suspension in 100 ml MeOH, 20 ml water, 0.85 grams LiOH hydrate, and heating at 80° C. for one hour. The bulk of the methanol was removed under vacuum. Three equivalents of tetrabutylammonium salt were added and the aqueous layer was extracted 5× with $CH_2Cl_2$. The combined organic layers were concentrated to an oil and reverse phase HPLC employing 1:3 $CH_3CN:H_2O$ gave the pure dye 111 in 20% overall yield (FIG. 22a).

Example 19

Synthesis of sulfonated benzo-naphthorhodamine dyes 115 (FIG. 22b)

N-propylsulfonate naphthoindoline 102 (FIG. 19) was prepared by alkylation of 93 (FIG. 17) with 1,3-propane sultone with heating. Formyl-benzoindoline derivative 107 (FIG. 20) was prepared by formylation of 95 (FIG. 18) by the procedures of Example 17.

Into a 20 ml pear flask were added 50 mg 107, 1.2 equivalents 102, 5 ml $CH_2Cl_2$ and 3 ml nitrobenzene. The mixture was stirred and heated to 120° C. under a steam of argon until most of the $CH_2Cl_2$ was evaporated. Excess phosphorous oxychloride (300 μl, 60 equivalents) was added in one portion and the reaction heated with stirring for 2 hours. The reaction was allowed to cool briefly, then 10 ml of MeOH was added and the reaction was heated to reflux for 5 minutes. The MeOH and some excess nitrobenzene were removed under vacuum, and the crude mixture was loaded on a normal phase silica gel column. The methyl ester of dye 115 was eluted by gradient elution from 100% $CH_2Cl_2$ to 1:9 $MeOH:CH_2Cl_2$. The fractions containing methyl ester of 115, as indicated by the visible absorption spectrum (Absorption maximum at 656 nm in MeOH), fluorescence emission spectrum (Emission maximum at 672 nm in MeOH), and mass spectrum (Molecular ion plus 3 methyl groups equals 885.3, calculated 885.2) were collected and concentrated to an oil. The sulfonate and carboxylate methyl ester groups were hydrolyzed by suspension in 100 ml MeOH, 20 ml water, 0.85 grams LiOH hydrate, and heating at 80° C. for one hour. The bulk of the methanol was removed under vacuum. Three equivalents of tetrabutylammonium salt were added and the aqueous layer was extracted 5× with $CH_2Cl_2$. The combined organic layers were concentrated to an oil and reverse phase chromatography employing 1:3 $CH_3CN:H_2O$ gave the pure dye 115 in 20% overall yield (FIG. 22b).

Example 20

Synthesis of sulfonated dinaphthorhodamine dye 120 (FIG. 22c)

N-propylsulfonate naphthoindoline 102 (FIG. 19) was prepared by alkylation of 93 (FIG. 17) with 1,3-propane sultone with heating. Formyl-benzoindoline derivative 108 (FIG. 20) was prepared by formylation of 101 (FIG. 101) by the procedures of Example 17.

Into a 20 ml pear flask are added 50 mg 108, 1.2 equivalents 102, 5 ml $CH_2Cl_2$ and 3 ml nitrobenzene. The mixture was stirred and heated to 110° C. under a steam of argon until most of the $CH_2Cl_2$ has evaporated. Excess phosphorous oxychloride (300 μl, 60 equivalents) was added in one portion and the reaction was heated with stirring for 2 hours. The reaction was allowed to cool briefly, then 5 ml of MeOH was added and the reaction was heated to reflux for 5 minutes. The MeOH and some excess nitrobenzene were removed under vacuum, and the crude mixture was loaded on a normal phase silica gel column. The dye 120 was eluted by gradient elution from 100% $CH_2Cl_2$ to 1:9 $MeOH:CH_2Cl_2$. The fractions containing esterified dye 120, as indicated by the visible absorption spectrum (Absorption maximum at 686 nm in MeOH) and fluorescence emission spectrum (Emission maximum at 695 nm), and mass spectrum (Molecular ion plus 3 methyl groups equals 991.5, calculated 991.3), were collected and concentrated to an oil. The sulfonate and carboxylate methyl ester groups were hydrolyzed by suspension in 100 ml MeOH, 20 ml water, 0.85 grams LiOH hydrate, and heating at 80° C. for one hour. The bulk of the methanol was removed under vacuum. Three equivalents of tetrabutylammonium salt were added and the reaction was extracted 5× with $CH_2Cl_2$. The combined organic layers were concentrated to an oil and reverse phase chromatography employing 1:3 $CH_3CN:H_2O$ gave the pure dye 120 in 20% overall yield (FIG. 22c).

Example 21

Sequencing of pGEM with sulfonated diarylrhodamine-terminators

Following the conditions of U.S. Pat. Nos. 5,770,716; 5,948,648; and 6,096,875, terminators labelled with sulfonated diarylrhodamine dyes of the invention are used with other standard reagents in Sanger-type, four-color automated DNA sequencing experiments.

Dye-terminator sequencing reactions are performed using AmpliTaq DNA Polymerase, FS following protocols provided in the ABI PRISM™ Dye Terminator Cycle Sequencing Core Kit Manual (Applied Biosystems p/n 402116). Sequencing of the pGEM-3Zf(+) template was conducted with unlabelled −21 M13 sequencing primer (forward). Reagents, including buffer, unlabelled primer, AmpliTaq DNA Polymerase, FS, may be from an ABI PRISM™ Dye Terminator Core Kit (Applied Biosystems p/n 402117). The dNTP mix may consist of 2 mM each of dATP, dCTP, dITP, and dUTP or dTTP. A premix of reaction components is prepared including: 5×Buffer 4.0 μL; dNTP mix 1.0 μL; Template:pGEM®-3Zf(+), 0.2 μg/μL, 2.0 μL; Primer: −21 M13 (forward), 0.8 pmol/μL, 4.0 μL; AmpliTaq DNA Polymerase, FS, 0.5 μL; and $H_2O$ 3.5 μL, wherein all quantities are given on a per reaction basis.

Exemplary reactions are assembled in 0.5 ml tubes adapted for the Perkin-Elmer 480 DNA Thermal Cycler (Applied Biosystems p/n N801-100 or 0.2 ml tubes for the Applied Biosystems Gene Amp PCR System 9700). From 1 to 250 pmol of the dye terminator are added to each reaction.

30 μl of mineral oil is added to the top of each reaction to prevent evaporation (when using the Applied Biosystems 480 Thermal Cycler). Reaction volumes are 20 μL, including 15 μL of the above reaction premix, a variable amount of dye labelled terminator, and a sufficient volume of water to bring the total reaction volume up to 20 μL. Reactions are thermocycled as follows: 96° C. for 30 sec, 50° C. for 15 sec, and 60° C. for 4 min, for 25 cycles; followed by a 4° C. hold cycle.

All reactions are purified by spin-column purification on Centri-Sep spin columns according to manufacturer's instructions (Princeton Separations p/n CS-901). Gel material in the column is hydrated with 0.8 ml deionized water for at least 30 minutes at room temperature. After the column is hydrated and no bubbles are trapped in the gel material, the upper and lower end caps of the column are removed, and the column is allowed to drain by gravity. The column is then inserted into the wash tubes provided in the kit and centrifuged in a variable speed microcentrifuge at 1300 g for 2 minutes, removed from the wash tube, and inserted into a sample collection tube. The reaction mixture is carefully removed from under the oil and loaded onto the gel material and the tube re-centrifuged. Eluted samples are then dried in a vacuum centrifuge.

Prior to loading onto a sequencing gel, the dried samples are resuspended in 25 μL of Template Suppression Reagent (Applied Biosystems p/n 401674), vortexed, heated to 95° C. for 2 minutes, cooled on ice, vortexed again, and centrifuged (13,000×g). 10 μL of the resuspended sample is aliqoted into sample vials (Applied Biosystems p/n 401957) adapted for the ABI PRISM™ 310 Genetic Analyzer (Applied Biosystems p/n 310-00-100/120). Electrophoresis on the 310 Genetic Analyzer is performed with sieving polymers and capillaries specially adapted for DNA sequencing analysis (Applied Biosystems p/n 402837 or 4313087 (polymer) and p/n 402840 (capillary)). The sieving polymer includes nucleic acid denaturants. Samples are electrokinetically injected onto the capillary for 30 sec at 2.5 kV, and run for up to 2 hr at 10 to 12.2 kV with the outside wall of the capillary maintained at 50° C. to generate an electropherogram as sequencing data.

The sulfonated diarylrhodamine terminators are specifically incorporated onto the 3' terminus of primer extension, polynucleotide fragments during four-color sequencing reactions. Eluting fragments from 1 to about 1000 base pairs are detected and plotted. An electropherogram plots the fluorescence intensity emitted by the sulfonated diarylrhodamine dye of the labelled fragments eluting by length as a function of time during an electrophoresis run on the ABI PRISM™ 310 Genetic Analyzer.

All publications, patents, and patent applications referred to herein are hereby incorporated by reference to the same extent as if each individual publication, patent or patent application was specifically and individually indicated to be incorporated by reference.

Although only a few embodiments have been described in detail above, those having ordinary skill in the chemical arts will clearly understand that many modifications are possible in these embodiments without departing from the teachings thereof. All such modifications are intended to be encompassed within the scope of the following claims.

We claim:

1. Sulfonated diarylrhodamine compounds having the structures:

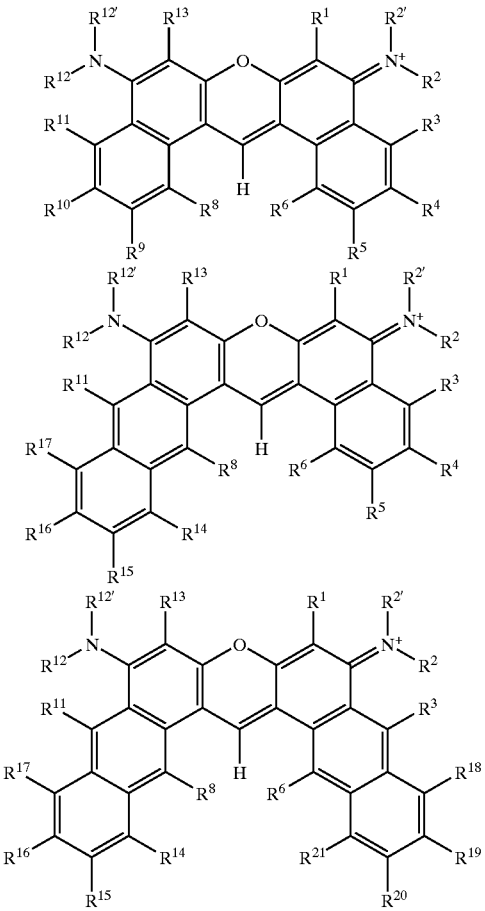

wherein $R^2$, $R^{2'}$, $R^{12}$ and $R^{12'}$ is hydrogen, $C_1$–$C_{12}$ alkyl, $C_1$–$C_{12}$ alkyldiyl, phenyl, substituted phenyl, benzyl, substituted benzyl, biphenyl, substituted biphenyl, naphthyl, substituted naphthyl, heterocycle, substituted heterocycle, water-solubilizing group or linking moiety; and $R^1$, $R^3$, $R^4$, $R^5$, $R^6$, $R^8$, $R^9$, $R^{10}$, $R^{11}$, $R^{13}$, $R^{14}$, $R^{15}$, $R^{16}$, $R^{17}$, $R^{18}$, $R^{19}$, $R^{20}$, and $R^{21}$ is hydrogen, fluorine, chlorine, $C_1$–$C_8$ alkyl, carboxylate, sulfate, sulfonate, alkylsulfonate, aminomethyl (—$CH_2NH_2$), aminoalkyl, 4-dialkylaminopyridinium, hydroxymethyl (—$CH_2OH$), methoxy (—$OCH_3$), hydroxyalkyl (—ROH), thiomethyl (—$CH_2SH$), thioalkyl (—RSH), alkylsulfone (—$SO_2R$), arylthio (—SAr), arylsulfone (—$SO_2Ar$), sulfonamide (—$SO_2NR_2$), alkylsulfoxide (—SOR), arylsulfoxide (—SOAr), amino (—$NH_2$), ammonium (—$NH_3^+$), anildo (—$CONR_2$), nitrile (—CN), $C_1$–$C_8$ alkoxy (—OR), phenoxy, phenolic, tolyl, phenyl, aryl, benzyl, heterocycle, phosphonate, phosphate, quaternary amine, sulfate, polyethyleneoxy, water-solubilizing group, or linking moiety;

with the proviso that at least one of $R^1$, $R^3$, $R^4$, $R^5$, $R^6$, $R^8$, $R^9$, $R^{10}$, $R^{11}$, $R^{13}$, $R^{14}$, $R^{15}$, $R^{16}$, $R^{17}$, $R^{18}$, $R^{19}$, $R^{20}$, and $R^{21}$ is sulfonate.

2. The compound of claim 1 wherein at least one of $R^2$, $R^{2'}$, $R^{12}$ and $R^{12'}$ is $C_1$–$C_6$ alkylsulfonate or $C_4$–$C_{10}$ arylsulfonate.

3. The compound of claim 1 wherein the alkyldiyl, substituted phenyl, substituted benzyl, substituted biphenyl, substituted heterocycle and substituted naphthyl is substituted with sulfonate.

4. The compound of claim 1 wherein the alkyldiyl, substituted phenyl, substituted benzyl, substituted biphenyl, substituted heterocycle and substituted naphthyl is substituted with carboxyl.

5. The compound of claim 1 wherein the linking moiety is azido, monosubstituted primary amine, disubstituted secondary amine, thiol, hydroxyl, halide, epoxide, N-hydroxysuccinimidyl ester, carboxyl, isothiocyanate, sulfonyl chloride, sulfonate ester, silyl halide, chlorotriazinyl, succinimidyl ester, pentafluorophenyl ester, maleimide, haloacetyl, epoxide, alkylhalide, allyl halide, aldehyde, ketone, acylazide, anhydride, iodoacetamide or an activated ester.

6. The compound of claim 1 wherein the water-solubilizing group is carboxylate, sulfonate, phosphonate, phosphate, quaternary amine, sulfate, polyhydroxyl, or water-soluble polymer.

7. The compound of claim 1 wherein the heterocycle is pyrrole, indole, furan, benzofuran, thiophene, benzothiophene, 2-pyridyl, 3-pyridyl, 4-pyridyl, 2-quinolyl, 3-quinolyl, 4-quinolyl, 2-imidazole, 4-imidazole, 3-pyrazole, 4-pyrazole, pyridazine, pyrimidine, pyrazine, cinnoline, pthalazine, quinazoline, quinoxaline, 3-(1,2,4-N)-triazolyl, 5-(1,2,4-N)-triazolyl, 5-tetrazolyl, 4-(1-O, 3-N)-oxazole, 5-(1-O, 3-N)-oxazole, 4-(1-S, 3-N)-thiazole, 5-(1-S, 3-N)-thiazole, 2-benzoxazole, 2-benzothiazole, 4-(1,2,3-N)-benzotriazole, or benzimidazole.

8. The compound of claim 1 wherein $R^1$, $R^3$, $R^6$, $R^8$, $R^{11}$, $R^{13}$, $R^{14}$, $R^{15}$, $R^{16}$, $R^{17}$, $R^{18}$, $R^{19}$, $R^{20}$, and $R^{21}$ are hydrogen.

9. The compound of claim 1 comprising a first bridging group which when taken together with the C-12-bonded nitrogen and the C-12 and C-13 carbons forms a first ring structure having from 4 to 7 members; and/or a second bridging group which when taken together with the C-2-bonded-nitrogen and the C-1 and C-2 carbons forms a second ring structure having from 4 to 7 members.

10. The compound of claim 9 wherein one or both of the first and second ring structures has five members.

11. The compound of claim 10 wherein the five membered ring structure includes one gem disubstituted carbon.

12. The compound of claim 11 wherein the gem substituents are ($C_1$–$C_8$) alkyl.

13. The compound of claim 11 wherein the gem substituents are methyl.

14. The compound of claim 10 wherein the five membered ring is substituted with linking moiety or water-solubilizing group.

15. The compound of claim 1 comprising a third bridging group which when taken together with the C-12-bonded nitrogen and the C-11 and C-12 carbons forms a third ring structure having from 5 to 7 members; and/or a fourth bridging group which when taken together with the C-2-bonded nitrogen and the C-2 and C-3 carbons forms a fourth ring structure having from 5 to 7 members.

16. The compound of claim 15 wherein one or both of the third and fourth ring structures has six members.

17. The compound of claim 16 wherein the six membered ring structure includes one gem disubstituted carbon.

18. The compound of claim 17 wherein the gem substituents are ($C_1$–$C_8$) alkyl.

19. The compound of claim 18 wherein the gem substituents are methyl.

20. The compound of claim 1 having the structures:

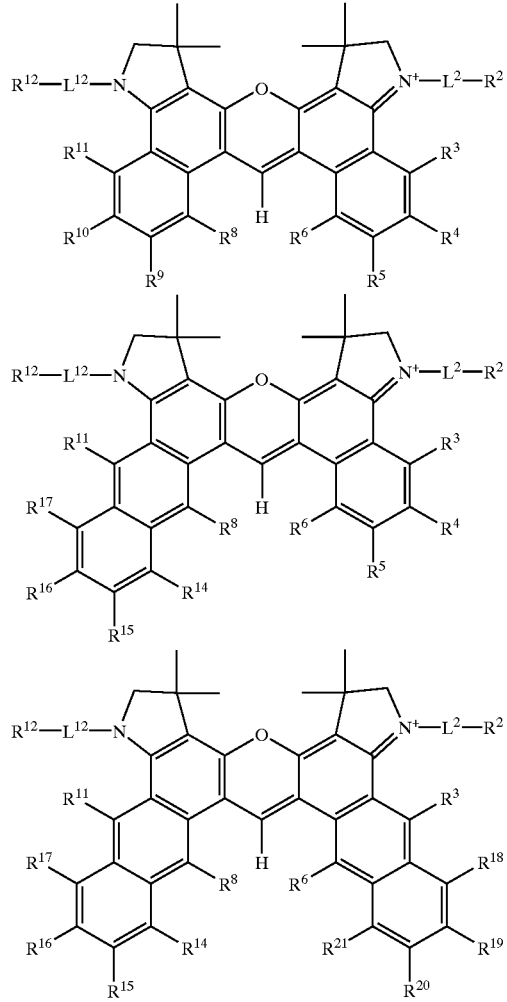

wherein $L^2$ and $L^{12}$ are linkers selected from the group consisting of alkyldiyl, substituted phenyl, substituted benzyl, substituted biphenyl, substituted heterocycle and substituted naphthyl.

21. The compound of claim 1 comprising a fused aromatic ring bonded across the C-3 and C-4 carbons, the C-4 and C-5 carbons, the C-9 and C-10 carbons, or the C-10 and C-11 carbons, including substituted forms thereof.

22. The compound of claim 1 comprising a fused aromatic ring bonded across the C-3 and C-4 carbons and the C-10 and C-11 carbons, including substituted forms thereof.

23. A kit for labelling a polynucleotide, comprising a sulfonated diarylrhodamine compound including a linking moiety according to claim 5 and a polynucleotide.

* * * * *